(12) United States Patent
Bhandari et al.

(10) Patent No.: US 7,189,851 B2
(45) Date of Patent: Mar. 13, 2007

(54) CONDENSED HETEROCYCLIC COMPOUNDS AS CALCITONIN AGONISTS

(75) Inventors: Ashok Bhandari, Milpitas, CA (US); Eric Eugene Boros, Durham, NC (US); David John Cowan, Durham, NC (US); Anthony Louis Handlon, Durham, NC (US); Clifton Earl Hyman, Durham, NC (US); Jeffrey Alan Oplinger, Durham, NC (US); Michael Howard Rabinowitz, San Diego, CA (US); Philip Stewart Turnbull, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 103 days.

(21) Appl. No.: 10/507,006

(22) PCT Filed: Feb. 24, 2003

(86) PCT No.: PCT/US03/05605

§ 371 (c)(1),
(2), (4) Date: Sep. 7, 2004

(87) PCT Pub. No.: WO03/076440

PCT Pub. Date: Sep. 18, 2003

(65) Prior Publication Data

US 2005/0107419 A1    May 19, 2005

Related U.S. Application Data

(60) Provisional application No. 60/362,011, filed on Mar. 6, 2002.

(51) Int. Cl.
C07D 471/00 (2006.01)
C07D 491/00 (2006.01)
C07D 498/00 (2006.01)
C07D 513/00 (2006.01)
C07D 515/00 (2006.01)

(52) U.S. Cl. .......................................... 546/82; 546/86
(58) Field of Classification Search ................. 546/85, 546/82, 86; 514/292

See application file for complete search history.

(56) References Cited

U.S. PATENT DOCUMENTS 6,133,273 A    10/2000  Magda et al.
6,221,874 B1    4/2001  Gerardo et al.

FOREIGN PATENT DOCUMENTS

WO           99/01455       *  1/1999

* cited by examiner

*Primary Examiner*—Margaret D. Seaman
*Assistant Examiner*—Niloofar Rahmani
(74) *Attorney, Agent, or Firm*—Amy H. Fix

(57) ABSTRACT

The present invention relates to novel fused heterocyclic ring system compounds and methods for their use in the treatment and prevention of diseases or conditions.

1 Claim, No Drawings

CONDENSED HETEROCYCLIC COMPOUNDS AS CALCITONIN AGONISTS

This application is filed pursuant to 35 U.S.C. 0 371 as a United States National Phase Application of International Application No. PCT/US03/05605 filed 24 Feb. 2003, which claims priority from US 60/362,011 filed 6 Mar. 2002.

FIELD OF THE INVENTION

The present invention relates to novel fused heterocyclic ring system compounds, processes for their manufacture and methods for their use in the treatment and prevention of diseases or conditions, particularly those diseases or conditions characterized by irregular calcification, such as osteopenia; osteoporosis; Paget's disease; bone fracture or deficiency; primary or secondary hyperparathyroidism; periodontal disease or defect; metastatic bone disorder; osteolytic bone disease; post-plastic surgery; post-prosthetic joint surgery; post-dental implantation; periodontal disease; hypercalcemia; bone pain, general pain and hyperalgesia; conditions associated with gastric secretion and motility; gastrointestinal disorders; osteoarthritis; rheumatoid arthritis; renal osteodystrophy; obesity by induction of satiety; or male infertility.

BACKGROUND OF THE INVENTION

Calcitonin is a peptide hormone composed of 32 amino acids and produced by C-cells of the thyroid gland in mammals. Eight forms of calcitonin in five species, including man, pig, and salmon, are known. Calcitonins have been approved by regulatory agencies for the treatment of osteoporosis. In addition, published medical and research studies have suggested roles for calcitonin in other physiological and pathophysiological processes including: osteopenia and osteoporosis in men and women, risk of vertebral and nonvertebral fractures, Paget's disease, bone fracture or deficiency, primary or secondary hyperparathyroidism, periodontal disease or defect, metastatic bone disorder, osteolytic bone disease, post-plastic surgery, post-prosthetic joint surgery, post-dental implantation, periodontal disease, hypercalcemia, bone pain, general pain and hyperalgesia, conditions associated with inhibiting gastric secretion, other gastrointestinal disorders, osteoarthritis and rheumatoid arthritis (pain, bone loss, and joint destruction), renal osteodystrophy, obesity by induction of satiety, and male infertility.

As one example, osteoporosis (OP) is a disease of the skeleton in which the amount of calcium present in the bones slowly decreases to the point where bones become brittle and prone to fracture. One type of OP occurs in women due to postmenopausal decreases in estrogen levels. The decline of estrogen, in turn, results in a rapid depletion of calcium from the skeleton. Often women with postmenopausal OP experience vertebral fractures (collapse of the spine), as well as fractures of the hip, wrist, and forearm resulting from minor impact or falls.

Another type of OP, often termed "low turnover" OP, results when the on-going processes of bone resorption and formation no longer coordinate. Bone resorption, and hence calcium release from the bone, is a result of cells known as osteoclasts, that breakdown the skeleton. Osteoblasts, on the other hand, rebuild the skeleton through collagen, calcium, and phosphorous deposition. Often, over time, bone resorption overcomes bone formation thereby resulting in the loss of bone density. This type of OP affects both men and women.

In the regulation of bone calcification, an elevation of serum calcium triggers the release of calcitonin. Calcitonin inhibits the formation and activity of osteoclast cells by acting upon specific calcitonin receptors and, in turn, lowers serum calcium levels. Calcitonin's action is opposite to that of parathyroid hormone (PTH) in that calcitonin prevents loss of calcium from bone, results in an increase in the deposition of calcium and phosphate in bone and lowers the level of calcium in the blood.

As noted above, calcitonins of various species have been used for the treatment of osteoporosis, most notably salmon calcitonin. A calcitonin mimetic, however, would circumvent issues particular to the calcitonin peptide, such as antibody production, short half-life and bioavailability variations. Thus, there is a need for calcitonin agonists for use in the treatment and prevention of diseases and conditions characterized by abnormal calcification as well as in conditions wherein calcitonin would have a beneficial pharmacological effect. Such conditions and diseases include, without limitation: osteopenia and osteoporosis in men and women; reduction in the risk of fractures, both vertebral and nonvertebral; Paget's disease; bone fracture or deficiency; primary or secondary hyperparathyroidism; periodontal disease or defect; metastatic bone disorder; osteolytic bone disease; post-plastic surgery; post-prosthetic joint surgery; post-dental implantation; hypercalcemia; bone pain, general pain, and hyperalgesia; conditions associated with inhibiting gastric secretion; gastrointestinal disorders; osteoarthritis and rheumatoid arthritis (pain, bone loss, and joint destruction); renal osteodystrophy; obesity by induction of satiety; and male infertility.

SUMMARY OF THE INVENTION

The present invention includes compounds of formula (I):

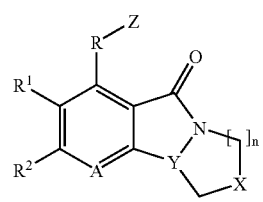

including salts, solvates, and pharmaceutically functional derivatives thereof, wherein R is aryl, heteroaryl, alkyl, or cycloalkyl,
further wherein said aryl, heteroaryl, alkyl, or cycloalkyl may be optionally substituted with one or more of alkyl, halogen, nitro, or trifluoromethyl;

Z is H, alkyl, halogen, $C(O)OR^5$, $C(O)N(R^5)_2$, $C(O)NHN(R^5)_2$, $NHC(O)N(R^5)_2$, $S(O)_2N(R^5)_2$, $CH_2NHC(O)R^5$, $NO_2$, $N(R^5)_2$, $NHC(O)R^5$, $N(R^5)S(O)_2N(R^5)_2$, $OR^5$, $CH_2N(R^5)_2$, $CH_2C(O)N(R^5)_2$, $CH_2C(O)OR^5$, heteroaryl, said heteroaryl optionally may be substituted with alkyl or aralkyl;

each occurrence of $R^5$ independently is H, alkyl, trifluoromethyl, aryl, heteroaryl, aralkyl, heteroaralkyl, cycloalkyl, heterocyclyl, fused cycloalkylaryl, or fused heterocyclylaryl further wherein said aryl, heteroaryl, aralkyl, heteroaralkyl, cycloalkyl, or heterocyclyl may be substituted with one or more halogen;

$R^1$ is H, alkyl, $C(O)OR^5$, $C(O)R^5$, $CON(R^5)_2$, CN, $NO_2$, $N(R^5)_2$, $S(O)_2R^5$, $S(O)_2N(R^5)_2$, $NHC(O)R^5$, $NHC(O)N(R^5)_2$, further wherein $R^5$ is as defined above;

$R^2$ is alkyl, trifluoromethyl, alkoxy, aryl, heteroaryl, aralkyl, heteroaralkyl, alkoxyaryl, further wherein said alkyl, aryl, heteroaryl, aralkyl, and heteroaralkyl may be substituted with one or more of halogen, trifluoromethyl, or alkoxy;

or $R^1$ and $R^2$ combine to form a 5- or 6-membered ring, optionally containing one or more heteroatom, optionally containing one or more degrees of unsaturation, and optionally substituted one or more times with oxo, hydroxy, halogen, alkyl, aryl, heteroaryl, aralkyl, heteroaralkyl, further wherein said alkyl, aryl, heteroaryl, aralkyl, and heteroaralkyl may be substituted with one or more of halogen, trifluoromethyl, or alkoxy;

A is C or N;

Y is C or N;

X is S, O, $N(R^5)$, $C(R^5)_2$, $S(O)_2$; and n is 1, 2, 3, or 4.

Preferably, R is heteroaryl. More preferably R is thiophenyl. Preferably, Z is $—C(O)N(R^5)_2$, wherein one $R^5$ is H and one $R^5$ is aralkyl substituted with one or more halogen. More preferably, Z is

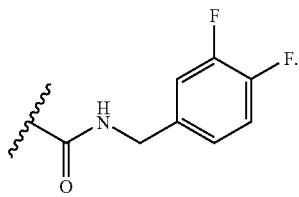

In another embodiment of the present invention, preferably Z is $—C(O)N(R^5)_2$, wherein one $R^5$ is H and one $R^5$ is a fused cycloalkylaryl. More preferably the fused cycloalkylaryl is

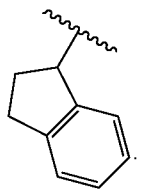

Preferably, $R^1$ is $—C(O)OR^5$, wherein $R^5$ is ethyl. Preferably, $R^2$ is aralkyl substituted with one or more halogen. More preferably, $R^2$ is

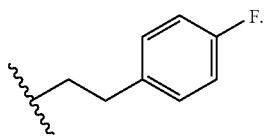

Preferably Y is C. Preferably X is $—C(R^5)_2—$, wherein each $R^5$ is H. Preferably n is 1.

Preferred compounds of formula (I) include:

Ethyl 2-[2-(4-fluorophenyl)ethyl]-4-(4-{[(2-furylmethyl)amino]carbonyl}phenyl)-5-oxo-8,9-dihydro-5H,7H-pyrazolo[1',2':1,2]pyrazolo[3,4-b]pyridine-3-carboxylate;

Ethyl 2-[2-(4-fluorophenyl)ethyl]-4-(5-{[(2-furylmethyl)amino]carbonyl}-2-thienyl)-5-oxo-8,9-dihydro-5H,7H-pyrazolo[1',2':1,2]pyrazolo[3,4-b]pyridine-3-carboxylate;

Ethyl (9aS)-5-oxo-4-[4-({[(1R)-1-(4-pyridinyl)ethyl]amino}carbonyl)phenyl]-2-{2-[4-(trifluoromethyl)phenyl]ethyl}-7,8,9,9a-tetrahydro-5H-pyrido[2,3-α]pyrrolizine-3-carboxylate;

Ethyl(9aS)-4-(4-{[(2-furylnethyl)amino]carbonyl}phenyl)-5-oxo-2-{2-[4-(trifluoromethyl)phenyl]ethyl}-7,8,9,9a-tetrahydro-5H-pyrido[2,3-a]pyrrolizine-3-carboxylate;

Ethyl(9aS)-4-{4-[(2,3-dihydro-1H-inden-1-ylamino)carbonyl]-2-thienyl}-2-[2-(4-fluorophenyl)ethyl]-5-oxo-7,8,9,9a-tetrahydro-5H-pyrido[2,3-a]pyrrolizine-3-carboxylate;

Ethyl(9aS)-4-(4-{[(3,4-difluorobenzyl)amino]carbonyl}-2-thienyl)-2-[2-(4-fluorophenyl)ethyl]-5-oxo-7,8,9,9a-tetrahydro-5H-pyrido[2,3-a]pyrrolizine-3-carboxylate;

Ethyl(9aS)-4-{4-[(2,3-dihydro-1H-inden-1-ylamino)carbonyl]-2-furyl}-2-[2-(4-fluorophenyl)ethyl]-5-oxo-7,8,9,9a-tetrahydro-5H-pyrido[2,3-a]pyrrolizine-3-carboxylate;

Ethyl(9aS)-4-(5-{[(1R)-2,3-dihydro-1H-inden-1-ylamino]carbonyl}-2-thienyl)-2-[2-(4-fluorophenyl)ethyl]-5-oxo-7,8,9,9a-tetrahydro-5H-pyrido[2,3-a]pyrrolizine-3-carboxylate;

Ethyl (9aS)-4-(5-{[(1R)-2,3-dihydro-1H-inden-1-ylamino]carbonyl}-1,3-thiazol-2-yl)-2-(4-fluorobenzyl)-5-oxo-7,8,9,9a-tetrahydro-5H-pyrido[2,3-a]pyrrolizine-3-carboxylate;

4-{(9aS)-2-(2,4-difluorobenzyl)-5-oxo-3-[(trifluoroacetyl)amino]-7,8,9,9a-tetrahydro-5H-pyrido[2,3-α]pyrrolizin-4-yl}-N-[(1R)-2,3-dihydro-1H-inden-1-yl]benzamide;

Ethyl (9aS)-4-[4-({[2-(1H-imidazol-5-yl)ethyl]amino}carbonyl)phenyl]-5-oxo-2-{2-[4-(trifluoromethyl)phenyl]ethyl}-7,8,9,9a-tetrahydro-5H-pyrido[2,3-α]pyrrolizine-3-carboxylate;

and

Ethyl (9aS)-4-(4-{[(1R)-2,3-dihydro-1H-inden-1-ylamino]carbonyl}phenyl)-2-(4-methylpentyl)-5-oxo-7,8,9,9a-tetrahydro-5H-pyrido[2,3-α]pyrrolizine-3-carboxylate.

Certain of the compounds described herein contain one or more chiral centers, or may otherwise be capable of existing as multiple stereoisomers. The scope of the present invention includes mixtures of stereoisomers as well as purified enantiomers or enantiomerically or diastereomerically enriched mixtures. Also included within the scope of the invention are the individual isomers of the compounds disclosed, as well as any wholly or partially equilibrated mixtures thereof. The present invention also covers the individual isomers of the compounds represented by the formulas herein as mixtures with isomers thereof in which one or more chiral centers are inverted. Nevertheless particular stereochemical configurations are preferred, namely, the S configuration, at the stereocenter when Y=C.

In another aspect of the present invention, the present invention includes compounds of formula (II):

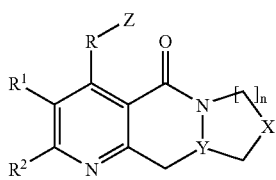

including salts, solvates, and pharmaceutically functional derivatives thereof, wherein R is aryl, heteroaryl, alkyl, or cycloalkyl,
further wherein said aryl, heteroaryl, alkyl, or cycloalkyl may be optionally substituted with one or more of alkyl, halogen, nitro, or trifluoromethyl;

Z is H, alkyl, halogen, C(O)OR$^5$, C(O)N(R$^5$)$_2$, C(O)NHN(R$^5$)$_2$, NHC(O)N(R$^5$)$_2$, S(O)$_2$N(R$^5$)$_2$, CH$_2$NHC(O)R$^5$, NO$_2$, N(R$^5$)$_2$, NHC(O)R$^5$, N(R$^5$)S(O)$_2$N(R$^5$)$_2$, OR$^5$, CH$_2$N(R$^5$)$_2$, CH$_2$C(O)N(R$^5$)$_2$, CH$_2$C(O)OR$^5$, heteroaryl, said heteroaryl optionally may be substituted with alkyl or aralkyl;

each occurrence of R$^5$ independently is H, alkyl, trifluoromethyl, aryl, heteroaryl, aralkyl, heteroaralkyl, cycloalkyl, heterocyclyl, fused cycloalkylaryl, or fused heterocyclylaryl,
further wherein said aryl, heteroaryl, aralkyl, heteroaralkyl, cycloalkyl, or heterocyclyl may be substituted with one or more halogen;

R$^1$ is H, alkyl, C(O)OR$^5$, C(O)R$^5$, CON(R$^5$)$_2$, CN, NO$_2$, N(R$^5$)$_2$, S(O)$_2$R$^5$, S(O)$_2$N(R$^5$)$_2$, NHC(O)R$^5$, NHC(O)N(R$^5$)$_2$,
further wherein R$^5$ is as defined above;

R$^2$ is alkyl, trifluoromethyl, alkoxy, aryl, heteroaryl, aralkyl, heteroaralkyl, or alkoxyaryl,
further wherein said alkyl, aryl, heteroaryl, aralkyl, and heteroaralkyl may be substituted with one or more of halogen, trifluoromethyl, or alkoxy;

Y is C or N;
X is S, O, N(R$^5$), C(R$^5$)$_2$, S(O)$_2$; and
n is 1, 2, 3, or 4.

R preferably is aryl. R more preferably is phenyl. Z preferably is —C(O)N(R$^5$)$_2$, wherein one R$^5$ is H and one R$^5$ is heteroaralkyl. The heteroaralkyl may be selected from

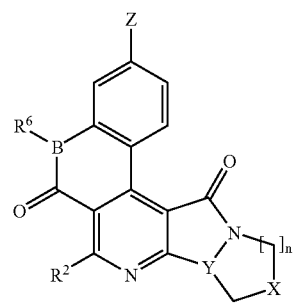

R$^1$ preferably is —C(O)OR$^5$, wherein R$^5$ is ethyl. R$^2$ preferably is aralkyl. R$^2$ preferably is aralkyl substituted with alkoxy. R$^2$ may be

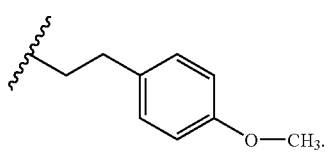

Preferably, Y is C. Preferably, X is —C(R$^5$)$_2$—, wherein each R$^5$ is H. Preferably n is 1.

Preferred compounds include ethyl (9aS)-2-[2-(4-methoxyphenyl)ethyl]-5-oxo-4-(4-{[(2-pyridinylmethyl)amino]carbonyl}phenyl)-5,7,8,9,9a,10-hexahydropyrrolo[1,2-g][1,6]naphthyridine-3-carboxylate.

Another embodiment of the present invention includes compounds of formula (III)

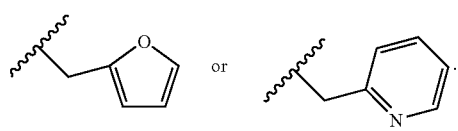

including salts, solvates, and pharmaceutically functional derivatives thereof, wherein Z is H, alkyl, halogen, C(O)OR$^5$, C(O)N(R$^5$)$_2$, C(O)NHN(R$^5$)$_2$, NHC(O)N(R$^5$)$_2$, S(O)$_2$N(R$^5$)$_2$, CH$_2$NHC(O)R$^5$, NO$_2$, N(R$^5$)$_2$, NHC(O)R$^5$, N(R$^5$)S(O)$_2$N(R$^5$)$_2$, OR$^5$, CH$_2$N(R$^5$)$_2$, CH$_2$C(O)N(R$^5$)$_2$, CH$_2$C(O)OR$^5$, heteroaryl, said heteroaryl optionally may be substituted with alkyl or aralkyl;

each occurrence of R$^5$ independently is H, alkyl, trifluoromethyl, aryl, heteroaryl, aralkyl, heteroaralkyl, cycloalkyl, heterocyclyl, fused cycloalkylaryl, or fused heterocyclylaryl,
further wherein said aryl, heteroaryl, aralkyl, heteroaralkyl, cycloalkyl, or heterocyclyl may be substituted with one or more halogen;

R$^2$ is alkyl, trifluoromethyl, alkoxy, aryl, heteroaryl, aralkyl, heteroaralkyl, or alkoxyaryl,
further wherein said alkyl, aryl, heteroaryl, aralkyl, and heteroaralkyl may be substituted with one or more of halogen, trifluoromethyl, or alkoxy;

B is C, N, or O, however, if B is O, then R$^6$ does not exist;
R$^6$ is H, alkyl, trifluoromethyl, aryl, heteroaryl, aralkyl, heteroaralkyl, cycloalkyl, or heterocyclyl, further wherein said aryl, heteroaryl, aralkyl, heteroaralkyl, cycloalkyl, or heterocyclyl may be substituted with one or more halogen;

Y is C or N;
X is S, O, N(R$^5$), C(R$^5$)$_2$, S(O)$_2$; and
n is 1, 2, 3, or 4.

Preferably, Z is —C(O)N(R$^5$)$_2$, wherein one R$^5$ is H and one R$^5$ is fused cycloalkylaryl. The fused cycloalkylaryl preferably is:

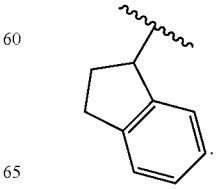

Preferably, R⁶ may be H. R² may be aralkyl. R² may be further substituted with one or more halogen. R² may be

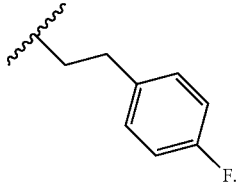

Preferably Y is C. Preferably B is N. Preferably, X is —C(R⁵)₂—, wherein each R⁵ is H. Preferably n is 1.

Preferred compounds include (8bS)-N-[(1R)-2,3-dihydro-1H-inden-1-yl]-7-[2-(4-fluorophenyl)ethyl]-6,13-dioxo-5,8b,9,10,11,13-hexahydro-6H-benzo[c]pyrrolizino[2,1-f][2,7]naphthyridine-3-carboxamide; and
(8bS)-N-[(1R)-2,3-dihydro-1H-inden-1-yl]-7-(4-fluorobenzyl)-6,13-dioxo-5,8b,9,10,11,13-hexahydro-6H-benzo[c]pyrrolizino[2,1-f][2,7]naphthyridine-3-carboxamide.

Another embodiment of the present invention includes preferred intermediates, namely, compounds of formula (IV)

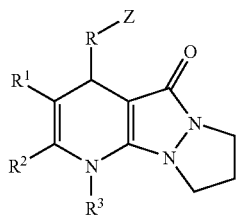

(IV)

including salts, solvates, and pharmaceutically functional derivatives thereof, wherein R is aryl, heteroaryl, alkyl, or cycloalkyl, Z is H, alkyl, halogen, C(O)OR⁵, C(O)N(R⁵)₂, C(O)NHN(R⁵)₂, NHC(O)N(R⁵)₂, S(O)₂N(R⁵)₂, CH₂NHC(O)R⁵, NO₂, N(R⁵)₂, NHC(O)R⁵, N(R⁵)S(O)₂N(R⁵)₂, OR⁵, CH₂N(R⁵)₂, CH₂C(O)N(R⁵)₂, CH₂C(O)OR⁵, heteroaryl, said heteroaryl optionally may be substituted with alkyl or aralkyl;

each occurrence of R⁵ independently is H, alkyl, trifluoromethyl, aryl, heteroaryl, aralkyl, heteroaralkyl, cycloalkyl, heterocyclyl, fused cycloalkylaryl, or fused heterocyclylaryl, further wherein said aryl, heteroaryl, aralkyl, heteroaralkyl, cycloalkyl, or heterocyclyl may be substituted with one or more halogen;

R¹ is H, alkyl, C(O)OR⁵, C(O)R⁵, CON(R⁵)₂, CN, NO₂, N(R⁵)₂, S(O)₂R⁵, S(O)₂N(R⁵)₂, NHC(O)R⁵, NHC(O)N(R⁵)₂, further wherein R⁵ is as defined above;

R² is alkyl, trifluoromethyl, alkoxy, aryl, heteroaryl, aralkyl, heteroaralkyl, or alkoxyaryl, further wherein said alkyl, aryl, heteroaryl, aralkyl, and heteroaralkyl may be substituted with one or more of halogen, trifluoromethyl, or alkoxy; and R³ is H, alkyl, aralkyl, or heteroaralkyl.

Preferably, R is aryl. More preferably R is phenyl. Preferably, Z is —C(O)N(R⁵)₂, wherein one R⁵ is H and one R⁵ is a fused cycloalkylaryl. More preferably the fused cycloalkylaryl is

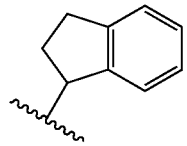

Preferably R¹ is —C(O)OR⁵, wherin R⁵ is ethyl. Preferably, R² is aralkyl substituted with one or more trifluoromethyl. More preferably, R² is

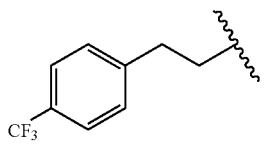

Preferably R³ is H.

Preferred compounds include:

Ethyl 4-(4-{[(1R)-2,3-dihydro-1H-inden-1-ylamino]carbonyl}phenyl)-5-oxo-2-{2-[4-(trifluoromethyl)phenyl]ethyl}-1,5,8,9-terahydro-4H,7H-pyrazolo[1',2':1,2]pyrazolo[3,4-b]pyridine-3-carboxylate;

Ethyl 4-(4-{[(1R)-2,3-dihydro-1H-inden-1-ylamino]carbonyl}phenyl)-2-(4-fluorobenzyl)-5-oxo-1,5,8,9-tetrahydro-4H, 7H-pyrazolo[1',2':1,2]pyrazolo[3,4-b]pyridine-3-carboxylate.

Another aspect of the present invention includes pharmaceutical compositions that include a compound of formula (I), (II), (III), (IV), or mixtures thereof. Such pharmaceutical compositions generally include a pharmaceutically acceptable carrier as will be described below in more detail.

Another aspect of the present invention includes use of the compounds of formula (I), (II), (III), (IV), or mixtures thereof as an active therapeutic substance.

Another aspect of the invention includes compounds of formula (I), (II), (III), (IV), or mixtures thereof for use in the treatment or prevention of diseases, disorders, or conditions mediated by calcitonin.

Another aspect of the invention includes compounds of formula (I), (II), (III), (IV), or mixtures thereof for use in the treatment and prevention of diseases and conditions characterized by abnormal calcification as well as in conditions wherein calcitonin would have a beneficial pharmacological effect. Such conditions and diseases include, without limitation: osteopenia and osteoporosis in men and women; reduction in the risk of fractures, both vertebral and nonvertebral; Paget's disease; bone fracture or deficiency; primary or secondary hyperparathyroidism; periodontal disease or defect; metastatic bone disorder; osteolytic bone disease; post-plastic surgery; post-prosthetic joint surgery; post-dental implantation; hypercalcemia; bone pain, general pain, and hyperalgesia; conditions associated with inhibiting gastric secretion; gastrointestinal disorders; osteoarthritis and rheumatoid arthritis (pain, bone loss, and joint destruction); renal osteodystrophy; obesity by induction of satiety; and male infertility.

Another aspect of the invention includes compounds of formula (I), (II), (III), (IV), or mixtures thereof for use as a calcitonin mimetic.

Another aspect of the invention includes use of the compounds of formula (I), (II), (III), (IV), or mixtures thereof in the manufacture of a medicament for use in the treatment of osteopenia and osteoporosis in men and women; reduction in the risk of fractures, both vertebral and nonvertebral; Paget's disease; bone fracture or deficiency; primary or secondary hyperparathyroidism; periodontal disease or defect; metastatic bone disorder; osteolytic bone disease; post-plastic surgery; post-prosthetic joint surgery; post-dental implantation; hypercalcemia; bone pain, general pain, and hyperalgesia; conditions associated with inhibiting gastric secretion; gastrointestinal disorders; osteoarthritis and rheumatoid arthritis (pain, bone loss, and joint destruction); renal osteodystrophy; obesity by induction of satiety; and male infertility.

Another aspect of the invention includes administering compounds of formula (I), (II), (III), (IV), or mixtures thereof to a mammal in need of a calcitonin mimetic. Thus, the present invention includes administering compounds of formula (I), (II), (III), (IV), or mixtures thereof for therapy of osteopenia and osteoporosis in men and women; reduction in the risk of fractures, both vertebral and nonvertebral; Paget's disease; bone fracture or deficiency; primary or secondary hyperparathyroidism; periodontal disease or defect; metastatic bone disorder; osteolytic bone disease; post-plastic surgery; post-prosthetic joint surgery; post-dental implantation; hypercalcemia; bone pain, general pain, and hyperalgesia; conditions associated with inhibiting gastric secretion; gastrointestinal disorders; osteoarthritis and rheumatoid arthritis (pain, bone loss, and joint destruction); renal osteodystrophy; obesity by induction of satiety; and male infertility.

Another aspect of the invention includes a method of osteopenia and osteoporosis in men and women; reduction in the risk of fractures, both vertebral and nonvertebral; Paget's disease; bone fracture or deficiency; primary or secondary hyperparathyroidism; periodontal disease or defect; metastatic bone disorder; osteolytic bone disease; post-plastic surgery; post-prosthetic joint surgery; post-dental implantation; hypercalcemia; bone pain, general pain, and hyperalgesia; conditions associated with inhibiting gastric secretion; gastrointestinal disorders; osteoarthritis and rheumatoid arthritis (pain, bone loss, and joint destruction); renal osteodystrophy; obesity by induction of satiety; and male infertility therapy through administration to a mammal in need thereof an effective amount of a compound of any of the compounds of formula (I), (II), (III), (IV), or mixtures thereof.

DETAILED DESCRIPTION OF THE PREFERRED EMBODIMENT

Several definitions are relevant to the present specification. For example, as used herein, the term "alkyl" refers to a straight or branched chain hydrocarbon that may be optionally substituted, with multiple degrees of substitution being allowed. Examples of "alkyl" include, but are not limited to methyl, ethyl, n-propyl, isopropyl, n-butyl, n-pentyl, isobutyl, isopropyl, and the like. The term "$C_1$–$C_6$ alkyl" or "lower alkyl" refers to an alkyl group, as defined above, containing at least 1 and at most 6 carbon atoms. Examples of branched or straight-chain "$C_1$–$C_6$ alkyl" groups include, but are not limited to methyl, ethyl, n-propyl, isopropyl, isobutyl, n-butyl, and t-butyl.

The term "alkylene" refers to a straight or branched chain unsaturated aliphatic hydrocarbon radical that may be optionally substituted, with multiple degrees of substitution being allowed. Examples of "alkylene" include, but are not limited to methylene, ethylene, n-propylene, n-butylene, and the like.

The term "halogen" refers to fluorine, chlorine, bromine, or iodine.

The term "cycloalkyl" refers to an optionally substituted non-aromatic cyclic hydrocarbon ring. Exemplary "cycloalkyl" groups include, but are not limited to cyclopropyl, cyclobutyl, cyclopentyl, cyclohexyl, cycloheptyl, and the like.

The term "heterocyclic" or the term "heterocyclyl" refers to a heterocyclic ring having one or more degrees of unsaturation containing one or more heteroatomic substitutions selected from S, S(O), S(O)$_2$, O, or N, that may be further optionally substituted, with multiple degrees of substitution being allowed. Such a ring may be optionally fused to one or more other "heterocyclic" ring(s) or cycloalkyl ring(s). Examples of "heterocyclic" moieties include, but are not limited to tetrahydrofuran, pyran, 1,4-dioxane, 1,3-dioxane, piperidine, pyrrolidine, morpholine, tetrahydrothiopyran, tetrahydrothiophene, and the like.

The term "aryl" refers to an optionally substituted benzene ring or to an optionally substituted benzene ring system fused to one or more optionally substituted benzene rings to form, for example, anthracene, phenanthrene, or naphthalene ring systems. Examples of "aryl" groups include, but are not limited to phenyl, 2-naphthyl, 1-naphthyl, biphenyl, as well as substituted derivatives thereof. The term "aralkyl" further refers to groups of —$R_aR_b$, where $R_a$ is an alkylene as defined herein and $R_b$ is an aryl as defined herein. Exemplary "aralkyl" groups include $C_{1-6}$alkylene-aryl, such as benzyl.

The term "heteroaryl" refers to a monocyclic aromatic ring system, or to a fused bicyclic aromatic ring system comprising two of aromatic rings. These heteroaryl rings contain one or more nitrogen, sulfur, and/or oxygen atoms, where N-oxides and sulfur oxides and dioxides are permissible heteroatom substitutions and may be optionally substituted, with multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof. The term "heteroaralkyl" further refers to groups of —$R_aR_b$, where $R_a$ is an alkylene as defined herein and $R_b$ is a heteroaryl as defined herein.

The term "alkoxy" refers to the group $R_aO$—, where $R_a$ is alkyl as defined above. The term "alkoxyaryl" refers to the group —$R_bR_aO$—, where $R_a$ is alkyl and $R_b$ is aryl as defined above.

The terms fused "cycloalkylaryl" and "heterocyclylaryl" refer to a group of —$R_aR_b$, where $R_a$ is a cycloalkyl or heterocycle, respectively, that is fused with $R_b$ which is defined as an aryl group. Examples of such groups include:

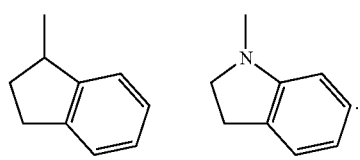

The compounds of the present invention as well as salts, solvates, and pharmaceutically functional derivatives thereof have the ability to crystallize in more than one form, a characteristic, which is known as polymorphism, and it is understood that such polymorphic forms ("polymorphs") are within the scope of formula (I), (II), (III), and (IV). Polymorphism generally can occur as a response to changes in temperature or pressure or both and can also result from variations in the crystallization process. Polymorphs can be distinguished by various physical characteristics known in the art, such as x-ray diffraction patterns, solubility, and melting point.

As noted above, certain of the compounds described herein contain one or more chiral atoms, or may otherwise be capable of existing in enantiomeric and diastereomeric forms. The scope of the present invention is intended to cover all isomers per se, as well as mixtures of cis and trans isomers, mixtures of diastereomers, and racemic mixtures of enantiomers. Also included within the scope of the invention are the individual isomers of the compounds represented by formulas (I), (II), (III), or (IV) above as well as any wholly or partially equilibrated mixtures thereof. The present invention also covers the individual isomers of the compounds represented by the formulas above as mixtures with isomers thereof in which one or more chiral centers are inverted.

As noted above, the present invention includes salts, solvates, and pharmaceutically functional derivatives of the compounds of the present invention. Salts include addition salts, metal salts, or optionally alkylated ammonium salts. Examples of such salts include hydrochloric, hydrobromic, hydroiodic, phosphoric, sulftric, trifluoroacetic, trichloroacetic, oxalic, maleic, pyruvic, malonic, succinic, citric, mandelic, benzoic, cinnamic, methane sulphonic, ethane sulphonic, picric, and the like. Further salts include lithium, sodium, potassium, magnesium, and the like. Reference is also made to *Journal of Pharmaceutical Science*, 1997, 66, 2, incorporated herein by reference as relevant to salts.

The term "pharmaceutically functional derivative" refers to any pharmaceutically acceptable derivative of a compound of the present invention, for example, an ester or an amide, which upon administration to a manmal is capable of providing (directly or indirectly) a compound of the present invention or an active metabolite thereof. Such derivatives are recognizable to those skilled in the art, without undue experimentation. Nevertheless reference is made to the teaching of *Burger's Medicinal Chemistry and Drug Discovery*, 5$^{th}$ Edition, Vol 1: Principles and Practice, which is incorporated herein by reference to the extent of teaching pharmaceutically functional derivatives.

As used herein, the term "solvate" refers to a complex of variable stoichiometry formed by a solute (in this invention, a compound of formula (I), (II), (III), or (IV) or a salt or pharmaceutically functional derivative thereof and a solvent. Such solvents for the purpose of the invention should not interfere with the biological activity of the solute. Examples of solvents include, but are not limited to water, methanol, ethanol, and acetic acid. Preferably the solvent used is a pharmaceutically acceptable solvent. Examples of pharmaceutically acceptable solvents include water, ethanol, and acetic acid.

While it is possible that compounds of the present invention may be administered as the raw chemical, preferably the compounds of the present invention are presented as an active ingredient within a pharmaceutical formulation, as are known in the art. Accordingly, the present invention further includes a pharmaceutical formulation comprising a compound of formula (I), (II), (III), or (IV), or salt, solvate, or functional derivative thereof together with one or more pharmaceutically acceptable carriers. Optionally, other therapeutic and/or prophylactic ingredients may be included in the pharmaceutical formulation. For example, the compounds of the present invention may be combined with other agents useful in the treatment or prophylaxis of osteoporosis, such as calcium, PTH, Vitamin D, estrogen, SERMs, bisphosphonates, and the like.

Formulations of the present invention include those especially formulated for oral, buccal, parental, transdermal, inhalation, intranasal, transmucosal, implant, or rectal administration. Among the variety of administrations, oral administration typically is preferred. For oral administration tablets, capsules, and caplets may contain conventional excipients such as binding agents, fillers, lubricants, disintegrants, and/or wetting agents. Non-limiting examples of binding agents include syrup, acacia, gelatin, sorbitol, tragacanth, mucilage of starch, or polyvinylpyrrolidone (PVP). Non-limiting examples of fillers include, for example, lactose, sugar, microcrystalline cellulose, maize-starch, calcium phosphate or sorbitol. Non-limiting examples of lubricants include, for example, magnesium sterate, stearic acid, talc, polyethylene glycol or silica. Non-limiting examples of disintegrants include, for example, potato starch or sodium starch glycollate. A non-limiting example of a wetting agent includes sodium lauryl sulfate. The tablets additionally may be coated according to methods known in the art.

Alternatively, the compounds of the present invention may be incorporated into oral liquid preparations such as aqueous or oily suspensions, solutions, emulsions, syrups, or elixirs. Moreover, formulations containing these compounds may be presented as a dry product for constitution with water or other suitable vehicle before use. Liquid preparations may contain conventional additives. Non-limiting examples of such additives include suspending agents such as sorbitol syrup, methyl cellulose, glucose/sugar syrup, gelatin, hydroxyethylcellulose, carboxymethyl cellulose, aluminum sterate gel or hydrogenated edible fats. Additionally, emulsifying agents such as lecithin, sorbitan monooleate or acacia; non-aqueous vehicles (which may include edible oils) such as almond oil, fractionated coconut oil, oily esters, propylene glycol or ethyl alcohol my be included. Further, preservatives such as methyl or propyl p-hydroxybenzoates or sorbic acid, may be incorporated into the preparation. Such preparations may also be formulated as suppositories, for example, containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, for example, sterile, pyrogen-free water, before use.

The formulations according to the invention may also be formulated as a depot preparation. Such long acting formulations may be administered by implantation, for example, subcutaneously or intramuscularly, or by intramuscular injection. Accordingly, the compounds of the invention may be formulated with suitable polymeric or hydrophobic materials, such as an emulsion in an acceptable oil, ion exchange resins, or as sparingly soluble derivatives, such as a sparingly soluble salt.

Pharmaceutical formulations may be presented in unit dose forms containing a predetermined amount of active ingredient per unit dose. Such a unit may contain certain amounts of a compound of formula (I), (II), (III), or (IV) depending on the condition being treated, the route of administration, and the age, weight and condition of the patient. Preferred unit dosage formulations are those containing a predetermined dose, such as a daily dose, or an appropriate fraction thereof, of an active ingredient. Such pharmaceutical formulations may be prepared by any of the methods well known in the pharmacy art.

A "therapeutically effective amount" of a compound of the present invention will depend upon a number of factors including, for example, the age and weight of the animal, the precise condition requiring treatment and its severity, the nature of the formulation, and the route of administration. Therapeutic effectiveness ultimately will be at the discretion of the attendant physician or veterinarian. An effective amount of a salt or solvate, or pharmaceutically functional derivative thereof, may be determined as a proportion of the effective amount of the compound of formula (I), (II), (III), or (IV) per se.

Experimentals

The following examples illustrate aspects of this invention, but should not be construed as limitations. The symbols and conventions used in these examples are consistent with those used in the contemporary chemical literature, for example, the *Journal of the American Chemical Society*.

Formula I

Compounds of formula I, shown in Scheme 1 below, were synthesized using an extension of the Hantzsch dihydropyridine synthesis. The unsymmetrical 1,4-dihydropyridines can be produced by conducting the Hantzsch synthesis in two stages (ref Satoh, Y., Ichihashi, M., and Okumura, K., *Chem. Pharm. Bull.*, 1992, 40, 912), but one pot. In a typical one-pot procedure the N-Boc-L-proline beta ketoester, enamine (made from the corresponding beta ketoester), 0.5 eq piperidine, and an aldehyde containing a suitable functional group (usually a carboxylic acid) are refluxed in benzene or toluene under Dean-Stark conditions for 1–2 h. The dihydropyridine product D can be chromatographed easily at this time or may be subjected directly to oxidation conditions using ceric ammonium nitrate to reveal the pyridine intermediate E. The Boc protecting group is then removed under acidic conditions and the subsequent amine is cyclized under basic conditions to give the pyridopyrrolizidinone skeleton. This product is preferably chromatographed at this step and then subjected to amide coupling conditions through the aldehyde's carboxylic acid. Through chromatography or recrystallization one obtains the title compound (Scheme 1G).

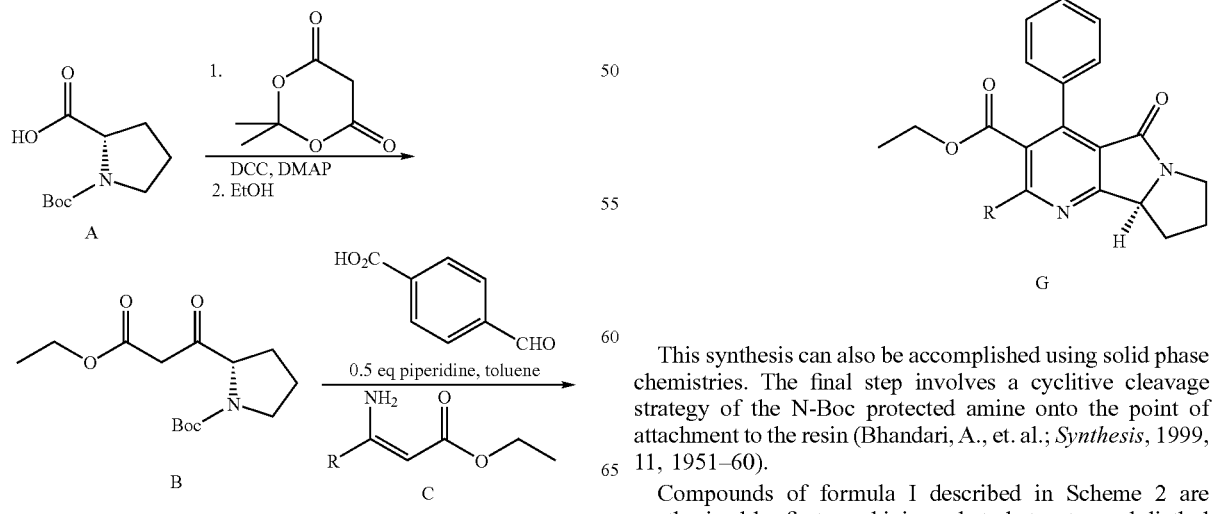

This synthesis can also be accomplished using solid phase chemistries. The final step involves a cyclitive cleavage strategy of the N-Boc protected amine onto the point of attachment to the resin (Bhandari, A., et. al.; *Synthesis*, 1999, 11, 1951–60).

Compounds of formula I described in Scheme 2 are synthesized by first combining a beta ketoester and diethyl 3-oxoglutarate to form the phenol (D) and then further elaborated to the triflate (F) as illustrated below. Palladium cross-coupling of an appropriately substituted aryl boronic acid followed by debenzylation under catalytic hydrogenation conditions gives the corresponding carboxylic acid. Amide coupling followed by chromatography of the crude material gives the desired final product(s).

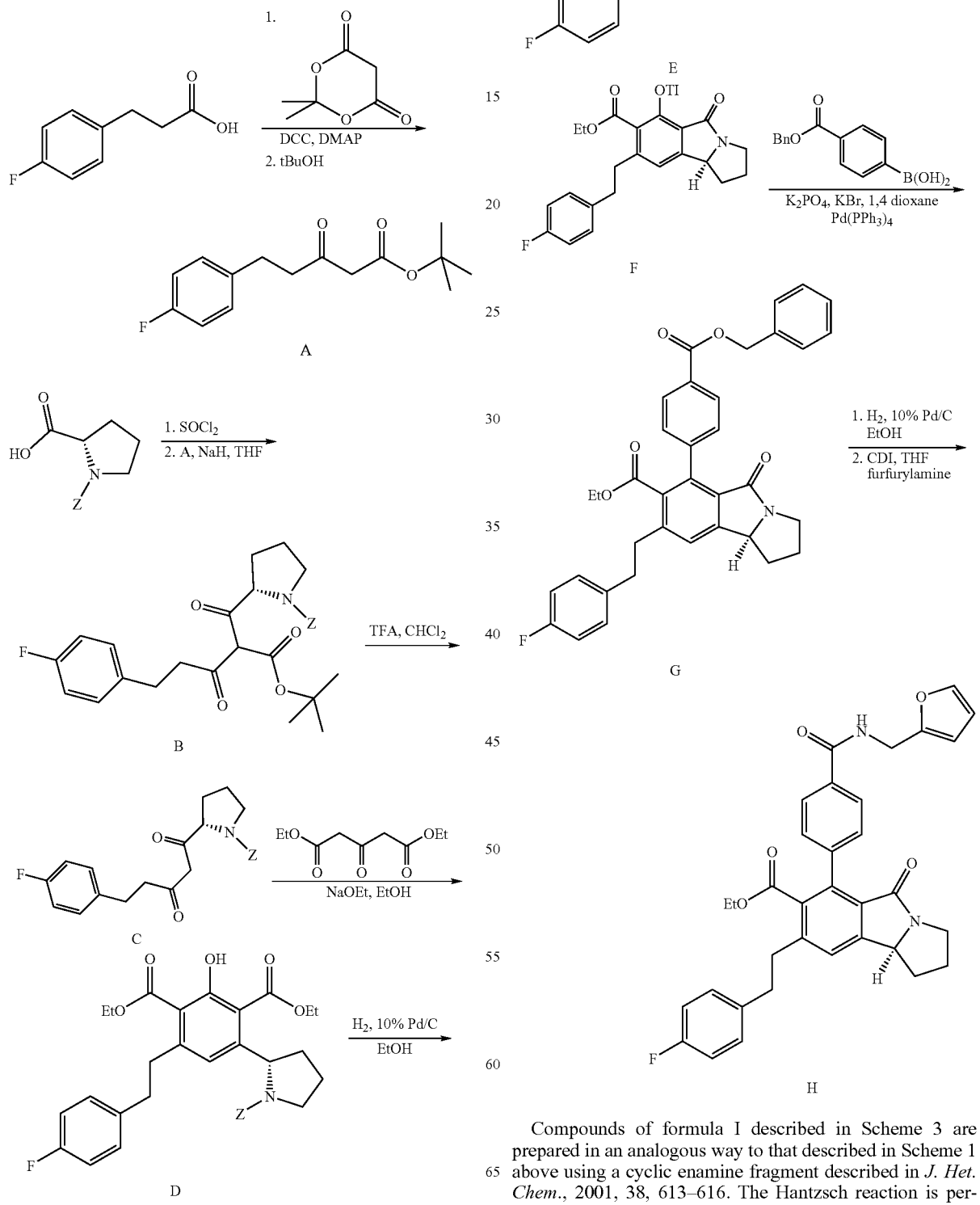

Compounds of formula I described in Scheme 3 are prepared in an analogous way to that described in Scheme 1 above using a cyclic enamine fragment described in *J. Het. Chem.*, 2001, 38, 613–616. The Hantzsch reaction is performed in one pot, combining a beta-ketoester, an aldehyde, and the enamine under basic conditions to form the dihydropyridine. Oxidation with ceric ammonium nitrate followed by an amide coupling gives the desired material after column chromatography on silica.

Scheme 3

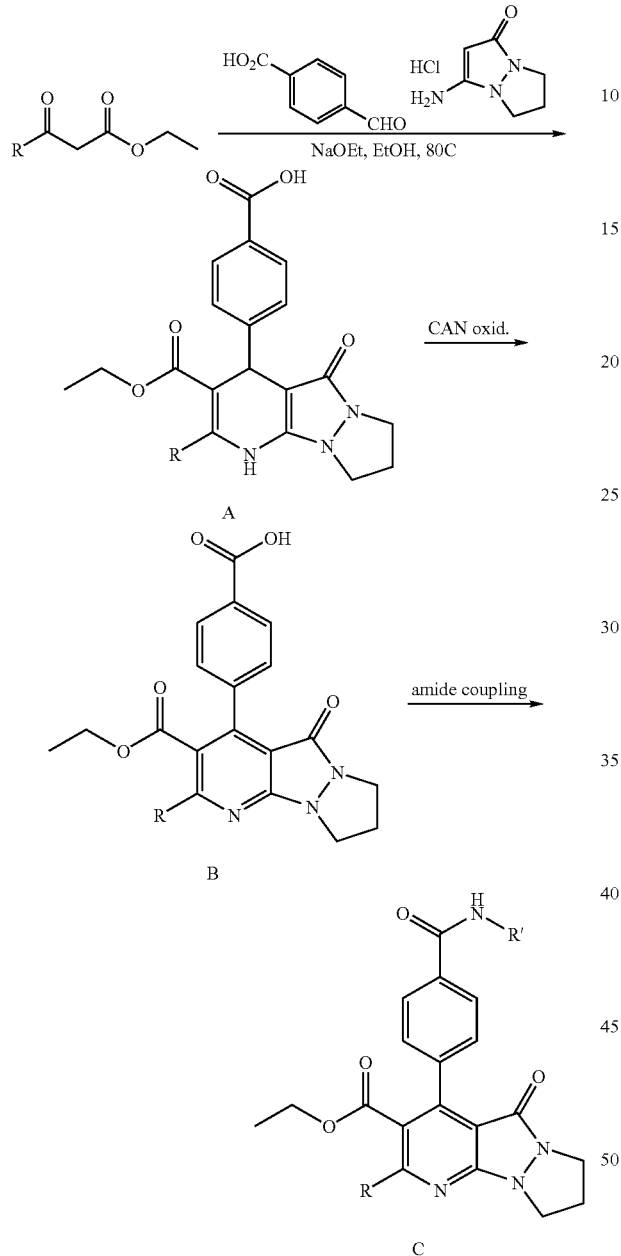

Formula II

Compounds of Formula II may be synthesized in a manner analogous to that described for Formula I, Scheme 1 using the homologated N-Boc-L-proline beta ketoester shown below to obtain the desired 6-6-5 ring system.

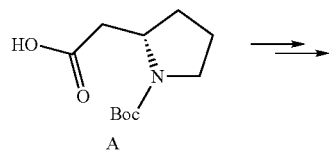

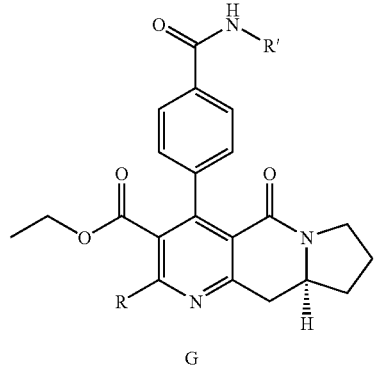

Formula III

Compounds of Formula III are synthesized in a similar manner to that described in Formula I, Scheme 1 through the use of an o-nitro substituted aryl aldehyde. Following the deprotection, cyclization and amide coupling, subsequent reduction of F and ring closure affords the pentacylcic ring system.

Scheme 4

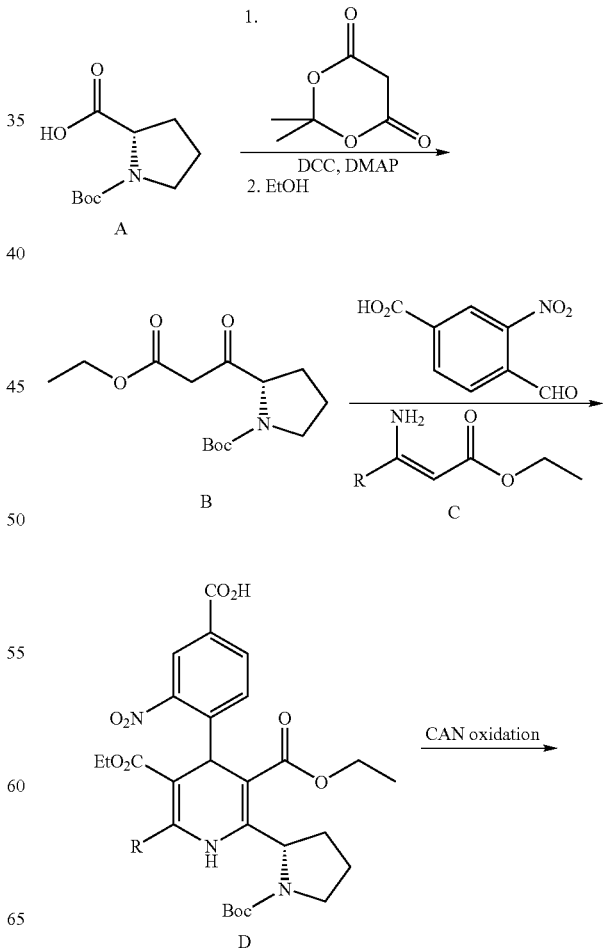

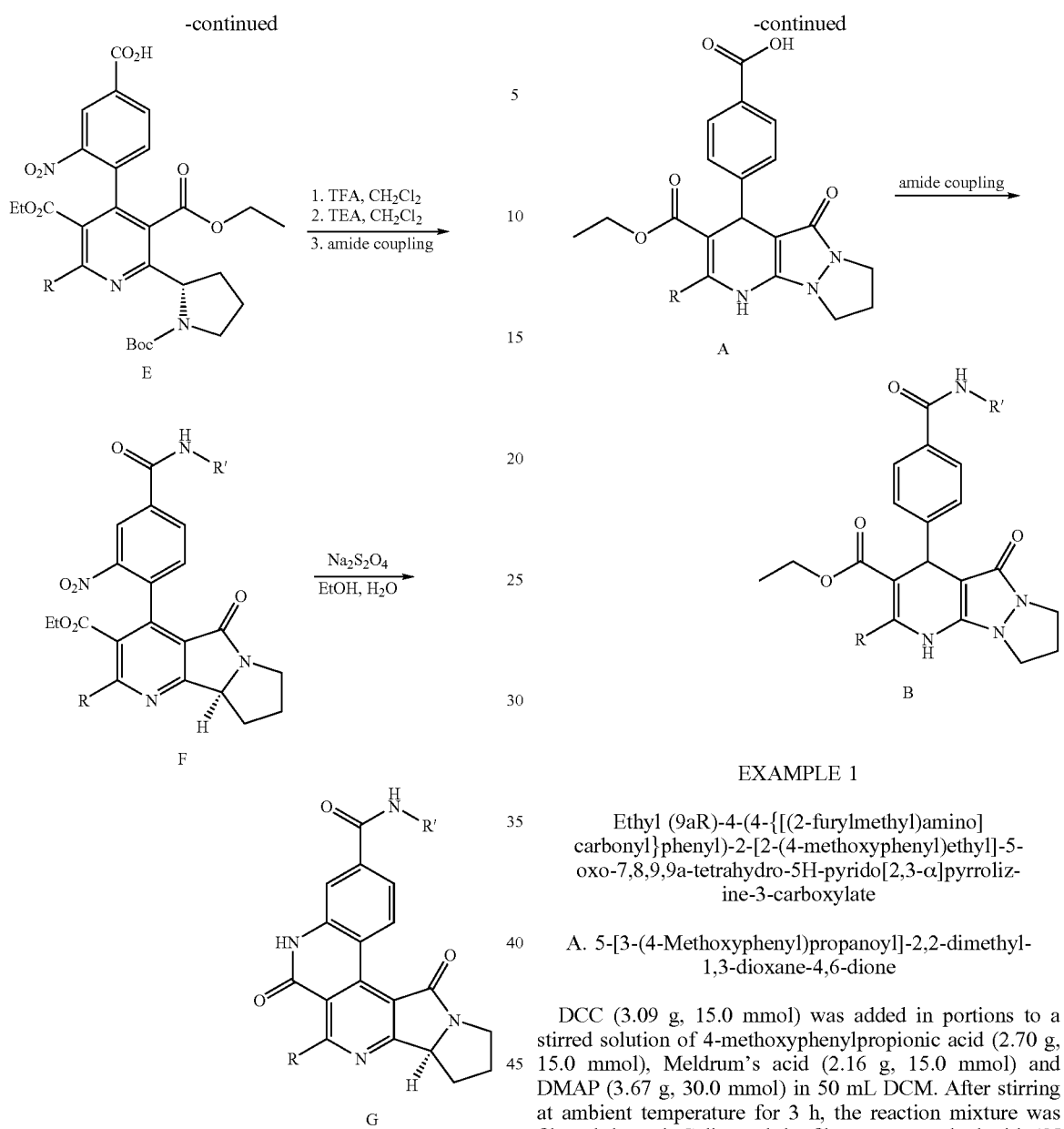

Formula IV

Compounds of Formula IV are synthesized in an analogous manner to that shown for Formula I, Scheme 3. Following the one-pot Hantzsch reaction, the dihydropyridines are directly subjected to an amide coupling followed by purification on silica gel to arrive at the final products.

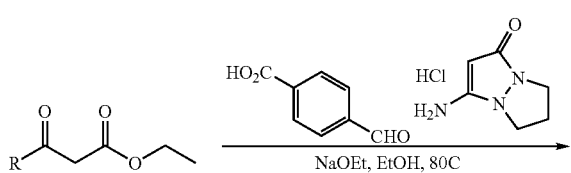

EXAMPLE 1

Ethyl (9aR)-4-(4-{[(2-furylmethyl)amino]carbonyl}phenyl)-2-[2-(4-methoxyphenyl)ethyl]-5-oxo-7,8,9,9a-tetrahydro-5H-pyrido[2,3-α]pyrrolizine-3-carboxylate

A. 5-[3-(4-Methoxyphenyl)propanoyl]-2,2-dimethyl-1,3-dioxane-4,6-dione

DCC (3.09 g, 15.0 mmol) was added in portions to a stirred solution of 4-methoxyphenylpropionic acid (2.70 g, 15.0 mmol), Meldrum's acid (2.16 g, 15.0 mmol) and DMAP (3.67 g, 30.0 mmol) in 50 mL DCM. After stirring at ambient temperature for 3 h, the reaction mixture was filtered through Celite and the filtrate was washed with 1N HCl (2×), water and brine and dried over $MgSO_4$. Filtration and concentration provided the acyl Meldrum's acid derivative as a tan solid (3.56 g, 11.6 mmol, 77.5%). $^1H$ NMR (400 MHz, $CDCl_3$) δ 7.17 (d, J=8.8 Hz, 2H), 7.83 (d, J=8.8 Hz, 2H), 3.78 (s, 3H), 3.37 (t, J=8.0 Hz, 2H), 2.96 (t, J=8.0 Hz, 2H), 1.78 (s, 6H) ppm.

B. Ethyl (2Z)-3-amino-5-(4-methoxyphenyl)-2-pentenoate

5-[3-(4-Methoxyphenyl)propanoyl]-2,2-dimethyl-1,3-dioxane-4,6-dione (1.5 g, 4.9 mmol) was refluxed in 20 mL absolute EtOH for 3 h. Concentration provided the β-keto ester as a clear oil which was immediately dissolved in 30 mL toluene and refluxed with $NH_4OAc$ (1.9 g, 25 mmol) in a Dean-Stark apparatus. After 14 h, the reaction mixture was allowed to cool. The toluene was removed by vacuum distillation and the resulting material was taken up in ether and washed with water (3×), brine and dried over $MgSO_4$.

Filtration and concentration provided the title compound as a semisolid gum (1.1 g, 4.9 mmol). $^1$H NMR (400 MHz, CDCl$_3$) δ 7.11 (d, J=8.4 Hz, 2H), 6.84 (d, J=6.8 Hz, 2H), 4.57 (bs, 1H), 4.11 (q, J=7.2 Hz, 2H), 3.78 (s, 3H), 2.81 (t, J=7.6 Hz, 2H), 2.39 (t, J=7.6 Hz, 2H), 1.26 (t, J=6.8 Hz, 3H) ppm.

C. tert-Butyl (2S)-2-[(2,2-dimethyl-4,6-dioxo-1,3-dioxan-5-yl)carbonyl]-1-pyrrolidinecarboxylate DCC (15.5 g, 75.0 mmol) was added in portions to a stirred solution of N-Boc-L-proline (16.1 g, 75.0 mmol), Meldrum's acid (10.8 g, 75.0 mmol) and DMAP (18.3 g, 150. mmol) in 200 mL DCM. After stirring at ambient temperature for 48 h, the reaction mixture was filtered through Celite and the filtrate was washed with 1N HCl (2×), water and brine and dried over MgSO$_4$. Filtration and concentration provided the acyl Meldrum's acid derivative as a yellow foam (30.3 g, 88.8 mmol).
$^1$H NMR (400 MHz, CDCl$_3$, mixture of rotamers) δ 5.55 (m, 1H), 3.56 (m, 2H), 2.55 (m, 1H), 2.0–1.8 (m, 3H), 1.8–1.7 (m, 6H), 1.44 (s, 4.5H), 1.36 (s, 4.5H) ppm.

D. Polymer-bound tert-butyl (3-oxopropanoyl)-1-pyrrolidinecarboxylate

ArgoGel-OH (45 g, 0.49 meq/g, 22 mmol) was suspended in toluene (400 mL) and tert-butyl (2S)-2-[(2,2-dimethyl-4,6-dioxo-1,3-dioxan-5-yl)carbonyl]-1-pyrrolidinecarboxylate (60. g, 176 mmol) was added. The sealed reaction tube was heated at 80° C. for 23 h. The reaction mixture was allowed to cool to room temperature and filtered. The resin was washed (DMF then DCM then ether; 8× each) then dried at 40° C. overnight under high vacuum (63 g; 0.44 meq/g).
E. Polymer-bound tert-butyl (3-oxopropanoyl)-1-pyrrolidinecarboxylate (0.5 g, 0.25 meq/g, 0.44 mmol) was suspended in 5 mL anhydrous DMF and 4-formylbenzoic 0.75 g, 4.9 mmol) was added followed by piperidine (0.1 mL), and trimethyl orthoformate (0.32 mL). After 5 h at 65° C., the resin was filtered and washed as above and resuspended in 5 mL fresh DMF. Ethyl (2Z)-3-amino-5-(4-methoxyphenyl)-2-pentenoate (0.60 g, 2.5 mmol) was added followed by trimethyl orthoformate (0.32 mL) and the sealed reaction mixture was heated at 80° C. for 16 h. The resin was filtered and washed as before. The resin was suspended in dimethylacetamide (5 mL) and ceric ammonium nitrate (0.65 g, 1.2 mmol) was added. The orange suspension was shaken at room temperature for 30 min then filtered and washed as before. The resin was dried overnight at 30° C. under high vacuum. The resin was suspended in 3 mL DMF and 1 mL pyridine. Pentafluorophenyl trifluoroacetate (0.61 g, 2.2 mmol, 0.4 mL) was added and the sealed reaction tube was shaken at room temperature for 45 min, filtered and washed as above and dried under high vacuum overnight. Half of the resin was suspended in DCM (2.5 mL) and DMAP (25 mg) and 2-furfurylamine (0.107 g, 1.1 mmol, 0.12 mL) were added and the reaction mixture was shaken at room temperature for 4 h. The resin was filtered and washed as before. The resin was suspended in 1 mL TFA:DCM:phenol: thioanisole (70:20:5:5) and shaken for 3 h, filtered and washed. The resin was shaken in 2 mL 5% TEA in DCM for 36 h. The resin was filtered into a collection flask and rinsed with additional DCM (3×). The filtrate was concentrated and the product was purified by preparative thin-layer chromatography (SiO$_2$, EtOAc) to give the title compound as white solid (6.3 mg, 0.010 mmol, 74%): mp=136—136° C. $^1$H NMR (400 MHz, CDCl$_3$) δ 7.83 (d, J=8.4 Hz, 2H), 7.46 (d, J=8.4 Hz, 2H), 7.39 (d, J=1.3 Hz, 1H), 7.14 (d, J=8.6 Hz, 2H), 6.83 (d, J=8.6 Hz, 2H), 6.48 (t, J=5.3 Hz, 1H), 6.36 (d, J=3.1 Hz, 1H), 6.31 (d, J=3.1 Hz, 1H), 4.74 (dd, J=10.4, 6.2 Hz, 1H), 4.65 (d, J=5.3, 2H), 4.02 (m, 2H), 3.79 (s, 3H), 3.71 (m, 1H), 3.38 (m, 1H), 3.18 (m, 2H), 3.06 (m, 2H), 4.50 (m, 1H), 2.33 (m, 2H), 1.39 (m, 1H), 0.94 (t, J=7.2 Hz, 3H) ppm. ESMS m/z 580 (MH)$^+$. Anal. calcd. For $C_{34}H_{33}N_3O_6 \cdot \frac{1}{2}C_6H_{14}$: C, 71.36; H, 6.47; N, 6.75. Found: C, 71.01; H, 6.37; N, 6.56.

EXAMPLE 2

Ethyl (9aS)-4-(4-{[(2-furylmethyl)amino]sulfonyl}phenyl)-5-oxo-2-{2-[4-(trifluoromethyl)phenyl]ethyl}-7,8,9,9a-tetrahydro-5H-pyrido[2,3-a]pyrrolizine-3-carboxylate A 2,2-Dimethyl-5-{3-[4-(trifluoromethyl)phenyl]propanoyl}-1,3-dioxane-4,6-dione.

DCC (41.3 g, 200. mmol) was added in portions to a stirred 0° C. solution of 3-(4-trifluoromethylphenyl)propionic acid (43.6 g, 200. mmol), Meldrum's acid (28.8 g, 200. mmol) and DMAP (24.4 g, 200. mmol) in 500 mL DCM. After stirring at 0° C. for 1.75 h, the reaction mixture was filtered through Celite, the filtrate was washed with 1N HCl (2×), water and brine and dried over MgSO$_4$. Filtration and concentration provided the acyl Meldrum's acid derivative as a yellow solid: $^1$H NMR (400 MHz, CDCl$_3$) δ 7.52 (d, J=8.1 Hz, 2H), 7.35 (d, J=8.1 Hz, 2H), 3.39 (t, J=7.6 Hz, 2H), 3.05 (t, J=7.6 Hz, 2H), 1.63 (s, 6H) ppm.

B. Ethyl 3-oxo-5-[4-(trifluoromethyl)phenyl]pentanoate 2,2-Dimethyl-5-{3-[4-(trifluoromethyl)phenyl]propanoyl}-1,3-dioxane-4,6-dione (200 mmol) was dissolved in 500 mL absolute EtOH and refluxed for 3 h. Concentration provided the title compound as a pale yellow oil (57.35 g, 199 mmol, 99.5%, two steps): $^1$H NMR (400 MHz, CDCl$_3$) δ 7.52 (d, J=8.0 Hz, 2H), 7.29 (d, J=8.0 Hz, 2H), 4.15 (m, 2H), 3.42 (s, 2H), 2.96 (m, 2H), 2.90 (m, 2H), 1.24 (t, J=7.1 Hz, 3H) ppm.

C. Ethyl (2Z)-3-amino-5-[4-(trifluoromethyl)phenyl]-2-pentenoate

Ethyl 3-oxo-5-[4-(trifluoromethyl)phenyl]pentanoate (57.5 g, 199 mmol) was dissolved in 300 mL benzene and NH$_4$OAc (77.1 g, 1 mol) was added. The suspension was refluxed in a Dean-Stark apparatus for 2 h. The cooled reaction mixture was diluted with ether and washed with 1N HCl (2×), water (2×) and brine and dried over Na$_2$SO$_4$. Filtration and concentration provided the enamine as a yellow oil (56.3 g, 196 mmol): $^1$H NMR (400 MHz, CDCl$_3$) δ 7.52 (d, J=8.1 Hz, 2H), 7.27 (d, J=8.1 Hz, 2H), 4.54 (s, 1H), 4.08 (q, J=7.0 Hz, 2H), 2.90 (t, J=7.9 Hz, 2H), 2.40 (d, J=7.9 Hz, 2H), 1.23 (t, J=7.0 Hz, 3H) ppm.

D. 4-Cyano-N-(2-furylmethyl)benzenesulfonamide

4-Cyanobenzenesulfonyl chloride (1.77 g, 8.78 mmol) was dissolved in 8 mL of anhydrous pyridine and 2-furfurylamine (1.04 g, 9.66 mmol, 0.98 mL) was added. After 2 h, the reaction solutions were added to 100 mL cold water and stirred for 10 min. Filtration and washing with water provided the title compound as a yellow solid (2.04 g, 7.78 mmol, 89%). $^1$H NMR (300 MHz, CDCl$_3$) δ 7.90 (d, J=8.4 Hz, 2H), 7.75 (d, J=8.4 Hz, 2H), 7.18 (s, 1H), 6.19 (m, 1H), 6.10 (m, 1H), 4.95 (m, 1H), 4.28 (d, J=6.0 Hz, 2H) ppm.

E. 4-Formyl-N-(2-furylmethyl)benzenesulfonamide

4-Cyano-N-(2-furylmethyl)benzenesulfonyl chloride (2.04 g, 7.78 mmol) was dissolved in 20 mL DCM and cooled to 0° C. and DIBAL (10.6 mL, 15.9 mmol, 1.5 M in toluene) was added dropwise over 5 min. The reaction mixture was allowed to warm to room temperature with stirring over 60 min. After cooling to 0° C., the reaction was quenched by the cautious addition of 1 N HCl (25 mL). After stirring for 10 min, the reaction mixture was partitioned between ether and 1 N HCl. The aqueous layer was extracted with ether (2×) and the combined ether layers were dried over Mg SO$_4$, filtered and concentrated to provide the aldehyde as a white glass (1.95 g, 7.36 mmol, 95%). $^1$H NMR (300 MHz, CDCl$_3$) 10.08 (s, 1H), 7.96 (s, 4H), 7.17 (m, 1H), 6.17 (m, 1H), 6.09 (m, 1H), 5.07 (m, 1H), 4.26 (d, J=5.8 Hz, 2H) ppm.

F. Polymer-bound tert-butyl (3-oxopropanoyl)-1-pyrrolidinecarboxylate (0.70 g, 0.31 meq/g, 0.44 mmol) was suspended in 5 mL anhydrous DMF and 4-formyl-N-(2-furylmethyl)benzenesulfonamide (0.82 g, 3.1 mmol) was added followed by piperidine (0.06 mL), and trimethyl orthoformate (0.2 mL) and AcOH (0.04 mL). After 14 h at 65° C., the resin was filtered and washed as above and resuspended in 5 mL fresh DMF. Ethyl (2Z)-3-amino-5-[4-(trifluoromethyl)phenyl]-2-pentenoate (0.89 g, 3.1 mmol) was added followed by trimethyl orthoformate (0.2 mL) and the sealed reaction mixture was heated at 80° C. for 16 h. The resin was filtered and washed as before. The resin was suspended in DCM (8 mL) and DDQ (0.17 g, 0.77 mmol) was added. The brown suspension was shaken at room temperature for 30 min then filtered and washed as before. The resin was dried overnight at 30° C. under high vacuum. The resin was suspended in 1 mL TFA:DCM:phenol:thioanisole (70:20:5:5) and shaken for 0.5 h, filtered and washed. The resin was shaken in 2 mL 5% TEA in DCM for 24 h. The resin was filtered into a collection flask and rinsed with additional DCM (3×). The filtrate was concentrated and the product was purified by preparative column chromatography (SiO$_2$, hexanes:EtOAc 2:3) then triturated in ether to provide the title compound as white solid (21 mg, 0.032 mmol, 100%): mp=181–182° C. $^1$H NMR (400 MHz, CDCl$_3$) δ 7.88 (d, J=8.4 Hz, 2H), 7.54 (d, J=8.0 Hz, 2H), 7.51 (d, J=8.4 Hz, 2H), 7.33 (d, J=8.4 Hz, 2H), 7.30 (m, 1H), 6.24 (m, 1H), 6.16 (m, 1H), 4.84 (t, J=6.0 Hz, 1H), 4.74 (dd, J=10.2, 6.4 Hz, 1H), 4.24 (d, J=6.0 Hz, 2H), 4.01 (q, J=7.0 Hz, 2H), 3.71 (m, 1H), 3.40 (m, 1H), 3.3–3.1 (m, 4H), 2.49 (m, 1H), 2.37 (m, 2H), 1.5–1.3 (m, 1H), 0.92 (t, J=7.0 Hz, 3H) ppm. ESMS m/z 654 (M+H)$^+$. Anal. calcd. For C$_{33}$H$_{30}$F$_3$N$_3$O$_6$S: C, 60.64; H, 4.63; N, 6.43; S, 4.91; found: C, 60.41; H, 4.63; N, 6.43; S, 4.99.

EXAMPLE 3

Ethyl (9aS)-4-{2-[(benzylamino)carbonyl]cyclopropyl}-5-oxo-2-{2-[4-(trifluoromethyl)phenyl]ethyl}-7,8,9,9a-tetrahydro-5H-pyrido[2,3-a]pyrrolizine-3-carboxylate A. 2-Formylcyclopropanecarboxylic acid Ethyl 2-formylcyclopropanecarboxylate (0.92 g, 6.5 mmol) was dissolved in 10 mL 50% aqueous MeOH. Potassium carbonate (1.3 g, 9.2 mmol) was added and the reaction mixture was allowed to stand at room temperature for 14 h. The reaction mixture was poured into brine and extracted with ether (2×). The aqueous layer was acidified with 6 N HCl to pH 1 and continuously extracted overnight with DCM. Concentration provided the acid as a white glass (0.50 g, 4.4 mmol, 67%). $^1$H NMR (400 MHz, CDCl$_3$) δ 9.34 (d, J=3.9 Hz, 1H), 2.50 (m, 1H), 2.68 (m, 1H), 1.64 (m, 1H), 1.58 (m, 1H) ppm.

B. ArgoGel-OH (0.50 g, 0.44 meq/g, 0.22 mmol) was suspended in toluene (5 mL) tert-butyl (2S)-2-[(2,2-dimethyl-4,6-dioxo-1,3-dioxan-5-yl)carbonyl]-1-pyrrolidinecarboxylate (0.85 g, 0.25 mmol) was added. The sealed reaction tube was heated at 80° C. for 23 h. The reaction mixture was allowed to cool to room temperature and filtered. The resin was washed (DMF then DCM then ether; 8× each) and suspended in 5 mL anhydrous DMF and 2-formylcyclopropanecarboxylic acid (0.25 g, 2.2 mmol) was added followed by piperidine (0.04 mL), and trimethyl orthoformate (0.15 mL). After 14 h at 65° C., the resin was filtered and washed as above and resuspended in 5 mL fresh DMF. Ethyl (2Z)-3-amino-5-[4-(trifluoromethyl)phenyl]-2-pentenoate (0.63 g, 2.2 mmol) was added followed by trimethyl orthoformate (0.15 mL) and the sealed reaction mixture was heated at 80° C. for 16 h. The resin was filtered and washed as before. The resin was suspended in DCM (5 mL) and DDQ (0.13 g, 0.55 mmol) was added. The brown suspension was shaken at room temperature for 30 min then filtered and washed as before. The resin was dried overnight at 30° C. under high vacuum. The resin (0.15 g, 0.05 mmol) was suspended in 2 mL DMF and 0.5 mL pyridine. Pentafluorophenyl trifluoroacetate (0.13 g, 0.5 mmol, 0.08 mL) was added and the sealed reaction tube was shaken at room temperature for 45 min, filtered and washed as above and dried under high vacuum overnight. The resin was suspended in DCM (2 mL) and DMAP (25 mg) and benzylamine (0.05 mL) were added and the reaction mixture was shaken at room temperature for 4 h. The resin was filtered and washed as before. The resin was suspended in 1 mL TFA:DCM:phenol:thioanisole (70:20:5:5) and shaken for 0.5 h, filtered and washed. The resin was shaken in 2 mL 5% TEA in DCM for 24 h. The resin was filtered into a collection flask and rinsed with additional DCM (3×). The filtrate was concentrated and the product was purified by preparative thin-layer chromatography (SiO$_2$, hexanes:EtOAc 1:5) then triturated in a mixture of DCM and hexanes to provide the title compound as white solid (4 mg, 0.07 mmol, 80%): $^1$H NMR (400 MHz, CDCl$_3$) δ 7.53 (d, J=8.4 Hz, 2H), 7.4–7.3 (m, 4H), 7.05 (t, J=5.6 Hz, 1H), 4.63–4.48 (m, 2H), 4.46–4.31 (m, 3H), 3.79–3.72 (m, 1H), 3.44–3.38 (m, 1H), 3.16–3.06 (m, 4H), 2.50–2.25 (m, 4H), 2.180 (m, 1H), 1.73 (m, 1H), 1.40–1.21 (m, 3H), 1.35 (t, J=7.2 Hz, 3H) ppm. ESMS m/z 592 (M+H)$^+$; (neg. ion) 590 (MH)$^+$.

EXAMPLE 4

Ethyl (9aS)-5-oxo-4-[4-({[(1R)-1-(4-pyridinyl)ethyl]amino}carbonyl)phenyl]-2-{2-[4-(trifluoromethyl)phenyl]ethyl}-7,8,9,9a-tetrahydro-5H-pyrido[2,3-a]pyrrolizine-3-carboxylate A. 4-[(1R)-1-Azidoethyl]pyridine (S) α-Methyl-1(4-pyridyl)methanol (2.22 g, 18.0 mmol, 98% e.e.) was dissolved in 40 mL dry toluene and cooled to 0° C. Diphenyl phosphorylazide (5.95 g, 21.6 mmol) was added and the solution was stirred in ice bath for 5 min at which time DBU (5.31 g, 34.9 mmol) was added all at once. The stirred reaction mixture was allowed to come to room temperature overnight then diluted with ether, washed with water (2×). The aqueous layer was extracted with ether (2×) and the combined organic layers were washed with water, 5% NaHCO$_3$, brine and dried over MgSO$_4$. Purification on SiO$_2$ (hexanes:EtOAc 3:2 to 1:1) provided the azide as a yellow oil (1.33 g, 9.0 mmol, 50. %): $^1$H NMR (300 MHz, CDCl$_3$) δ 8.66 (d, J=5.9 Hz, 2H), 7.31 (d, J=5.9 Hz, 2H), 4.67 (q, J=6.8 Hz, 1H), 1.58 (d, J=6.8 Hz, 3H) ppm.

B. (1R)-1-(4-Pyridinyl)ethylamine

4-[(1R)-1-Azidoethyl]pyridine (1.0 g, 6.7 mmol) was dissolved in 25 mL EtOH amd hydrogenated at 45 psi over 100 mg Lindlar's catalyst (5% w/w). After 2 h, the reaction mixture was filtered through Celite, concentrated and purified on SiO$_2$ (DCM:MeOH:NH4OH 95:5:0.1) to provide the amine as a yellow oil (0.583 g, 4.78 mmol, 71%): $^1$H NMR (300 MHz, CDCl$_3$) δ 8.44 (dd, J=4.5, 1.5 Hz, 2H), 7.34 (d, J=5.8 Hz, 2H), 3.93 (q, J=6.8 Hz, 1H), 3.3 (bs, 2H), 1.21 (d, J=6.5 Hz, 3H) ppm.

C. 4-((9aS)-3-(Ethoxycarbonyl)-5-oxo-2-{2-[4-(trifluoromethyl)phenyl]ethyl}-7,8,9,9a-tetrahydro-5H-pyrido[2,3-a]pyrrolizin-4-yl)benzoic acid Ethyl (2Z)-3-amino-5-[4-(trifluoromethyl)phenyl]-2-pentenoate (28.73 g, 100 mol), 4-carboxy-benzaldehyde (15.0 g, 100 mmol), tert-butyl (2S)-2-(3-ethoxy-3-oxopropanoyl)-1-pyrrolidinecarboxylate (28.52 g, 100 mmol), and piperidine (4.94 mL, 50 mmol) were added to 100 mL toluene and refluxed under Dean-Stark conditions for 18 h. The reaction mixture was cooled to ambient temperature, diluted with EtOAc and washed with pH 4.0 buffer (2×), brine and dried over Na$_2$SO$_4$. The organics were concentrated and used without further purification. The crude dihydropyridine (68.67 g, 100 nmol) was dissolved in 200 mL CH$_3$CN and 200 mL H$_2$O followed by the addition of ceric ammonium nitrate (109.64, 200 mmol). The reaction mixture was stirred for 45 min and then diluted with EtOAc. The organics were extracted and washed with H$_2$O and brine and then dried (Na2SO$_4$), filtered and concentrated to a reddish-brown residue. The residue was redissolved in 250 mL of 70% TFA in CH$_2$Cl$_2$. After 1.5 h of stirring at rt, the reaction mixture was concentrated and the residue redissolved in 300 mL of 10% triethylamine in CH$_2$Cl$_2$. After 20 h of stirring at rt the reaction was again concentrated and the resulting residue taken up in EtOAc and washed with pH 4.0 buffer (2×), brine and dried over Na$_2$SO$_4$. Filtration followed by concentration and chromatography on silica gel (90% EtOAc, 10% MeOH) eluted the title compound as a white solid (21.50 g, 39.92 mmol, 40%):

$^1$H NMR (400 MHz, CD$_3$OD) 8.04 (d, J=8.2 Hz, 2H), 7.53 (d, J=8.1 Hz, 2H), 7.40 (d, J=8.3 Hz, 2H), 7.35 (d, J=8.0 Hz, 2H), 4.79 (dd, J=10.3, 5.5 Hz, 1H), 3.97 (dd, J=14.3, 7.1 Hz, 2H), 3.63–3.57 (m, 1H), 3.39–3.32 (m, 1H), 3.20–3.13 (m, 4H), 2.42–2.34 (m, 3H), 1.40–1.30 (m, 1H), 0.87 (t, J=7.1 Hz, 3H).

D. 4-((9aS)-3-(Ethoxycarbonyl)-5-oxo-2-{2-[4-(trifluoromethyl)phenyl]ethyl}-7,8,9,9a-tetrahydro-5H-pyrido[2,3-α]pyrrolizin-4-yl)benzoic acid (0.178 g, 0.331 mmol) was dissolved in 4 mL DCM. (1R)-1-(4-Pyridinyl)ethylamine (0.081 g, 0.661 mmol) was added followed by HOBT (0.054 g, 0.397 mmol) and EDC (0.076 mg, 0.397 mmol). After 3 h, the reaction mixture was washed with pH 4.0 phosphate buffer (2×), 5% NaHCO$_3$, and brine and dried over MgSO$_4$. Purification on SiO$_2$ (EtOAc 100% to EtOAc:MeOH: NH$_4$OH 95:5:0.3) then by TLC (SiO$_2$; EtOAc:MeOH 95:5) provided the title compound as a tan solid (0.077 g, 0.12 mmol, 36%): $^1$H NMR (400 MHz, CDCl$_3$) δ 8.52 (d, J=6.0 Hz, 2H), 7.80 (d, J=8.0 Hz, 2H), 7.51 (d, J=8.0 Hz, 2H), 7.42 (d, J=8.4 Hz, 2H), 7.30 (d, J=8.4 Hz, 2H), 7.27 (d, J=4.4 Hz, 2H), 6.51 (d, J=7.2 Hz, 1H), 5.27 (m, 1H), 4.69 (dd, J=10.4, 6.4 Hz, 1H), 3.99 (m, 2H), 3.66 (m, 1H), 3.35 (m, 1H), 3.18 (m, 2H), 3.14 (m, 1H), 2.45 (m, 1H), 2.33 (m, 2H), 1.7 (bs, 1NH, 2H$_2$O), 1.56 (d, J=6.8 Hz, 3H), 1.35 (m, 1H), 0.91 (t, J=6.8 Hz, 3H) ppm. ESMS m/z (pos. ion) 643 (M+H)$^+$, (neg. ion) 641 (M−H)$^+$.

EXAMPLE 5

Ethyl (9aS)-5-oxo-4-[4-({[(1S)-1-(4-pyridinyl)ethyl] amino}carbonyl)phenyl]-2-{2-[4-(trifluoromethyl) phenyl]ethyl}-7,8,9,9a-tetrahydro-5H-pyrido[2,3-α] pyrrolizine-3-carboxylate 4-((9aS)-3-(Ethoxycarbonyl)-5-oxo-2-{2-[4-(trifluoromethyl)phenyl]ethyl}-7,8,9,9a-tetrahydro-5H-pyrido[2,3-α] pyrrolizin-4-yl)benzoic acid (0.264 g, 0.491 mmol) was dissolved in 1 mL DMF. (1S)-1-(4-Pyridinyl)ethylamine (0.090 g, 0.736 mmol; prepared identically to its enantiomer, but starting with (R) α-methyl-1(4-pyridyl)methanol) was added followed by PyBOP (0.383 mg, 0.736 mmol). After 14 h, the reaction mixture was added to half-saturated NaCl solution and extracted with EtOAc (3×). The combined organic layers were washed with pH 4.0 phosphate buffer (2×), 5% NaHCO$_3$, and brine and dried over Na$_2$SO$_4$. Purification on SiO$_2$ (hexanes:EtOAc 20:80 to 0:100 to) provided the title compound as a white solid (0.153 g, 0.238 mmol, 48%): mp=158–160° C. $^1$H NMR (300 MHz, CDCl$_3$) δ 8.62 (d, J=5.7 Hz, 2H), 7.86 (d, J=8.1 Hz, 2H), 7.57 (d, J=8.1 Hz, 2H), 7.49 (d, J=8.1 Hz, 2H), 7.37 (d, J=8.1 Hz, 2H), 7.33 (d, J=5.5 Hz, 2H), 6.52 (d, J=7.5 Hz, 1H), 5.33 (m, 1H), 4.75 (dd, J=10.3, 6.3 Hz, 1H), 4.06 (m, 2H), 3.75 (m, 1H), 3.41 (m, 1H), 3.22 (m, 4H), 2.52 (m, 1H), 2.40 (m, 2H), 1.63 (d, J=7.0 Hz, 3H), 1.40 (m, 1H), 0.97 (t, J=7.1 Hz, 3H) ppm. ESMS m/z 643 (M+H)$^+$. Anal. calcd. for C$_{36}$H$_{33}$F$_3$N$_4$O$_4$·½H$_2$O: C, 66.35; H, 5.26; N, 8.60; found: C, 66.35; H, 5.42; N, 8.79.

EXAMPLE 6

Ethyl (9aS)-2-(2,4-difluorobenzyl)-4-(4-{[(2-furylmethyl)amino]carbonyl}phenyl)-5-oxo-7,8,9,9a-tetrahydro-5H-pyrido[2,3-α]pyrrolizine-3-carboxylate A. Ethyl 4-(2,4-difluorophenyl)-3-oxobutanoate.

DCC (6.1 g, 30mmol) was added in portions to a stirred solution of 2,4-difluorophenylacetic acid (5.1 g, 30. mmol), Meldrum's acid (4.3 g, 30. mmol) and DMAP (7.2 g, 60. mmol) in 100 mL DCM. After stirring at ambient temperature for 3 h, the reaction mixture was filtered through Celite and the filtrate was washed with 1N HCl (2×), water and brine and dried over MgSO$_4$. After filtration and concentration, the acyl Meldrum's acid was refluxed in 100 mL absolute EtOH for 1.5 h. Concentration provided the β-keto ester as a clear oil (7.2 g, 30. mmol, 100%). $^1$H NMR (400 MHz, CDCl$_3$) δ 7.2–7.1 (m, 1H), 6.9–6.7 (m, 2H), 4.16 (q, J=7.0 Hz, 2H), 3.81 (s, 2H), 3.48 (s, 2H), 1.24 (t, J=7.2 Hz, 3H) ppm.

B. Ethyl (2Z)-3-amino-4-(2,4-difluorophenyl)-2-butenoate

Ethyl 4-(2,4-difluorophenyl)-3-oxobutanoate (7.2 g, 30. mmol) was dissolved in 150 mL toluene and refluxed with NH$_4$OAc (11 g, 150 mmol) in a Dean-Stark apparatus. After 16 h, the reaction mixture was allowed to cool, washed with water (3×), brine and dried over MgSO$_4$. Filtration and concentration provided the title compound as a light yellow oil (7.6 g, 31 mmol). $^1$H NMR (400 MHz, CDCl$_3$) δ 7.3–7.1 (m, 1H), 6.9–6.8 (m, 2H), 4.60 (s, 1H), 4.14 (q, J=7.2 Hz, 2H), 3.47 (s, 2H), 1.28 (t, J=7.2 Hz, 3H).

C. tert-Butyl (2S)-2-(3-ethoxy-3-oxopropanoyl)-1-pyrrolidinecarboxylate tert-Butyl (2S)-2-[(2,2-dimethyl-4,6-dioxo-1,3-dioxan-5-yl)carbonyl]-1-pyrrolidinecarboxylate (85 g, 250 mmol) was dissolved in 500 mL absolute EtOH and refluxed for 3 h. Concentration provided the title compound as a light yellow oil (68.4 g, 240 mmol, 96%). $^1$H NMR (400 MHz, CDCl$_3$, mixture of rotamers and keto/enol tautomers) δ 4.35 (m, 0.5H), 4.25 (m, 0.5H), 4.17 (m, 2H), 3.6–3.4 (m, 3H), 2.2–1.8 (m, 4H), 1.4 (m, 9H), 1.15 (m, 3H) ppm.

D. 4-[(9aS)-2-(2,4-Difluorobenzyl)-3-(ethoxycarbonyl)-5-oxo-7,8,9,9a-tetrahydro-5H-pyrido[2,3-α]pyrrolizin-4-yl]benzoic acid Ethyl (2Z)-3-amino-4-(2,4-difluorophenyl)-2-butenoate (1.45 g, 6.0 mmol), 4-formylbenzoic acid (0.90 g, 6.0 mmol), tert-butyl (2S)-2-(3-ethoxy-3-oxopropanoyl)-1-pyrrolidinecarboxylate (1.73 g, 6.0 mmol), and piperidine (0.25 g, 3.0 mmol, 0.30 mL) were added to 20 mL toluene and refluxed under Dean-Stark conditions for 18 h. The reaction mixture was allowed to come to room temperature, diluted with EtOAc and washed with pH 4.0 buffer (2×), and brine, and dried over MgSO$_4$. Purification on SiO$_2$ (hexanes: EtOAc 3:2 provided the diastereomeric dihydropyridine as yellow foam (1.87 g, 2.92 mmol, 49%): ESMS m/z (pos. ion) 641 (M+H)$^+$; (neg. ion) 639 (M−H)$^+$. The dihydropyridine (1.87 g, 2.92 mmol) was dissolved in 100 mL EtOAc and stirred vigorously with a solution of ceric ammonium nitrate (3.2 g, 5.84 mmol) in 100 mL water. After 3 h, the organic layer was washed with pH 4.0 buffer. The combined aqueous layers were extracted with EtOAc (2×) and the combined organic layers were washed with brine and dried over MgSO$_4$. Filtration and concentration provided a foam that was taken up in 30 mL of 70% TFA in DCM. After 1.5 h, the reaction mixture was concentrated in vacuo then taken up in 50 mL of 10% TEA in DCM. After 72 h, the volatiles were removed and the resulting oil was taken up in EtOAc and washed with pH 4.0 buffer (2×), brine and dried over MgSO$_4$. Filtration and concentration provided the title compound as a yellow foam (1.37 g, 2.78 mmol, 95%): $^1$H NMR (400 MHz, CDCl$_3$) δ 8.09 (d, J=8.0 Hz, 2H), 7.45 (d, J=7.6 Hz, 2H), 7.18 (m, 1H), 6.77 (m, 2H), 4.74 (m, 1H), 4.33 (AB, J=22.3, 15.2 Hz, 2H), 3.88 (m, 2H), 3.72 (m, 1H), 3.38 (m, 1H), 2.6–2.2 (m, 3H), 1.4–1.3 (m, 1H), 0.78 (t, J=7.2 Hz, 3H) ppm. ESMS m/z 493 (M+H)$^+$, 985 (2M+H)$^+$.

E. 4-[(9aS)-2-(2,4-Difluorobenzyl)-3-(ethoxycarbonyl)-5-oxo-7,8,9,9a-tetrahydro-5H-pyrido[2,3-α]pyrrolizin-4-yl]benzoic acid (0.120 g, 0.244 mmol) was dissolved in 2 mL DCM. 2-Furfurylamine (0.035 g, 0.365 mmol) was added followed by EDC (0.070 g, 0.365 mmol). After 3 h, the reaction mixture was diluted with EtOAc and washed with pH 4.0 buffer (3×), saturated NaHCO$_3$, brine, and dried over MgSO$_4$. Purification on SiO$_2$ (hexanes:EtOAc 1:1 to 1:2) provided the title compound as a white solid (0.082 g, 0.14 mmol, 59%): $^1$H NMR (400 MHz, CDCl$_3$) δ 7.81 (d, J=8.0 Hz, 2H), 7.43 (d, J=8.0 Hz, 2H), 7.17 (m, 1H), 6.78 (m, 2H), 6.43 (t, J=5.2 Hz, 1H), 6.34 (m, 1H), 6.30 (m, 1H), 4.69 (dd, J=12.4, 6.4 Hz, 1H), 4.64 (d, J=5.6 Hz, 2H), 4.31 (AB, J=15.6, 2H), 3.90 (dq, J=7.2, 2.0 Hz, 2H), 3.68 (m, 1H), 3.35 (m, 1H), 2.45 (m, 1H), 2.30 (m, 2H), 1.38 (m, 1H), 0.85 (t, J=7.2 Hz, 3H) ppm. ESMS m/z 572 (M+H)$^+$, 604 (M+Na)$^+$. Anal. calcd. for C$_{32}$H$_{27}$F$_2$N$_3$O$_5$.¼H$_2$O: C, 66.72; H, 4.81; N, 7.29; found: C, 66.70; H, 4.70; N, 7.21.

EXAMPLE 7

Ethyl (9aS)-4-{4-[(anilinocarbonyl)amino]phenyl}-5-oxo-2-{2-[4-(trifluoromethyl)phenyl]ethyl}-7,8,9,9a-tetrahydro-5H-pyrido[2,3-α]pyrrolizine-3-carboxylate A. Polymer-bound tert-butyl (3-oxopropanoyl)-1-pyrrolidinecarboxylate (2.5 g, 1.1 mmol, 0.44 meq/g) was suspended in 25 mL anhydrous DMF and 4-nitrobenzoic acid (1.7 g, 11 mmol) was added followed by piperidine (0.22 mL), and trimethyl orthoformiate (0.72 mL). After 18 h at 65° C., the resin was filtered and washed as above and resuspended in 6 mL fresh DMF. Ethyl (2Z)-3-amino-5-[4-(trifluoromethyl)phenyl]-2-pentenoate (3.2 g, 11 mmol) was added followed by trimethyl orthoformate (0.72 mL) and the sealed reaction mixture was heated at 80° C. for 16 h. The resin was filtered and washed as before. The resin was suspended in DCM (10 mL) and DDQ (0.62 g, 2.75 mmol) was added. The brown suspension was shaken at room temperature for 10 min then filtered and washed as before. The resin was dried overnight at 30° C. under high vacuum. The resin was suspended in DMF (20 mL) and 10 mL of a 2.0 M aqueous solution of SnCl$_2$2H$_2$O was added and the mixture was shaken at room temperature for 16 h. The resin was filtered and washed with water (5×) then organic solvents as before then taken up in 70% TFA in DCM and shaken for 16 h. Filtration and washing was followed by treatment of the resin with 5% TEA in DCM (25 mL) for 72 h. Filtration, rinsing the resin with DCM provided the aniline as a reddish oil (0.227 g, 0.44 mmol, 100%): ESMS m/z 510 (M+H)$^+$. Treatment of 0.071 g (0.139 mmol) of aniline in 1 mL CHCl$_3$ with phenylisocyanate (0.020 g, 0.167 mmol) for 0.75 h, concentration and purification by thin-layer chromatography (SiO$_2$, 2000 µm; EtOAc:MeOH 3:1) provided the title compound (35 mg) which was recrystallized from EtOAc/i-Pr$_2$O and dried at 45° C. under high vac. to provide a white solid (24 mg, 0.038 mmol, 27% for final step): mp=137–139° C. $^1$H NMR (400 MHz, CDCl$_3$) δ 7.52 (d, J=8.1 Hz, 2H), 7.34 (d, J=8.4 Hz, 2H), 7.4–7.1 (m, 8H), 7.00 (m, 1H), 4.82 (m, 1H), 4.00 (m, 2H), 3.75 (m, 1H), 3.46 (m, 1H), 3.22 (m, 2H), 3.2–3.1 (m, 2H), 2.59 (m, 1H), 2.40 (m, 2H), 1.8–1.4 (bs, NH, H$_2$O); 1.4 (m, 1H), 0.92 (t, J=7.0 Hz, 3H) ppm. ESMS m/z 629 (M+H)$^+$. Anal. calcd. for 35H31F3N4O4.½H$_2$O: C, 65.93; H, 5.06; N, 8.79, found: C, 65.90; H, 5.04; N, 8.69.

EXAMPLE 8

Ethyl 2-[2-(4-fluorophenyl)ethyl]-4-(4-{[(2-furylmethyl)amino]carbonyl}phenyl)-5-oxo-8,9-dihydro-5H,7H-pyrazolo[1',2':1,2]pyrazolo[3,4-b]pyridine-3-carboxylate A. 5-[3-(4-Fluorophenyl)propanoyl]-2,2-dimethyl-1,3-dioxane-4,6-dione DCC (20.6 g, 100. mmol) was added in portions to a stirred solution of 3-(4-fluorophenyl)propionic acid (16.8 g, 100. mmol), Meldrum's acid (14.4 g, 100. mmol) and DMAP (24.4 g, 200. mmol) in 200 mL DCM. After stirring at ambient temperature for 8 h, the reaction mixture was filtered through Celite, the filtrate was washed with 1N HCl (2×), water and brine and dried over $Na_2SO_4$. Filtration and concentration provided the acyl Meldrum's acid derivative as a yellow solid (29.4 g, 100. mmol, 100%): $^1$H NMR (400 MHz, $CDCl_3$) δ 7.22 (m, 2H), 6.98 (m, 2H), 3.38 (t, J=7.7 Hz, 2H), 2.99 (t, J=7.7 Hz, 2H), 1.69 (s, 6H) ppm.

B. Ethyl 5-(4-fluorophenyl)-3-oxopentanoate

5-[3-(4-Fluorophenyl)propanoyl]-2,2-dimethyl-1,3-dioxane-4,6-dione (29.4 g, 100. mmol) was dissolved in 200 mL absolute EtOH and refluxed for 6 h. Concentration provided the β-ketoester as a yellow oil (23.8 g, 100. mmol, 100%): $^1$H NMR (400 MHz, $CDCl_3$) δ 7.15 (m, 2H), 6.96 (m, 2H), 4.18 (q, J=7.1 Hz, 2H), 3.42 (s, 2H), 2.88 (m, 4H), 1.26 (t, J=7.1 Hz, 3H) ppm.

C. 4-[2-(Ethoxycarbonyl)-5-(4-fluorophenyl)-3-oxo-1-pentenyl]benzoic acid (1:1 mixture of E and Z isomers)

A mixture of 4-carboxybenzaldehyde (2.07 g, 13.81 mmol), ethyl 5-(4-fluorophenyl)-3-oxopentanoate (3.29 g, 13.81 mmol) and piperidine (0.25 mL, 2.53 mmol) in benzene (60 mL) was heated at reflux overnight under Dean-Stark conditions. The reaction mixture was concentrated and the crude material was dissolved in EtOAc. The EtOAc solution was washed with 0.1 M HCl and brine and then dried, filtered, and concentrated. Recrystallization of the resulting material from EtOAc/hexanes produced the title compound as a yellow solid (1.3 g, 3.51 mmol, 25%): $^1$H NMR (400 MHz, $CDCl_3$) δ 8.09 (d, 2H, J=8), 7.98 (d, 2H, J=8), 7.70 (s, 1H), 7.60 (s, 1H), 7.49 (d, 2H, J=8), 7.32 (d, 2H, J=8), 7.16 (dd, 2H, J=8, 6), 7.07 (dd, 2H, J=8, 6), 6.97 (t, 2H, J~9), 6.91 (t, 2H, J~9), 4.29 (q, 2H, J=7), 4.27 (q, 2H, J=7), 3.03 (m, 2H), 2.99 (m, 2H), 2.90 (m, 2H), 2.84 (m, 2H), 1.29 (t, 3H, J=7), 1.23 (t, 3H, J=7) ppm (carboxyl proton not found).

D. 4-{3-(Ethoxycarbonyl)-2-[2-(4-fluorophenyl)ethyl]-5-oxo-1,5,8,9-tetrahydro-4H,7H-pyrazolo[1',2':1,2]pyrazolo[3,4-b]pyridin-4-yl}benzoic acid The product from Step C (920 mg, 2.48 mmol) and NaOEt (170 mg, 2.50 mmol) were added portionwise to a stirred solution of 3-amino-6,7-dihydro-1H,5H-pyrazolo[1,2-a]pyrazol-1-one hydrochloride (refs. R. B. Greenwald, U.S. Pat. No. 4,128,425 and E. E. Boros, F. Bouvier, S. Randhawa and M. H. Rabinowitz, *J. Heterocyclic Chem*., 2001, 38, 613–616.) (440 mg, 2.51 mmol) in EtOH (6 mL). The reaction mixture was heated at reflux for 5.5 h and then allowed to cool to rt and filtered to remove NaCl. The filtrate was concentrated at reduced pressure and the remaining material was triturated with $CH_2Cl_2$ to yield D as an off-white solid (500 mg, 1.02 mmol, 41%): $^1$H NMR (400 MHz, DMSO-$d_6$) δ 12.63 (br, 1H), 9.76 (s, 1H), 7.77 (d, 2H, J=8), 7.27 (dd, 2H, J=8, 6), 7.20 (d, 2H, J=8), 7.11 (t, 2H, J~9), 4.76 (s, 1H), 3.87 (q, 2H, J=7), 3.42 (m, 2H), 3.27 (m, 2H), 2.98 (m, 2H), 2.85 (m, 2H), 2.26 (m, 2H), 0.96 (t, 3H, J=7) ppm; ESI-MS m/z 492 (M+H)$^+$.

E. 4-{3-(Ethoxycarbonyl)-2-[2-(4-fluorophenyl)ethyl]-5-oxo-8,9-dihydro-5H,7H-pyrazolo[1'2':1,2]pyrazolo[3,4-b]pyridin-4-yl}benzoic acid A solution of ceric ammonium nitrate (228 mg, 0.42 mmol) in acetonitrile (1 mL) and water (0.2 mL) was added dropwise to a solution of the product from Step D (102 mg, 0.21 mmol) in acetonitrile (1 mL). The resulting solution was stirred at rt for 2 h and then concentrated at reduced pressure. Trituration of the remaining material with a mixture of $CH_2Cl_2$ and water provided E as a light yellow solid (75 mg, 0.15 mmol, 73%): $^1$H NMR (400 MHz, DMSO-$d_6$) δ 13.05 (br, 1H), 7.95 (d, 2H, J=8), 7.41 (d, 2H, J=8), 7.22 (dd, 2H, J=8, 6), 7.07 (t, 2H, J~9), 3.87 (m, 4H), 3.77 (t, 2H, J=7), 3.07 (m, 2H), 2.99 (m, 2H), 2.54 (quint., 2H, J=7), 0.75 (t, 3H, J=7) ppm; ESI-MS m/z 490 (M+H)$^+$.

F. Ethyl 2-[2-(4-fluorophenyl)ethyl]-4-(4-{[(2-furylmethyl)amino]carbonyl}-phenyl)-5-oxo-8,9-dihydro-5H,7H-pyrazolo[1',2':1,2]pyrazolo[3,4-b]pyridine-3-carboxylate EDCI (31 mg, 0.16 mmol) was added to a solution of furfuryl amine (14 mg, 0.15 mmol), the product from Step E (71 mg, 0.15 mmol) and HOBT.$H_2O$ (20 mg, 0.15 mmol) in DMF (2.5 mL). The reaction was stirred 4 h at rt and then concentrated at reduced pressure. The remaining material was dissolved in $CH_2Cl_2$, washed with water, dried, filtered and concentrated. Chromatography on silica gel afforded the title compound as a yellow solid (30 mg, 0.05 mmol, 33%): $^1$H NMR (400 MHz, DMSO-$d_6$) δ 9.06 (t, 1H, J=6), 7.89 (d, 2H, J=8), 7.56 (br s, 1H), 7.38 (d, 2H, J=8), 7.22 (br t, 2H J~8), 7.07 (t, 2H, J=9), 6.37 (br s, 1H), 6.26 (d, 1H, J=3), 4.46 (d, 2H, J=6), 3.90 (m, 4H), 3.77 (t, 2H, J=7), 3.06 (m, 2H), 2.99 (m, 2H), 2.54 (quint., 2H, J=7), 0.78 (t, 3H, J=7) ppm; ESI-MS m/z 569 (M+H)$^+$;

Anal. calcd. for $C_{32}H_{29}FN_4O_5$·½$H_2O$: C, 66.54; H, 5.24; N, 9.70; found: C,66.52 H5.13; N, 9.70.

EXAMPLE 9

Ethyl 2-[2-(4-fluorophenyl)ethyl]-4-(5-{[(2-furylmethyl)amino]carbonyl}-2-thienyl)-5-oxo-8,9-dihydro-5H,7H-pyrazolo[1',2':1,2]pyrazolo[3,4-b]pyridine-3-carboxyl The title compound was prepared from 5-formyl-2-thiophenecarboxylic acid using methods similar to those described in Steps C-F of above-recited Example 8: $^1$H NMR (400 MHz, DMSO-$d_6$) δ 9.08 (t, 1H, J=6), 7.76 (d, 1H, J=4), 7.56 (s, 1H), 7.21 (m, 3H), 7.06 (t, 2H, J=9), 6.37 (t, 1H, J=3), 6.27 (d, 1H, J=3), 4.43 (d, 2H, J=6), 4.05 (q, 2H, J=7), 3.86 (t, 2H, J=7), 3.79 (t, 2H, J=7), 3.00 (m, 4H), 2.54 (quint., 2H, J=7), 0.96 (t, 3H, J=7) ppm; ESI-MS m/z 575 (M+H)$^+$; Anal. calcd. for $C_{30}H_{27}FN_4O_5S$: C, 62.71; H, 4.74; N, 9.75; found: C, 62.49; H, 4.75; N, 9.81.

EXAMPLE 10

Ethyl 4-(4-{[(3-fluorobenzyl)amino]carbonyl}phenyl)-5-oxo-2-(trifluoromethyl)-8,9-dihydro-5H,7H-pyrazolo[1',2':1,2]pyrazolo[3,4-b]pyridine-3-carboxylate A. 4-[3-(Ethoxycarbonyl)-5-oxo-2-(trifluoromethyl)-1,5,8,9-tetrahydro-4H,7H-pyrazolo[1',2':1,2]pyrazolo[3,4-b]pyridin-4-yl]benzoic acid A mixture of ethyl 4,4,4-trifluoroacetoacetate (0.3 mL, 2.05 mmol), 4-carboxybenzaldehyde (300 mg, 2.00 mmol), 3-amino-6,7-dihydro-1H,5H-pyrazolo[1,2-a]pyrazol-1-one hydrochloride (refs. R. B. Greenwald, U.S. Pat. No. 4,128, 425, and E. E. Boros, F. Bouvier, S. Randhawa and M. H. Rabinowitz, *J. Heterocyclic Chem*., 2001, 38, 613–616.) (~350 mg, 2.00 mmol) and NaOEt (170 mg, 2.5 mmol) in EtOH (5 mL) was heated at reflux for 24 h. The reaction mixture was diluted with water and the resulting precipitate was collected by filtration. The filter cake was triturated with EtOAc to afford the title compound as a white solid (460 mg, 1.05 mmol, 51% crude): $^1$H NMR (400 MHz, DMSO-$d_6$) δ 12.79 (br s, 1H), 10.19 (s, 1H), 7.83 (d, 2H, J=8), 7.25 (d, 2H, J=8), 4.78 (s, 1H), 3.92 (q, 2H, J=7), 3.40 (m, 4H), 2.30 (m, 2H), 0.98 (t, 3H, J=7) ppm; ESI-MS m/z 436 (M−H)$^-$;

B. Ethyl 4-(4-{[(3-fluorobenzyl)amino] carbonyl}phenyl)-5-oxo-2-(trifluoromethyl)8,9-dihydro-5H,7H-pyrazolo[1',2':1,2]pyrazolo[3,4-b]pyridine-3-carboxylate.

The product from Step A was treated as described in Step E of Example 8 followed by coupling to 3-fluorobenzylamine as described in Step F of Example 8 to provide the title compound as a yellow solid: $^1$H NMR (400 MHz, DMSO-$d_6$) δ 9.19 (t, 1H, J=6), 7.93 (d, 2H, J=8), 7.45 (d, 2H, J=8), 7.35 (dd, 1H, J=14, 8), 7.14 (m, 2H), 7.05 (t, 1H, J=9), 4.49 (d, 2H, J=6), 3.98 (m, 4H), 3.84 (t, 2H, J=7), 2.60 (quint., 2H, J=7), 0.91 (t, 3H, J=7) ppm; ; ESI-MS m/z 543 (M+H)$^+$; Anal. calcd. for $C_{27}H_{22}F_4N_4O_4$·⅓$H_2O$: C, 59.12; H, 4.17; N, 10.21; found: C, 59.12; H, 4.14; N, 10.26.

EXAMPLE 11

Ethyl(9aS)-4-(4-{[(2-furylmethyl)amino] carbonyl}phenyl)-5-oxo-2-{2-[4-(trifluoromethyl) phenyl]ethyl}-7,8,9,9a-tetrahydro-5H-pyrido[2,3-a] pyrrolizine-3-carboxylate A. 4-(9aS)-3-(ethoxycarbonyl)-5-oxo-2-{2-[4-(trifluoromethyl)phenyl]ethyl}-7,8,9,9a-tetrahydro-5H-pyrido[2,3-a]pyrrolizin-4-yl)benzoic acid Example 4C (0.500 g, 0.491 mmol) was dissolved in $CH_2Cl_2$. Furfuryl amine (0.012 mL, 1.39 mmol) was added followed by EDCI (0.214 g, 1.11 mmol) and HOBt (0.151 g, 1.11 mmol). After 14 h of stirring at ambient temperature the reaction mixture was poured onto 5% HCl solution and extracted with $CH_2Cl_2$. The organics were washed with sat'd $NaHCO_3$, brine, and then dried ($Na_2SO_4$), filtered and concentrated to a brown residue. Chromatography on silica gel using 3:1 EtOAc:Hexanes eluted the product to provide the title compound upon concentration as a white solid (0.460 g, 80%): $^1$H NMR (CDCl$_3$, 400 MHz) δ 7.80 (d, J=8.3 Hz, 2H), 7.51 (d, J=8.1 Hz, 2H), 7.42 (d, J=8.2 Hz, 2H), 7.36 (m, 1H), 7.30 (d, J=8.1 Hz, 2H), 6.47 (m, 1H), 6.32 (m, 1H), 6.28 (m, 1H), 4.68 (dd, J=10.2, 6.3 Hz, 1H), 4.63 (d, 5.3 Hz, 2H), 4.00–3.97 (m, 2H), 3.71–3.67 (m, 1H), 3.37–3.32 (m, 1H), 3.22–3.05 (m, 4H), 2.50–2.45 (m, 1H), 2.39–2.29 (m, 2H), 1.40–1.29 (m, 1H), 0.92 (t, J=6.8 Hz, 3H); ESMS m/z 618 (M+H)$^+$, 616 (M−H)$^+$; Anal. Calcd. For $C_{34}H_{30}F_3N_3O_5$: C, 66.12; H, 4.90; N, 6.80; found: C, 65.94; H, 4.96; N, 6.79.

EXAMPLE 12

Ethyl(9aS)-5-oxo-4-(5-{[(3-pyridinylmethyl)amino] carbonyl}-2-furyl)-2-{2-[4-(trifluoromethyl)phenyl] ethyl}-7,8,9,9a-tetrahydro-5H-pyrido[2,3-a]pyrrolyzine-3-carboxylate A. Tert-Butyl (2S)-2-(3-ethoxy-3-oxopropanoyl)-1-pyrrolidinecarboxylate (2.0 g, 7.01 mmol), 5-formyl-2-furancarboxylic acid (0.983 g,7.01 mmol) and piperidine (0.347 mL, 3.51 mmol) were combined in benzene (10 mL) and refluxed with azeotropic removal of $H_2O$ for 2 h. The reaction was cooled to ambient temperature and concentrated to a brown residue. The Knoevenagel product (1.43 g, 3.51 mmol) and ethyl (2Z)-3-amino-5-[4-(trifluoromethyl)phenyl]-2-pentenoate (0.833 g, 3.51 mmol) were heated to 110° C. for 1 h and then cooled to ambient temperature. The residue was taken up in DMA and CAN (3.85 g, 7.02 mmol) added. The reaction stirred at ambient temperature for 45 min and then $H_2O$ was added. The organics were extracted with $Et_2O$ and washed once with $H_2O$, brine, and then dried (Na2SO4), filtered and concentrated to a brown residue. The crude oil was subjected to TFA (4.5 mL in 1.5 mL $CH_2Cl_2$) for 2 h and then concentrated. The residue was redissolved in $CH_2Cl_2$ (9 mL) and treated with $Et_3N$ (4.5 mL). After 8 h the reaction mixture was concentrated to a brown foam. A solution of this crude material (1.85 g, 3.51 mmol) and 3-(aminomethyl)pyridine in $CH_2Cl_2$ were treated with EDCI and HOBt. After 14 h at ambient temperature, the reaction was diluted with $CH_2Cl_2$ and the organics washed once each 5% HCl, sat'd $NaHCO_3$, brine and then dried ($Na_2SO4$), filtered and concentrated to a brown foam. Chromatography on silica gel using 90:10 EtOAc:MeOH eluted the product to provide the title compound upon concentration as a white solid: $^1$H NMR (CDCl$_3$, 400 MHz) δ 8.91 (s, 1H), 8.63 (d, J=5.3 Hz, 1H), 8.48 (d, J=7.8 Hz, 1H), 8.22 (bs, 1H), 7.85 (m, 1H), 7.52 (d, J=8.0 Hz, 2H), 7.36 (d, J=3.5 Hz, 1H), 7.30 (d, J=8.1 Hz, 2H), 7.27 (d, J=3.7 Hz), 4.80 (d, J=5.8 Hz, 2H), 4.58 (dd, J=10.3, 6.2 Hz, 1H), 4.28 (dd, J=14.3, 7.2 Hz, 2H), 3.79–3.72 (m, 1H), 3.44–3.39 (m, 1H), 3.19–3.10 (m, 4H), 2.45–2.29 (m, 3H), 1.38–1.26 (m, 1H), 1.09 (t, 7.2 Hz, 3H); ESMS m/z 619 (M+H)$^+$, 617 (M−H)$^+$;

EXAMPLE 13

Ethyl(9aS)-4-[3-({[2-(2-furyl)ethyl]amino}carbonyl) phenyl]-5-oxo-2-{2-[4-(trifluoromethyl)phenyl] ethyl}-7,8,9,9a-tetrahydro-5H-pyrido[2,3-a]pyrrolizine-3-carboxylate A. Polymer bound tert-butyl (3-oxopropanoyl)-1-pyrrolidinecarboxylate (1.1 g, 0.49 mmol) was suspended in 6 mL anhydrous DMF and 3-carboxybenzaldehyde (1.50 g, 9.8 mmol) was added followed by piperidine (0.097 mL), and trimethyl orthoformate (0.32 mL). After 5 h at 65° C., the resin was filtered and washed 3 times anhydrous DMF, 3 times $CH_2Cl_2$, 3 times MeOH, 3 times $Et_2O$ and then resuspended in 5 mL fresh DMF. Ethyl (2Z)-3-amino-5-[4-(trifluoromethyl)phenyl]-2-pentenoate (1.41 g, 4.9 mmol) was added followed by trimethyl orthoformate (0.32 mL) and the sealed reaction mixture was heated at 80° C. for 16 h. The resin was filtered and washed as before. The resin was suspended in DMA (5 mL) and CAN (1.34 g, 2.45 mmol) was added. The orange suspension was shaken at ambient temperature for 30 min then filtered and washed as before. The resin was dried overnight at 30° C. under high vacuum. The resin was suspended in 3 mL DMF and 1 mL pyridine. Pentafluorophenyl trifluoroacetate (1.1 mL) was added and the sealed reaction vessel shaken at ambient temperature for 45 min, filtered and washed as above and dried under high vacuum for 2 h. Half of the resin was suspended in DMF (4 mL) and DMAP (10 mg) and 2-furfuryl amine (0.233 g, 2.4 mmol) were added and the reaction vessel shaken at ambient temperature for 4 h. The resin was filtered and washed as before. The resin was suspended in 8 mL TFA:$CH_2Cl_2$: phenol:thioanisole (70:20:5:5) and shaken for 3 h, filtered and washed. The resin was shaken in 6 mL 5% $Et_3N$ in $CH_2Cl_2$ for 14 h. The resin was filtered into a collection flask and rinsed with additional $CH_2Cl_2$ (3×). The filtrate was concentrated and the product purified by radial chromatography 4:1 EtOAc:Hexanes to give the title compound as a white solid (12 mg, 0.019 mmol 81%): $^1$H NMR (CDCl$_3$, 400 MHz) δ 7.91 (d, J=4.2 Hz, 1H), 7.79 (s, 1H), 7.55–7.49 (m, 4H), 7.36–7.33 (m, 3H), 6.55 (m, 1H), 6.33 (m, 1H), 6.30 (m, 1H), 4.70 (dd, J=10.3, 6.2 Hz, 1H), 4.63 (m, 2H), 4.04 (dd, J=14.2, 7.2 Hz, 2H), 3.74–3.67 (m, 1H), 3.41–3.35 (m, 1H), 3.26–3.15 (m, 4H), 2.51–2.44 (m, 1H), 2.39–2.29 (m, 2H), 1.42–1.31 (m, 1H), 0.91 (t, J=7.2 Hz, 3H); ESMS m/z 618 (M+H)$^+$, 616 (M–H)$^+$; Anal Cacld for C34H30F3N3O5 C34H30F3N3O5: C, 66.12; H, 4.90; N, 6.80; found: C, 66.13; H, 4.98; N, 6.66.

EXAMPLE 14

4-((9aS)-5-oxo-2-{2-[4-(trifluromethyl)phenyl]ethyl}-7,8,9,9a-tetrahydro-5H-pyrido[2,3-a]pyrrolizin-4-yl)-N-(2-furylmethyl)benzamide A. Polymer bound tert-butyl (3-oxopropanoyl)-1-pyrrolidinecarboxylate (2.2 g, 0.98 mmol) was suspended in 6 mL anhydrous DMF and 4-caborxybenzaldehyde (3.00 g, 19.6 mmol) was added followed by piperidine (0.194 mL, 1.96 mmol), and trimethyl orthoformate (0.643 mL, 5.88 mmol). After 5 h at 65° C., the resin was filtered and washed 3 times anhydrous DMF, 3 times CH$_2$Cl$_2$, 3 times MeOH, 3 times Et$_2$O and then resuspended in 15 mL fresh DMF. Allyl (2Z)-3-amino-5-[4-(trifluoromethyl)phenyl]-2-pentenoate (2.93 g, 9.8 mmol) was added followed by trimethyl orthoformate (0.643 mL, 5.88 mmol) and the sealed reaction mixture was heated at 80° C. for 16 h. The resin was filtered and washed as before. The resin was resuspended in DMF (8 mL) and CH$_2$Cl$_2$ (8 mL) and Pd(PPh$_3$)$_4$ (0.226 g, 0.196 mmol), TMSN$_3$ (1.04 mL, 7.84 mmol), and TBAF (0.928 g, 2.94 mmol) were added. The sealed reaction vessel was shaken for 1 h at ambient temperature and then the resin was filtered and washed as before and then washed an additional time with toluene. The resin was suspended in toluene and heated to 120° C. for 8 h and then cooled, filtered and washed as described earlier. The resin was suspended in DMA (15 mL) and CAN (2.69 g, 4.9 mmol) was added. The orange suspension was shaken at ambient temperature for 30 min then filtered and washed as before. The resin was dried overnight at 30° C. under high vacuum. The resin was suspended in 10 mL DMF and 4 mL pyridine. Pentafluorophenyl trifluoroacetate (2.2 mL) was added and the sealed reaction vessel shaken at ambient temperature for 45 min, filtered and washed as above and dried under high vacuum for 2 h. Half of the resin was suspended in DMF (10 mL) and DMAP (20 mg) and 2-furfuryl amine (0.866 g, 9.8 mmol) were added and the reaction vessel shaked at ambient temperature for 4 h. The resin was filtered and washed as before. The resin was suspended in 16 mL TFA:CH$_2$Cl$_2$:phenol:thioanisole (70:20:5:5) and shaken for 3 h, filtered and washed. The resin was shaken in 12 mL 5% Et$_3$N in CH$_2$Cl$_2$ for 14 h. The resin was filtered into a collection flask and rinsed with additional CH$_2$Cl$_2$ (3×). The filtrate was concentrated and the product purified by radial chromatography 4:1 EtOAc:Hexanes to give the title compound as a white solid (250 mg, 0.46 mmol 47%): $^1$H NMR (CDCl$_3$, 400 MHz) δ 7.84 (d, J=8.2 Hz, 2H), 7.63 (d, J=8.2 Hz, 2H), 7.54 (d, J=8.0 Hz, 2H), 7.39 (s, 1H), 7.30 (d, J=8 Hz), 7.07 (s, 1H), 6.45 (m, 1H), 6.35 (m, 1H), 6.32 (m, 1H), 4.72 (dd, J=10.4, 6.4 Hz, 1H), 4.66 (d, 5.3 Hz, 2H), 3.77–3.70 (m, 1H), 3.42–3.37 (m, 1H), 3.26–3.16 (m, 4H), 2.50–2.35 (m, 3H), 1.41–1.34 (m, 1H); ESMS m/z 546 (M+H)$^+$, 544 (M–H)$^+$

EXAMPLE 15

Ethyl(9aS)-4-{4-[(2,3-dihydro-1H-inden-1-ylamino)carbonyl]-2-thieny}-2-[2-(4-fluorophenyl)ethyl]-5-oxo-7,8,9,9a-tetrahydro-5H-pyrido[2,3-a]pyrrolizine-3-carboxylate A. 2-(4-bromo-2-thienyl)-1,3-dioxolane A benzene (55 mL) solution of 4-bromo-2-thiophene carboxaldehyde (9.76 g 51.09 mmol), ethylene glycol (8.55 mL, 153.26 mmol) and p-toluenesulfonic acid monohydrate (0.972 g, 5.11 mmol) was refluxed with azeotropic removal of H$_2$O for 6 h and then cooled to ambient temperature. The reaction mixture was diluted with Et$_2$O and the organics washed with sat'd NaHCO$_3$, brine and then dried (MgSO$_4$), filtered and concentrated. Chromatography on silica gel using 95:5 Hexanes:EtOAc eluted the product to provide the title compound upon concentration as a yellow oil (10.76 g 90% yield): $^1$H NMR (CDCl$_3$, 400 MHz) δ 7.22 (s, 1H), 7.08 (s, 1H), 6.07 (s, 1H), 4.14–4.00 (m, 4H).

B. 5-formyl-3-thiophene carboxylic acid

An Et$_2$O solution of the 2-(4-bromo-2-thienyl)-1,3-dioxolane (9.0 g, 38.28 mmol) was cooled to −78° C. and n-butyl lithium (15.31 mL of a 2.5M sol'n in hexane, 38.28 mmol) was slowly added over 20 min. The anion was stirred at −78° C. for 5 min and then poured onto dry ice and quenched with 2 N HCl (100 mL). The mixture was stirred for 30 min and the precipitate filtered, collected and dried to give 3.68 g of an off-white solid (62% yield): $^1$H NMR (DMSO-d6, 400 MHz) δ 13.30–13.00 (bs, 1H), 9.94 (s, 1H), 8.71 (s, 1H), 8.28 (s, 1H)

C. 5-{(9aS)-3-(ethoxycarbonyl)-2-[2-(4-fluoropbenyl)ethyl]-5-oxo-7,8,9,9a-tetrahydro-5H-pyrido[2,3-a]pyrrolizin-4-yl}-3-thiophenecarboxylic acid A DMF (10 mL) solution of tert-Butyl (2S)-2-(3-ethoxy-3-oxopropanoyl)-1-pyrrolidinecarboxylate (2.85 g, 9.99 mmol), 5-formyl-3-thiophene carboxylic acid (1.56 g, 9.99 mmol) and piperidine (0.494 mL, 5.00 mmol) was heatd to 80° C. for 45 min and then cooled to ambient temperature. The reaction mixture was diluted with Et$_2$O and washed 1 N HCl, 2×H$_2$O, 1×brine and the organics dried (Na$_2$SO4), filtered and concentrated to a brown residue. The Knoevenagel product (4.23 g, 9.99 mmol) and ethyl (2Z)-3-amino-5-(4-fluorophenyl)-2-pentenoate (2.37 g, 9.99 mmol) were heated to 110° C. for 1.5 h and then cooled to ambient temperature. The glassy solid was redissolved in CH$_3$CN (20 mL) and H$_2$O (20 mL) followed by addition of ceric ammonium nitrate (10.95 g, 19.98 mmol). The reaction mixture stirred for 45 min at ambient temperature and then Et$_2$O was added and the organics extracted and washed 1×H$_2$O, 1×brine, and then dried (Na$_2$SO$_4$), filtered and concentrated to a dark tan solid. The solid from the previous reaction was subjected to TFA (15 mL in 4 mL CH$_2$Cl$_2$) for 1 h and then concentrated. The residue was redissolved in CH$_2$Cl$_2$ (20 mL) and treated with Et$_3$N (12 mL). After 16 h the reaction mixture was concentrated to a brown foam. The residue was redissolved in CHCl$_3$ and washed 1×pH 4.5 buffer, 1×brine and the organics dried (Na$_2$SO$_4$), filtered and concentrated. Chromatography on silica gel using (4:1 EtOAc:Hexanes with 1% AcOH) eluted the desired compound as a tan solid (1.98 g, 4.00 mmol) 40% yield: $^1$H NMR (CDCl$_3$, 400 MHz) δ 8.33 (s, 1H), 7.60 (s, 1H), 7.17

(dd, J=8.6, 5.5 Hz, 2H), 6.97 (t, J=8.6, 2H), 4.73 (dd, J=10.4, 6.2 Hz, 1H), 4.17 (dd, J=14.3, 7.0 Hz, 2H), 3.82–3.74 (m, 1H), 3.46–3.40 (m, 1H), 3.19–3.04 (m, 4H), 2.52–2.48 (m, 1H), 2.41–2.31 (m, 2H), 1.48–1.38 (m, 1H), 1.11 (t, J=7.0 Hz, 3H) ESMS m/z 495 (M+H)$^+$, 493 (M−H)$^+$

D. 5-{(9aS)-3-(ethoxycarbonyl)-2-[2-(4-fluorophenyl) ethyl]-5-oxo-7,8,9,9a-tetrahydro-5H-pyrido[2,3-a]pyrrolizin-4-yl}-3-thiophenecarboxylic acid (0.100 g, 0.202 mmol) was dissolved in $CH_2Cl_2$. 1-aminoindane (0.039 mL, 0.328 mmol) was added followed by EDCI (0.047 g, 0.243 mmol) and HOBt (0.033 g, 0.243 mmol). After 14 h of stirring at ambient temperature the reaction mixture was poured onto 5% HCl solution and extracted with $CH_2Cl_2$. The organics were washed with sat'd $NaHCO_3$, brine and then dried ($Na_2SO_4$), filtered and concentrated to a brown residue. Chromatography on silica gel using 3:1 EtOAc: Hexanes eluted the product to provide the title compound upon concentration as a white solid (0.085 g, 0.139 mmol, 69% yield): $^1$H NMR (CDCl$_3$, 400 MHz) δ 8.08 (s, 1H), 7.46 (s, 1H), 7.35–7.31 (m, 1H), 7.28–7.20 (m, 3H), 7.16 (dd, J=8.5, 5.5 Hz, 2H), 6.97 (t, 2H), 6.17 (m, 1H), 5.67 (dd, J=15.5, 7.8 Hz, 1H), 4.69 (dd, J=10.4, 6.2 Hz, 1H), 4.19 (dd, J=14.3, 7.0 Hz, 2H), 3.76–3.69 (m, 1H), 3.42–3.36 (m, 1H), 3.19–2.99 (m, 5H), 2.96–2.87 (m, 1H), 2.74–2.64 (m, 1H), 2.51–2.43 (m, 1H), 2.39–2.27 (m, 2H), 1.96–1.86 (m, 1H), 1.41–1.34 (m, 1H), 1.09 (t, 7.0 Hz); ESMS m/z 610 (M+H)$^+$, 608 (M−H)$^+$; Anal. Calcd. For C35H32FN3O4S.½H2O: C, 68.44; H, 5.33; N, 6.84; found: C, 68.42; H, 5.50; N, 6.78.

EXAMPLE 16

Ethyl(9aS)-4-(4-{[(3,4-difluorobenzyl)amino]carbonyl}-2-thienyl)-2-[2-(4-fluorophenyl)ethyl]-5-oxo-7,8,9,9a-tetrahydro-5H-pyrido[2,3-a]pyrrolizine-3-carboxylate A. 5-{(9aS)-3-(ethoxycarbonyl)-2-[2-(4-fluorophenyl) ethyl]-5-oxo-7,8,9,9a-tetrahydro-5H-pyrido[2,3-a]pyrrolizin-4-yl}-3-thiophenecarboxylic acid (0.100 g, 0.202 mmol) was dissolved in $CH_2Cl_2$. 3,4-difluorobenzylamine (0.036 mL, 0.303 mmol) was added followed by EDCI (0.047 g, 0.243 mmol) and HOBt (0.033 g, 0.243 mmol). After 14 h of stirring at ambient temperature the reaction mixture was poured onto 5% HCl solution and extracted with $CH_2Cl_2$. The organics were washed with sat'd $NaHCO_3$, brine and then dried ($Na_2SO_4$), filtered and concentrated to a brown residue. Chromatography on silica gel using 3:1 EtOAc:Hexanes eluted the product to provide the title compound upon concentration as a white solid (0.065 g, 0.105 mmol, 52% yield): $^1$H NMR (CDCl$_3$, 400 MHz) δ 8.06 (s, 1H), 7.48 (s, 1H), 7.17–7.03 (m, 5H), 6.97 (t, J=8.6 Hz, 2H), 6.96 (m, 1H), 4.69 (dd, J=10.4, 6.3 Hz, 1H), 4.51 (d, J=5.8 Hz, 2H), 4.16 (dd, J=14.3, 7.0 Hz, 2H), 3.73–3.63 (m, 1H), 3.42–3.36 (m, 1H), 3.19–2.99 (m, 4H), 2.51–2.43 (m, 1H), 2.39–2.27 (m, 2H), 1.41–1.34 (m, 1H), 1.09 (t, 7.1 Hz); ESMS m/z 620 (M+H)$^+$, 618 (M−H)$^+$; Anal. Calcd. For C33H28F3N3O4S: C, 63.96; H, 4.55; N, 6.78; found C, 64.03; H, 4.58; N, 6.73.

EXAMPLE 17

Ethyl(9aS)-4-{4-[(2,3-dihydro-1H-inden-1-ylamino) carbonyl]-2-furyl}-2-[2-(4-fluorophenyl)ethyl]-5-oxo-7,8,9,9a-tetrahydro-5H-pyrido[2,3-a]pyrrolizine-3-carboxylate A. 2-(4-bromo-2-furyl)-1,3-dioxolane A benzene (58 mL) solution of 4-bromo-2-thiophene carboxaldehyde (10.14 g 57.95 mmol), ethylene glycol (9.70 mL, 173.85 mmol) and p-toluenesulfonic acid monohydrate (1.10 g, 5.79 mmol) was refluxed with azeotropic removal of $H_2O$ for 6 h and then cooled to ambient temperature. The reaction mixture was diluted with $Et_2O$ and the organics were washed with sat'd $NaHCO_3$, brine and then dried ($MgSO_4$), filtered and concentrated. Chromatography on silica gel using 95:5 Hexanes:EtOAc eluted the product to provide the title compound upon concentration as a yellow oil (12.69 g 100% yield): $^1$H NMR (CDCl$_3$, 400 MHz) δ 7.45 (s, 1H), 6.52 (s, 1H), 5.92 (s, 1H), 4.17–4.00 (m, 4H).

B. 5-formyl-3-furoic acid

An $Et_2O$ solution of the 2-(4-bromo-2-furyl)-1,3-dioxolane (12.69 g, 57.95 mmol) was cooled to −78° C. and n-butyl lithium (23.18 mL of a 2.5M sol'n in hexane, 57.95 mmol) was slowly added over 20 min. The anion was stirred at −78° C. for 5 min and then $CO_2$ was bubbled through the reaction as it warmed to ambient temperature. The reaction mixture was poured onto 2 N HCl (100 mL) and vigorously stirred for 30 min and the precipitate filtered, collected and dried to give 5.06 g of a brick red solid (62% yield): $^1$H NMR (CDCl$_3$, 400 MHz) δ 9.73 (s, 1H), 8.31 (s, 1H), 7.57 (s, 1H)

C. 5-{(9aS)-3-(ethoxycarbonyl)-2-[2-(4-fluorophenyl)ethyl]-5-oxo-7,8,9,9a-tetrahydro-5H-pyrido[2,3-a]pyrrolizin-4-yl}-3-furoic acid A DMF (10 mL) solution of tert-Butyl (2S)-2-(3-ethoxy-3-oxopropanoyl)-1-pyrrolidinecarboxylate (2.85 g, 9.99 mmol), 5-formyl-3-furoic acid (1.40 g, 9.99 mmol) and piperidine (0.494 mL, 5.00 mmol) was heated to 80° C. for 45 min and then cooled to ambient temperature. The reaction mixture was diluted with $Et_2O$ and washed 1 N HCl, 2× $H_2O$, 1× brine and the organics dried ($Na_2SO_4$), filtered and concentrated to a brown residue. The Knoevenagel product (4.07 g, 9.99 mmol) and ethyl (2Z)-3-amino-5-(4-fluorophenyl)-2-pentenoate (2.37 g, 9.99 mmol) were heated to 110° C. for 1.5 h and then cooled to ambient temperature. The glassy solid was redissolved in $CH_3CN$ (20 mL) and $H_2O$ (20 mL) followed by addition of ceric ammonium nitrate (10.95 g, 19.98 mmol). The reaction mixture stirred for 45 min at ambient temperature and then $Et_2O$ was added and the organics extracted and washed 1× $H_2O$, 1× brine, and then dried ($Na_2SO_4$), filtered and concentrated to a dark tan solid. The solid from the previous reaction was subjected to TFA (15 mL in 4 mL $CH_2Cl_2$) for 1 h and then concentrated. The residue was redissolved in $CH_2Cl_2$ (20 mL) and treated with $Et_3N$ (12 mL). After 16 h the reaction mixture was concentrated to a brown foam. The residue was redissolved in $CHCl_3$ and washed 1× pH 4.5 buffer, 1× brine and the organics dried ($Na_2SO_4$), filtered and concentrated. Chromatography on silica gel using 9:1 EtOAc:MeOH eluted the desired compound as a tan solid (2.06 g, 4.31 mmol) 43% yield: $^1$H NMR (CDCl$_3$, 400 MHz) δ 8.17 (s, 1H), 8.07 (s, 1H), 7.21 (dd, J=8.6, 5.5 Hz, 2H), 6.99 (t, J=8.6 Hz, 2H), 4.73 (dd, J=10.2, 6.1 Hz, 1H), 4.37 (dd, J=10.6, 7.2 Hz, 2H), 3.88–3.76 (m, 1H), 3.47–3.42 (m, 1H), 3.17–3.03 (m, 4H), 2.48–2.32 (m, 3H), 1.42–1.34 (m, 1H), 1.26 (t, J=7.2 Hz, 3H); ESMS m/z 479 (M+H)$^+$, 477 (M−H)$^+$ D. 5-{(9aS)-3-(ethoxycarbonyl)-2-[2-(4-fluorophenyl) ethyl]-5-oxo-7,8,9,9a-tetrahydro-5H-pyrido[2,3-a]pyrrolizin-4-yl}-3-furoic acid (0.100 g, 0.209 mmol) was dissolved in $CH_2Cl_2$. 1-aminoindane (0.037 mL, 0.313 mmol) was added followed by EDCI (0. 048 g, 0.251 mmol) and HOBt (0.034 g, 0.251 mmol). After 14 h of stirring at ambient temperature the reaction mixture was poured onto 5% HCl solution and extracted with $CH_2Cl_2$. The organics were washed with sat'd $NaHCO_3$, brine and then dried ($Na_2SO_4$), filtered and concentrated to a brown residue. Chromatography on silica gel using 4:1 EtOAc:Hexanes eluted the product to provide the title compound upon concentration as a white solid (0.062 g, 0.105 mmol, 50% yield): $^1$H NMR (CDCl$_3$, 400 MHz) δ 8.12 (s, 1H), 8.11 (d, J=9.5 Hz, 1H), 7.32 (m, 1H), 7.25–7.15 (m, 5H), 6.96 (t, J=8.6 Hz, 2H), 6.32 (m, 1H), 5.69 (dd, J=15.5, 7.7 Hz, 1H), 4.65 (dd, J=10.4, 6.2 Hz, 1H), 4.37 (dd, J=14.2, 7.0), 3.73–3.63 (m, 1H), 3.44–3.38 (m, 1H), 3.17–3.01 (m, 5H), 2.92–2.83 (m, 1H), 2.68–2.60 (m, 1H), 2.48–2.40 (m,1H), 2.37–2.25 (m, 2H), 1.96–1.86 (m, 1H), 1.38–1.30 (m, 1H), 1.27 (t, J=7.1 Hz, 3H); ESMS m/z 594 (M+H)$^+$, 592 (M−H)$^+$; Anal. Calcd. For C35H32FN3O5.½H2O: C, 69.75; H, 5.52; N, 6.97; found: C, 69.58; H, 5.43; N, 7.05.

EXAMPLE 18

Ethyl(9aS)-4-(5-{[(1R)-2,3-dihydro-1H-inden-1-ylamino]carbonyl}-2-thienyl)-2-[2-(4-fluorophenyl)ethyl]-5-oxo-7,8,9,9a-tetrahydro-5H-pyrido[2,3-a]pyrrolizine-3-carboxylate.

A. 5-{(9aS)-3-(ethoxycarbonyl)-2-[2-(4-fluorophenyl)ethyl]-5-oxo-7,8,9,9a-tetrahydro-5H-pyrido[2,3-a]pyrrolizin-4-yl}-2-thiophenecarboxylic acid A DMF (10 mL) solution of tert-Butyl (2S)-2-(3-ethoxy-3-oxopropanoyl)-1-pyrrolidinecarboxylate (2.85 g, 9.99 mmol), 2-formyl-5-thiophene carboxylic acid (1.56 g, 9.99 mmol) and piperidine (0.494 mL, 5.00 mmol) was heated to 80° C. for 45 min and then cooled to ambient temperature. The reaction mixture was diluted with Et$_2$O and washed 1 N HCl, 2× H$_2$O, 1× brine and the organics dried (Na$_2$SO$_4$), filtered and concentrated to a brown residue. The Knoevenagel product (4.23 g, 9.99 mmol) and ethyl (2Z)-3-amino-5-(4-fluorophenyl)-2-pentenoate (2.37 g, 9.99 mmol) were heated to 110° C. for 1.5 h and then cooled to ambient temperature. The glassy solid was redissolved in CH$_3$CN (20 mL) and H$_2$O (20 mL) followed by addition of ceric ammonium nitrate (10.95 g, 19.98 mmol). The reaction mixture stirred for 45 min at ambient temperature and then Et$_2$O was added and the organics extracted and washed 1× H2O, 1× brine, and then dried (Na$_2$SO$_4$), filtered and concentrated to a dark tan solid. The solid from the previous reaction was subjected to TFA (15 mL in 4 mL CH$_2$Cl$_2$) for 1 h and then concentrated. The residue was redissolved in CH$_2$Cl$_2$ (20 mL) and treated with Et$_3$N (12 mL). After 16 h the reaction mixture was concentrated to a brown foam. The residue was redissolved in CHCl$_3$ and washed 1× pH 4.5 buffer, 1× brine and the organics dried (Na$_2$SO$_4$), filtered and concentrated. Chromatography on silica gel using 9:1 EtOAc:MeOH eluted the desired compound as a yellow solid (2.16 g, 4.37 mmol) 44% yield: $^1$H NMR (CDCl$_3$, 400 MHz) δ 7.70 (d, J=3.7 Hz, 1H), 7.19–7.14 (m, 3H), 6.96 (t J=8.7 Hz, 2H), 4.70 (dd, J=10.2, 6.2 Hz, 1H), 4.15 (dd, J=14.2, 7.1 Hz, 2H), 3.81–3.71 (m, 1H), 3.43–3.35 (m, 1H), 3.18–3.06 (m, 4H), 2.51–2.40 (m, 1H), 2.39–2.26 (m, 2H), 1.11 (t, J=7.1 Hz, 3H).

B. 5-{(9aS)-3-(ethoxycarbonyl)-2-[2-(4-fluorophenyl)ethyl]-5-oxo-7,8,9,9a-tetrahydro-5H-pyrido[2,3-a]pyrrolizin-4-yl}-2-thiophenecarboxylic acid (0.100 g, 0.202 mmol) was dissolved in CH$_2$Cl$_2$ (2 mL). R-(−)-1-aminoindane (0.026 mL, 0.303 mmol) was added followed by EDCI (0.047 g, 0.243 mmol) and HOBt (0.033 g, 0.243 mmol). After 14 h of stirring at ambient temperature the reaction mixture was poured onto 5% HCl solution and extracted with CH$_2$Cl$_2$. The organics were washed with sat'd NaHCO$_3$, brine and then dried (Na$_2$SO$_4$), filtered and concentrated to a brown residue. Chromatography on silica gel using 4:1 EtOAc:Hexanes eluted the product to provide the title compound upon concentration as a white solid (0.066 g, 0.108 mmol, 54% yield): $^1$H NMR (CDCl$_3$, 400 MHz) δ 7.48 (d, J=3.7 Hz, 1H), 7.36 (d, J=6.7 Hz, 1H), 7.28–7.20 (m, 2H), 7.19–15 (m, 3H), 6.97 (t, J=8.6 Hz, 2H), 6.24–6.20 (m, 1H), 5.67 (dd, J=15.3, 7.6 Hz, 1H), 4.69 (dd, J=10.3, 6.4 Hz, 1H), 4.19 (dd, J=14.3, 7.1), 3.76–3.66 (m, 1H), 3.42–3.36 (m, 1H), 3.18–3.01 (m, 5H), 2.96–2.87 (m, 1H), 2.71–2.66 (m, 1H), 2.48–2.40 (m, 1H), 2.37–2.25 (m, 2H), 1.96–1.86 (m, 1H), 1.42–1.35 (m, 1H), 1.13 (t, J=7.1 Hz, 3H); ESMS m/z 610 (M+H)$^+$, 608 (M−H)$^+$; Anal. Calcd. For C35H32F1N3O4S.½H2O: C 67.94 H, 5.38; N, 6.79; found C, 68.09 H 5.31 N 6.80.

EXAMPLE 19

Ethyl (9aS)-4-(5-{[(1R)-2,3-dihydro-1H-inden-1-ylamino]carbonyl}-1,3-thiazol-2-yl)-2-(4-fluorobenzyl)-5-oxo-7,8,9,9a-tetrahydro-5H-pyrido[2,3-a]pyrrolizine-3-carboxylate A. 2-(1,3-dioxolan-2-yl)-1,3-thiazole A benzene (10 mL) solution of 2-thiazole carboxaldehyde (5.00 g 44.19 mmol), ethylene glycol (7.40 mL, 132.58 mmol) and p-toluenesulfonic acid monohydrate (1.50 g, 7.89 mmol) was refluxed with azeotropic removal of H$_2$O for 3 h and then cooled to ambient temperature. The reaction mixture was diluted with Et$_2$O and the organics washed with sat'd NaHCO$_3$, brine and then dried (MgSO$_4$), filtered and concentrated to provide the title compound as a reddish oil. $^1$H NMR (CDCl$_3$, 400 MHz) δ 7.79 (d, J=3.1 Hz, 1H), 7.35 (d, J=3.1 Hz, 1H), 6.13 (s, 1H), 4.16–4.01 (m, 4H).

B. 2-(1,3-dioxolan-2-yl)-1,3-thiazole-5-carboxylic acid

A THF (10 mL) solution of 2-(1,3-dioxolan-2-yl)-1,3-thiazole (3.80 g, 24.17 mmol) under N$_2$ was cooled to −78° C. with a dry ice/acetone bath. nBuLi (9.67 mL of a 2.5M solution in Hexane, 24.17 mmol) was added dropwise over 10 min. The reaction mixture was stirred at −78° C. for 10 min and then CO$_2$ was bubbled through the reaction as it warmed to ambient temperature. After 30 min 2N HCl was added and the solution stirred for 45 min. The organics were extracted twice with Et$_2$O and then washed with H2O, brine and dried (Na$_2$SO$_4$), filtered and concentrated to give the title compound (3.89 g, 19.33 mmol, 80% yield) as an off-white solid. $^1$H NMR (DMSO-d6, 400 MHz) δ 8.31 (s, 1H), 6.05 (s, 1H), 4.06–3.96 (m, 4H).

C. 2-formyl-1,3-thiazole-5-carboxylic acid 2-(1,3-dioxolan-2-yl)-1,3-thiazole-5-carboxylic acid (1.40 g, 6.96 mmol) was dissolved in 15 mL of 6N HCl and heated to reflux for 30 min and then cooled to ambient temperature. The organics were extracted twice with EtOAc and then dried(Na$_2$SO$_4$), filtered and concentrated to give the title compound (1.00 g, 6.36 mmol, 91% yield) as an orange solid. $^1$H NMR (CDCl$_3$, 400 MHz) δ 10.0 (s, 1H), 8.66 (s, 1H), 6.70–6.00 (bs, 1H).

D. A benzene (15 mL) solution of ethyl-4-[(tert-butoxycarbonyl)(methyl)amino]-3-oxobutanoate (1.80 g, 6.31 mmol), 2-formyl-1,3-thiazole-5-carboxylic acid (0.992 g, 6.31 mmol) and piperidine (0.312 mL, 3.16 mmol) was refluxed with azeotropic removal of H$_2$O for 1.5 h and then cooled to ambient temperature and concentrated. The residue was redissolved in EtOAc and washed with 1 N HCl, 2× H$_2$O, 1× brine and the organics dried (Na$_2$SO$_4$), filtered and concentrated to an amorphous brown solid. The Knoevenagel product (2.68 g, 6.31 mmol) and ethyl (2Z)-3-amino-4-(4-fluorophenyl)-2-butenoate (1.41 g, 6.31 mmol) were heated to 110° C. for 2 h and then cooled to ambient temperature. The glassy dihydropyridine solid (0.200 g, 0.318 mmol) was redissolved in CH$_2$Cl$_2$ (2 mL). R-(−)-1-aminoindane (0.041 mL, 0.476 mmol) was added followed by EDCI (0.073 g, 0.381 mmol) and HOBt (0.052 g, 0.381 mmol). After 14 h of stirring at ambient temperature the reaction mixture was poured onto 5% HCl solution and extracted with CH$_2$Cl$_2$. The organics were washed with sat'd NaHCO$_3$, brine and then dried (Na$_2$SO$_4$), filtered and concentrated to a brown residue. The residue was redissolved in CH$_3$CN (2 mL) and H$_2$O (2 mL) followed by addition of ceric ammonium nitrate (0.348 g, 0.635 mmol). The reaction mixture stirred for 45 min at ambient temperature and then Et$_2$O was added and the organics extracted and washed 1× H$_2$O, 1× brine, and then dried (Na$_2$SO$_4$), filtered and concentrated to a dark brown solid. The solid was subjected to TFA (6 mL in 3 mL CH$_2$Cl$_2$) for 1 h and then concentrated. The residue was redissolved in CH$_2$Cl$_2$ (15 mL) and treated with Et$_3$N (5 mL). After 16 h the reaction mixture was concentrated to a brown foam. The residue was redissolved in EtOAc and washed with 5% HCl solution and extracted with CH$_2$Cl$_2$. The organics were washed with sat'd NaHCO$_3$, brine and then dried (Na$_2$SO$_4$), filtered and concentrated to a brown residue. Chromatography on silica gel using 2:1 EtOAc:Hexanes eluted the title compound (0.011 g, 0.018 mmol, 6% yield based upon dihydropyridine used in the amide coupling) after concentration as an off-white solid. $^1$H NMR (CDCl$_3$, 400MHz) δ 8.26 (s, 1H), 7.33 (d, J=7.2 Hz, 1H), 7.26–7.13 (m, 5H), 6.91 (t, J=8.7 Hz, 2H), 6.24–6.14 (m, 1H), 5.64 (dd, J=14.8, 7.4 Hz, 1H), 4.71 (dd, J=10.2, 6.3 Hz, 1H), 4.27 (d, J=14.6 Hz, 2H), 4.07 (dd, J=14.1, 7.0 Hz, 2H), 3.78–3.68 (m, 1H), 3.44–3.38 (m, 1H), 3.10–2.99 (m, 1H), 2.94–2.86 (m, 1H), 2.70–2.62 (m, 1H), 2.48–2.40 (m, 1H), 2.37–2.25 (m, 2H), 1.96–1.86 (m, 1H), 1.42–1.35 (m, 1H), 1.13 (t, J=7.1 Hz, 3H); ESMS m/z 597 (M+H)$^+$, 595 (M−H)$^+$.

EXAMPLE 20

4-[(9aS)-2-(4-fluorobenzyl)-5-oxo-7,8,9,9a-tetrahydro-5H-pyrido[2,3-a]pyrrolizin-4-yl]-N-[(1R)-2,3-dihdro-1H-inden-1-yl]benzamide A. Allyl 4-(4-fluorophenyl)-3-oxobutanoate To a CH$_2$Cl$_2$ (210 mL) solution of 4-fluorophenyl acetic acid (32.28 g, 209.42 mmol) at 0° C. was added DMAP (25.58 g, 209.42 mmol), and Meldrum's Acid (30.18 g, 209.42 mmol) followed by DCC (43.21 g, 209.42 mmol). The reaction mixture was warmed to ambient temperature and stirred for 4 h. The reaction was filtered to remove the DCU and the filtrate washed with 1N HCl, H$_2$O, and brine. The organics were dried (Na$_2$SO$_4$), filtered and concentrated to a yellow oil. The residue was redissolved in THF (200 mL) and allyl alcohol (14.38 mL, 211.51 mmol). The reaction mixture was refluxed for 3 h and then concentrated to deliver 47 g (95% yield) of the title compound as a pale yellow oil and used without further purification.

$^1$H NMR (CDCl$_3$, 400 MHz) δ 7.13 (dd, J=8.4, 5.2 Hz, 2H), 7.00 (t, J=8.4 Hz, 2H), 5.91–5.82 (m, 1H), 5.32–5.22 (m, 2H), 4.59 (d, J=5.9 Hz, 2H), 3.78 (s, 2H), 3.46 (s, 2H).

B. Allyl (2Z)-3-amino-4-(4-fluorophenyl)-2-butenoate

Allyl 4-(4-fluorophenyl)-3-oxobutanoate (47 g, 198.95 mmol) and ammonium acetate (46.00 g, 596.85 mmol) were refluxed in benzene (250 mL) for 2 h with azeotropic removal of H$_2$O and then cooled and concentrated. The residue was redissolved in Et$_2$O and the organics washed with 1N HCl (2×), H$_2$O, brine, and then dried (Na$_2$SO$_4$), filtered and concentrated to give 47 g (100% yield) of the title compound as a yellow oil. $^1$H NMR (CDCl$_3$, 400 MHz) δ 7.17 (dd, J=8.4, 5.2 Hz, 2H), 6.99 (t, J=8.6 Hz, 2H), 5.28 (dd, J=17.2, 1.6 Hz, 1H), 5.18 (dd, J=10.3, 1.0 Hz, 1H), 4.61 (s, 1H), 4.55 (d, J=5.6 Hz, 2H), 3.41 (s, 2H).

C. 4-[(9aS)-2-(4-fluorobenzyl)-5-oxo-7,8,9,9a-tetrahydro-5H-pyrido[2,3-a]pyrrolizin-4-yl]benzoic acid A benzene (10 mL) solution of tert-Butyl (2S)-2-(3-ethoxy-3-oxopropanoyl)-1-pyrrolidinecarboxylate (1.93 g, 6.77 mmol), 4-carboxybenzaldehyde (1.01 g, 6.77 mmol) and piperidine (0.335 mL, 3.39 mmol) was refluxed with azeotropic removal of H$_2$O for 1.5 h and then cooled to ambient temperature and concentrated. The residue was redissolved in EtOAc and washed with 1×1 N HCl, 2× H$_2$O, 1× brine and the organics dried (Na$_2$SO$_4$), filtered and concentrated to an amorphous brown solid. The Knoevenagel product (2.83 g, 6.77 mmol) and allyl (2Z)-3-amino-4-(4-fluorophenyl)-2-butenoate (1.59 g, 6.77 mmol) were heated to 110° C. for 1.5 h and then cooled to ambient temperature. The dihydropyridine product (2.35 g, 3.71 mmol) was redissolved in CH$_3$CN (10 mL) and to this was added morpholine (0.648 mL, 3.71 mmol) and Pd(PPh$_3$)$_4$ (0.215 g, 0.186 mmol). The reaction mixture was stirred at ambient temperature for 1.5 h and then filtered through Celite and concentrated. The residue was redissolved in toluene and heated to reflux for 6 h. The reaction was concentrated and redissolved in CH$_3$CN (10 mL) and H$_2$O (10 mL) followed by addition of ceric ammonium nitrate (4.06 g, 7.40 mmol). The reaction mixture stirred for 15 min at ambient temperature and then EtOAc was added and the organics extracted and washed 1× H$_2$O, 1× brine, and then dried (Na$_2$SO4), filtered and concentrated to a dark tan solid. The solid was subjected to TFA (4.5 mL in 1 mL CH$_2$Cl$_2$) for 1 h and then concentrated. The residue was redissolved in CH$_2$Cl$_2$ (5 mL) and treated with Et$_3$N (3 mL). After 16 h the reaction mixture was concentrated to a brown foam. The residue was redissolved in EtOAc and washed 1× pH 4.5 buffer, 1×brine and the organics dried (Na$_2$SO$_4$), filtered and concentrated to yield 0.800 g (54% yield) of the title compound as a tan solid. $^1$H NMR (CDCl$_3$, 400 MHz) δ 8.10 (d, J=8.0 Hz, 2H), 7.63 (d, J=8.3 Hz), 7.25 (t, J=7.3 Hz, 2H), 7.12 (s, 1H), 6.99 (t, J=8.6 Hz, 2H), 4.78–4.74 (m, 1H), 4.25 (s, 2H), 3.78–3.71 (m, 1H), 3.44–3.38 (m, 1H), 2.52–2.47 (m, 1H), 2.37–2.31 (m, 2H), 1.44–1.39 (m, 1H); ESMS m/z 403 (M+H)$^+$, 401 (M−H)$^+$.

D. 4-[(9aS)-2-(4-fluorobenzyl)-5-oxo-7,8,9,9a-tetrahydro-5H-pyrido[2,3-a]pyrrolizin-4-yl]benzoic acid (0.800 g, 1.99 mmol) was dissolved in CH$_2$Cl$_2$ (2 mL). R-(−)-1-aminoindane (0.254 mL, 2.98 mmol) was added followed by EDCI (0.457 g, 2.39 mmol) and HOBt (0.322 g, 2.39 mmol). After 14 h of stirring at ambient temperature the reaction mixture was poured onto 5% HCl solution and extracted with CH$_2$Cl$_2$. The organics were washed with sat'd NaHCO$_3$, brine and then dried (Na$_2$SO$_4$), filtered and concentrated to a brown residue.

Chromatography on silica gel using 2:1 EtOAc:Hexanes eluted the product to provide the title compound upon concentration as a white solid (0.300 g, 0.580 mmol, 29% yield): $^1$H NMR (CDCl$_3$, 400 MHz) δ 7.84 (d, J=8.1 Hz, 2H), 7.64 (d, J=8.1 Hz, 2H), 7.35–7.23 (m, 6H), 7.11 (s, 1H), 7.00 (t, J=8.6 Hz, 2H), 6.36–6.34 (m, 1H), 5.70 (dd, J=15.4, 7.6 Hz, 1H), 4.70 (dd, J=10.2, 6.2 Hz, 1H), 4.23 (s, 2H), 3.73–3.68 (m, 1H), 3.42–3.36 (m, 1H), 3.05–2.89 (m, 2H), 2.73–2.67 (m, 1H), 2.49–2.40 (m, 1H), 2.37–2.31 (m, 2H), 1.98–1.84 (m, 1H), 1.42–1.35 (m, 1H); ESMS m/z 518 (M+H)$^+$, 516 (M–H)$^+$.

EXAMPLE 21

Ethyl 4-(4-{[(1R)-2,3-dihydro-1H-inden-1-ylamino]carbonyl}-1,3-oxazol-2-yl)-5-oxo-2-{2-[4-(trifluoromethyl)phenyl]ethyl}-8,9-dihydro-5H,7H-pyrazolo[1', 2':1,2]pyrazolo[3,4-b]pyridine-3-carboxylate A. Ethyl 4-[4-(ethoxycarbonyl)-1,3-oxazol-2-yl]-5-oxo-2-{2-[4-(trifluoromethyl)phenyl]ethyl}-8,9-dihydro-5H,7H-pyrazolo[1'2':1,2]pyrazolo[3,4-b]pyridine-3-carboxylate An EtOH (4 mL) mixture of ethyl 5-formyl-3-furaote (ref. Panek, James S.;Beresis, Richard T.; *J. Org. Chem.*, 1996, 61, 6496–6497) (0.293 g, 1.73 mmol), ethyl 3-oxo-5-[4-(trifluoromethyl)phenyl]pentanoate (0.500 g, 1.73 mmol), 3-amino-6,7-dihydro-1H, 5H-pyrazolo[1,2-a]pyrazol-1-one hydrochloride (refs. R. B. Greenwald, U.S. Pat. No. 4,128, 425 and E. E. Boros, F. Bouvier, S. Randhawa and M. H. Rabinowitz, *J. Heterocyclic Chem.*, 2001, 38, 613–616.) (0.305 g, 1.73 mmol) and NaOEt (0.118 g, 1.73) was heated at reflux for 24 h. The reaction mixture was diluted with H$_2$O and the resulting precipitate collected by filtration and dried to give a tan solid (0.750 g, 1.34 mmol, 77% crude). The dihydropyridine was redissolved in CH$_3$CN (4 mL) and H$_2$O (2 mL) and ceric ammonium nitrate (1.47 g, 2.68 mmol) was added. The reaction mixture stirred at ambient temperature for 30 min and then H$_2$O (5 mL) was added and the organics extracted with EtOAc (2×25 mL) and then dried (Na$_2$SO$_4$), filtered and concentrated. Chromatography on silica gel using 4% MeOH/96% EtOAc eluted the product. After concentration, the title compound (0.400 g, 0.717 mmol, 96% yield) was isolated as a yellow solid: $^1$H NMR (CDCl$_3$, 400 MHz) δ 8.42 (s, 1H), 7.50 (d, J=8 Hz, 2H), 7.31 (d, J=8 Hz, 2H), 4.37 (dd, J=14.3, 7.2 Hz, 2H), 4.23 (dd, J=14.1, 7.1 Hz, 2H), 3.97 (t, J=7.1 Hz, 2H), 3.90 (t, J=6.9 Hz, 2H), 3.28–3.24 (m, 2H), 3.16–3.12 (m, 2H), 2.67–2.63 (m, 2H), 1.35 (t, J=7.1 Hz, 3H), 1.14 (t, J=7.0 Hz).

B. 2-(3-(ethoxycarbonyl)-5-oxo-2-{2-[4-(trifluoromethyl)phenyl]ethyl}-8,9-dihydro-5H,7H-pyrazolo[1', 2':1,2]pyrazolo[3,4-b]pyridin-4-yl)-1,3-oxazole-4-carboxylic acid A THF (4 mL) of ethyl 4-[4-(ethoxycarbonyl)-1,3-oxazol-2-yl]-5-oxo-2-{2-[4-(trifluoromethyl)phenyl]ethyl}-8,9-dihydro-5H,7H-pyrazolo[1'2':1,2]pyrazolo[3,4-b]pyridine-3-carboxylate (0.400 g, 0.717 mmol), 0.717 mL of 1 N NaOH and EtOH (0.717 mL) was stirred for 6 h at ambient temperature and then concentrated. The residue was treated with 1 N HCl until acidic and the organics extracted with EtOAc (2×) and then dried (Na$_2$SO$_4$), filtered and concentrated to a yellowish-orange solid and used in the proceeded step with no further purification: $^1$H NMR (CDCl$_3$, 400 MHz) δ 8.39 (s, 1H), 7.51 (d, J=8.1 Hz, 2H), 7.29 (d, J=7.9 Hz, 2H), 4.12–4.00 (m, 6H)), 3.18–3.08 (m, 4H), 2.81–2.74 (m, 2H), 1.00 (t, J=7.2 Hz, 3H).

C. 2-(3-(ethoxycarbonyl)-5-oxo-2-{2-[4-(trifluoromethyl)phenyl]ethyl}-8,9-dihydro-5H,7H-pyrazolo[1',2':1,2]pyrazolo[3,4-b]pyridin-4-yl)-1,3-oxazole-4-carboxylic acid (0.076 g, 0.143 mmol) was dissolved in CH$_2$Cl$_2$ (2 mL). R-(–)-1-aminoindane (0.018 mL, 0.215 mmol) was added followed by EDCI (0.033 g, 0.172 mmol) and HOBt (0.023 g, 0.172 mmol). After 14 h of stirring at ambient temperature the reaction mixture was poured onto 5% HCl solution and extracted with CH$_2$Cl$_2$. The organics were washed with sat'd NaHCO$_3$, brine and then dried (Na$_2$SO$_4$), filtered and concentrated to a yellow residue. Chromatography on silica gel using 9:1 EtOAc:Hexanes eluted the product to provide the title compound upon concentration as a white solid (0.046 g, 0.0.071 mmol, 50% yield): $^1$H NMR (CDCl$_3$, 400 MHz) 8.44 (s, 1H), 7.49 (d, J=7.9 Hz, 2H), 7.29–7.12 (m, 6H), 5.64 (dd, J=15.7, 7.6 Hz, 1H), 4.58 (d J=5.9 Hz, 2H), 4.07 (dd, J=14.3, 7.0 Hz, 2H), 3.99–3.91 (m, 4H), 3.24–3.10 (m, 4H), 3.04–2.97 (m, 1H), 2.92–2.84 (m, 1H), 1.93–1.87 (m, 1H), 1.04 (t, J=7.1 Hz, 3H); ESMS m/z 646 (M+H)$^+$, 644 (M–H)$^+$ Anal. Calcd. For C34H30F3N5O5.½H2O: C, 62.38; H, 4.77; N, 10.70; found: C, 62.59; H, 4.74; N, 10.58.

EXAMPLE 22

Ethyl(9aS)-2-(2,4-difluorobenzyl)-4-(5-{[(1R)-2,3-dihydro-1H-inden-1-ylamino]carbonyl}-2-pyrazinyl)-5-oxo-7,8,9,9a-tetrahydro-5H-pyrido[2,3-a]pyrrolizine-3-carboxylate A. Ethyl 5-methyl-2-pyrazinecarboxylate 5-methyl pyrazine-2-carboxylic acid (6.65 g, 48.14 mmol) was refluxed in 50 mL of EtOH containing a few drops of H$_2$SO$_4$ for 5 h and then cooled and concentrated. The residue was redissolved in EtOAc and washed 1× NaHCO$_3$, 1× brine and the organics dried (Na$_2$SO$_4$), filtered and concentrated to give the title compound (7.05 g, 42.42 mmol, 88% yield) as a pale yellow oil: $^1$H NMR (CDCl$_3$, 400 MHz) δ 9.16 (s, 1H), 8.55 (s, 1H), 4.47 (dd, J=14.1, 7.1 Hz), 2.64 (s, 3H), 1.42 (t, J=7.2 Hz, 3H).

B. Ethyl 5-(bromomethyl)-2-pyrazinecarboxylate

Ethyl 5-methyl-2-pyrazinecarboxylate (10.0 g, 60.18 mmol), benzoyl peroxide (1.46 g, 6.02 mmol) and N-bromo succinimide (11.78 g, 66.19 mmol) in 80 mL CCl$_4$ was heated to reflux while a 75 W tungsten lamp was shining on the reaction mixture. After 4 h the reaction mixture was cooled and the precipitate filtered off. The red filtrate was concentrated and the residue redissolved in EtOAc and washed with sat'd NaHCO$_3$, 5% Na$_2$S$_2$O$_3$, brine and the organics dried (Na$_2$SO$_4$), filtered and concentrated. Chromatography on silica gel using 1:1 Hexanes:EtOAc eluted the product. After concentration the title compound (6.64 g, 27.08 mmol, 45% yield) was isolated as a yellow oil: $^1$H NMR (CDCl$_3$, 400 MHz) δ 9.22 (s, 1H), 8.80 (s, 1H), 4.58 (s, 2H), 4.49 (dd, J=14.3, 7.1 Hz, 2H), 1.43 (t, J=7.2 Hz, 3H).

C. Ethyl 5-[(nitrooxy)methyl]-2-pyrazinecarboxylate

Ethyl 5-(bromomethyl)-2-pyrazinecarboxylate (6.64 g, 27.08 mmol) and AgNO$_3$ (6.9 g, 40.62 mmol) were stirred at ambient temperature in a 24 mL acetone/16 mL H$_2$O solution for 3.5 h. The reaction was filtered off over Celite and the filtrate concentrated to an oil (5.56 g, 24.47 mmol, 90% yield) and used without further purification: ¹H NMR (CDCl₃, 400 MHz) δ 9.28 (s, 1H), 8.78 (s, 1H), 5.65 (s, 2H), 4.50 (dd, J=14.1, 7.0 Hz, 2H), 1.43 (t, J=7.1 Hz, 3H).

D. Allyl 4-(2,4-difluorophenyl)-3-oxobutanoate

To a CH₂Cl₂ (40 mL) solution of 2,4-difluorophenyl acetic acid (6.89 g, 40.03 mmol) at 0° C. was added DMAP (4.89 g, 40.03 mmol), and Meldrum's Acid (5.77 g, 40.03 mmol) followed by DCC (8.26 g, 40.03 mmol). The reaction mixture was warmed to ambient temperature and stirred for 4 h. The reaction was filtered to remove the DCU and the filtrate washed with 1N HCl, H₂O, and brine. The organics were dried (Na₂SO₄), filtered and concentrated to a yellow oil. The residue was redissolved in THF (40 mL) and allyl alcohol (8 mL, 117.63 mmol). The reaction mixture was refluxed for 3 h and then concentrated to deliver 9.67 g (95% yield) of the title compound as a pale yellow oil and used without further purification. ¹H NMR (CDCl₃, 400 MHz) δ 7.16–7.10 (m, 1H), 6.82 (dd, J=16.6, 8.2 Hz, 2H), 5.91–5.82 (m, 1H), 5.31 (dd, J=17.3, 1.4 Hz, 1H), 5.25 (dd, J=10.3, 1.0 Hz, 1H), 4.61 (d, J=5.8 Hz, 2H), 3.82 (s, 2H), 3.52 (s, 2H).

E. Allyl (2E)-3-amino-4-(2,4-difluorophenyl)-2-butenoate

Allyl 4-(2,4-difluorophenyl)-3-oxobutanoate (5.0 g, 19.67 mmol) and ammonium acetate (7.58 g, 98.33 mmol) were refluxed in toluene (20 mL) for 2 h with azeotropic removal of H₂O and then cooled and concentrated. The residue was redissolved in Et₂O and the organics washed with 1N HCl (2×), H₂O, brine, and then dried (Na₂SO₄), filtered and concentrated to give 5.0 g (100% yield) of the title compound as a yellow oil: ¹H NMR (CDCl₃, 400 MHz) δ 7.25–7.14 (m, 1H), 6.63 (dd, J=16.1, 7.9 Hz, 2H), 5.97–5.88 (m, 1H), 5.28 (dd, J=17.2, 1.5 Hz, 1H), 5.19 (dd, J=10.2, 1.1 Hz, 1H), 4.60 (s, 1H), 4.55 (d, J=5.7 Hz, 2H), 3.43 (s, 2H).

F. 5-allyl 3-ethyl 2-[(2S)-1-(tert-butoxycarbonyl)pyrrolidinyl]-6-(2,4-difluorobenzyl)-4-[5-(ethoxycarbonyl)-2-pyrazinyl]-1,4-dihydro-3,5-pyridinecarboxylate A toluene (20 mL) solution of tert-Butyl (2S)-2-(3-ethoxy-3-oxopropanoyl)-1-pyrrolidinecarboxylate (5.63 g, 19.74 mmol), ethyl 5-[(nitrooxy)methyl]-2-pyrazinecarboxylate (4.49 g, 19.74 mmol), allyl (2E)-3-amino-4-(2,4-difluorophenyl)-2-butenoate (5.00 g, 19.74 mmol) and piperidine (2.05 mL, 20.73 mmol) was heated to 80° C. for 3.0 h and then cooled to ambient temperature and concentrated. The residue was redissolved in EtOAc and the organics washed with 0.5 N HCl, brine and then dried (Na2SO4), filtered and concentrated. Chromatography on silica gel using 3:1 Hexanes:EtOAc eluted the product which upon concentrating was a yellow solid (6.73 g, 9.86 mmol, 50% yield): ESMS m/z 683 (M+H)⁺, 681 (M−H)⁺.

G. Ethyl 5-[2-[(2S)-1-(tert-butoxycarbonyl)pyrrolidinyl]-6-(2,4-difluorobenzyl)-3-(ethoxycarbonyl)-1,4-dihydro-4-pyridinyl]-2-pyrazinecarboxylate 5-allyl 3-ethyl 2-[(2S)-1-(tert-butoxycarbonyl)pyrrolidinyl]-6-(2,4-difluorobenzyl)-4-[5-(ethoxycarbonyl)-2-pyrazinyl]-1,4-dihydro-3,5-pyridinecarboxylate (2.85 g, 4.17 mmol) was dissolved in CH₃CN (10 mL) and to this was added morpholine (0.728 mL, 8.35 mmol) and Pd(PPh₃)₄ (0.241 g, 0.209 mmol). The reaction mixture was stirred at ambient temperature for 1.5 h and then filtered through Celite and concentrated. The residue was redissolved in toluene and heated to reflux for 6 h. The reaction was cooled to ambient temperature and concentrated and used without further purification in the next step: ESMS m/z 599 (M+H)⁺, 597 (M−H)⁺.

H. Ethyl 5-[(9aS)-2-(2,4-difluorobenzyl)-5-oxo-7,8,9,9a-tetrahydro-5H-pyrido[2,3-a]pyrrolizin-4-yl]-2-pyrazinecarboxylate Ethyl 5-[2-[(2S)-1-(tert-butoxycarbonyl)pyrrolidinyl]-6-(2,4-difluorobenzyl)-3-(ethoxycarbonyl)-1,4-dihydro-4-pyridinyl]-2-pyrazinecarboxylate (1.3 g, 2.17 mmol) was dissolved in 8 mL of CH₃CN and 4 mL of H₂O. Ceric ammonium nitrate (2.38 g, 4.34 mmol) was added and the reaction mixture stirred at ambient temperature for 30 min and then EtOAc was added and the organics extracted and washed with H₂O, brine, and then dried (Na₂SO₄), filtered and concentrated to a brown solid. The solid was subjected to TFA (4.5 mL in 1 mL CH₂Cl₂) for 1 h and then concentrated. The residue was redissolved in CH₂Cl₂ (5 mL) and treated with Et₃N (3 mL). After 16 h the reaction mixture was concentrated to a brown foam. The residue was redissolved in EtOAc and washed 1× pH 4.5 buffer, 1× brine and the organics dried (Na₂SO₄), filtered and concentrated to yield 0.250 g (26% yield) of the title compound as a tan solid. ¹H NMR (CDCl₃, 400 MHz) δ 9.41 (s, 1H), 9.34 (s, 1H), 7.58 (s, 1H), 7.26–7.21 (m, 1H), 6.80 (dd, J=16.4, 7.4 Hz, 2H), 4.75 (dd, J=10.3, 6.2 Hz, 1H), 4.51 (dd,J=14.2, 7.1 Hz, 2H), 4.27 (s, 2H), 3.78–3.68 (m, 1H), 3.45–3.39 (m, 1H), 2.54–2.43 (m, 1H), 2.37–2.32 (m, 2H), 1.46–1.38 (m, 1H), 1.23 (t, J=7.2 Hz, 3H); ESMS m/z 451 (M+H)⁺, 449 (M−H)⁺.

I. 5-[(9aS)-2-(2,4-difluorobenzyl)-5-oxo-7,8,9,9a-tetrahydro-5H-pyrido[2,3-a]pyrrolizin-4-yl]-2-pyrazinecarboxylic acid Ethyl 5-[(9aS)-2-(2,4-difluorobenzyl)-5-oxo-7,8,9,9a-tetrahydro-5H-pyrido[2,3-a]pyrrolizin-4-yl]-2-pyrazinecarboxylate (0.250 g, 0.555 mmol) was dissolved in THF (4 mL), H₂O (1 mL) and MeOH (1 mL) and LiOH monohydrate (0.035 g, 0.832 mmol) was added. The reaction mixture was stirred at ambient temperature for 45 min and then acidified to pH 5. The organics were extracted with CH₂Cl₂ and then dried (Na₂SO₄), filtered and concentrated to a white solid (0.200 g, 0.473 mmol, 85% yield): ¹H NMR (CD₃OD, 400 MHz) δ 9.36 (s, 2H), 7.74 (s, 1H), 7.41–7.35 (m, 1H), 6.97–6.91 (m, 2H), 4.86–4.83 (m, 1H), 4.33 (s, 2H), 3.71–3.64 (m, 1H), 3.48–3.41 (m, 1H), 2.46–2.38 (m, 3H), 1.42–1.38 (m, 1H).

J. A DMF (1 mL) solution of 5-[(9aS)-2-(2,4-difluorobenzyl)-5-oxo-7,8,9,9a-tetrahydro-5H-pyrido[2,3-a]pyrrolizin-4-yl]-2-pyrazinecarboxylic acid (0.100 g, 0.249 mmol), EDCI (0.057 g, 0.298 mmol), HOBt (0.040 g, 0.298 mmol), and R-(−)-1-amino indane (0.048 mL, 0.373 mmol) was stirred at ambient temperature for 2.5 h. The reaction mixture was diluted with H₂O and the precipitate filtered off, collected and dried to give the title compound (0.060 g, 0.098 mmol, 40% yield) as an off-white solid: ¹H NMR (CDCl₃, 400 MHz) δ 9.49 (s, 1H), 9.23 (s, 1H), 8.07 (m, 1H), 7.66 (s, 1H), 7.31–7.18 (m, 5H), 6.83 (dd, J=15.7, 7.6 Hz, 2H), 5.69 (dd, J=15.5, 7.1 Hz, 1H), 4.75 (dd, J=10.4, 6.4 Hz, 1H), 4.28 (s, 2H), 4.10 (dd, J=14.3, 7.3 Hz, 2H), 3.77–3.69 (m, 1H), 3.45–3.39 (m, 1H), 3.08–3.03 (m, 1H), 2.97–2.89 (m, 1H), 2.78–2.67 (m, 1H), 2.53–2.43 (m, 1H), 2.39–2.25 (m, 2H), 2.05–1.91 (m, 1H), 1.43–1.36 (m, 1H), 1.23 (t, J=7.2 Hz, 3H); ESMS m/z 538 (M+H)$^+$, 536 (M–H)$^+$; Anal. Calcd. For C31H25F2N5O2. ¼H$_2$O: C, 68.69; H, 4.74; N, 12.92; found C, 68.69; H, 4.92; N, 12.54.

EXAMPLE 23

4-{(9aS)-2-(2,4-difluorobenzyl)-5-oxo-3-[(trifluoroacetyl)amino]-7,8,9,9a-tetrahydro-5H-pyrido[2,3-α]pyrrolizin-4-yl}-N-[(1R)-2,3-dihydro-1H-inden-1-yl] benzamide A. 1-(2,4-difluorophenyl)-3-nitroacetone To 120 ml of dichloromethane solution of (2,4-difluorophenyl)acetic acid (10 g, 58.1 mmol) at 0° C., 1,1'-carbonyldiimidazole (9.4 g, 58.1 mmol) was added slowly. The mixture was then stirred for 2.5 hours at room temperature. The solvent was removed. Then the solid residue was triturated with diethyl ether and dried. The white fluffy solid 1-[(2,4-difluorophenyl)acetyl]-1H-imidazole was used for the next step without further purification. In a separate flask, to the 100 ml of dimethyl sulfoxide solution of potassium tert-butoxide (7.2 g, 63.9 mmol) at 0° C., nitromethane (4.6 g, 75.5 mmol) was added. After stirring for 5 minutes, the 1-[(2,4-difluorophenyl)acetyl]-1H-imidazole made previously was added slowly. The mixture was left stirring overnight while the temperature was gradually warmed up to room temperature. The reaction mixture was poured into 250 ml water and then acidified with 2N HCl to pH=4. The aqueous was extracted with ethyl acetate. After washing with brine and drying with sodium sulfate, removal of the solvent afforded 9.4 g yellowish solid. $^1$H-NMR (400 MHz, CD$_3$OD) δ 7.18 (m, 1H), 6.82 (m, 2H), 5.30 (s, 2H), 3.82 (s, 2H) ppm. ESI-MS m/z 214 (M–H)$^-$.

B. (Z)-1-(2,4-difluorobenzyl)-2-nitroethenylamine

The mixture of 1-(2,4-difluorophenyl)-3-nitroacetone (9.4 g, 43.7 mmol) and ammonium acetate (16.8 g, 219 mmol) in 250 ml benzene was refluxed with Dean-Stark setup for 5 hours. The reaction mixture was then partitioned between ether and water. The organic portion was washed with brine and dried over sodium sulfate. Removing the solvent afforded 8.5 g light brown solid. $^1$H-NMR (400 MHz, CD$_3$OD) δ 7.20 (m, 1H), 6.84 (m, 3H), 3.65 (s, 2H) ppm. ESI-MS m/z 215 (M+H)$^+$.

C. 4-[2-[(2S)-1-(tert-butoxycarbonyl)-2-pyrrolidinyl]-6-(2,4-difluorobenzyl)-3-(ethoxycarbonyl)-5-nitro-1,4-dihydro-4-pyridinyl]benzoic acid The solvent of the benzene solution of (Z)-1-(2,4-difluorobenzyl-2-nitroethenylamine (7.78 g, 36.3 mmol) and t-butyl (2S)-2-[3-ethoxycarbonyl)-3-phenyl-2-propenoyl]-1pyrrolidinecarboxylate (15.2 g, 36.3 mmol) was evaporated and the resulting residue was heated to 120° C. in the oven for 3 hours. The resulting brown glass (22.2 g) was carried to the next step without further purification. ESI-MS m/z 636 (M+Na)$^+$, 612 (M–H)$^-$.

D. 4-[2-[(2S)-1-(tert-butoxycarbonyl)-2-pyrrolidinyl]-6-(2,4-difluorobenzyl)-3-(ethoxycarbonyl)-5-nitro-4-pyridinyl]benzoic acid To a 280 ml acetonitrile solution of the dihydropyridine (C, 4-[2-[(2S)-1-(tert-butoxycarbonyl)-2-pyrrolidinyl]-6-(2, 4-difluorobenzyl)-3-(ethoxycarbonyl)-5-nitro-1,4-dihydro-4-pyridinyl]benzoic acid, crude, 22.2 g, about 36.3 mmol), was added dropwise of aqueous solution of ammonium cerium nitrate (39.8 g, 72.6 mmol in 20 ml water). Stirred for 5 minutes. Diluted with ethyl acetate and washed with water, brine subsequently. Upon drying, the solvent was removed. The resulting 22 g foamy solid was carried to the next step without further purification. ESI-MS m/z 634 (M+Na)$^+$, 610 (M–H)$^-$.

E. 4-[(9aS)-2-(2,4-difluorobenzyl)-3-nitro-5-oxo-7,8,9,9a-tetrahydro-5H-pyrido[2,3-a]pyrrolizin-4-yl] benzoic acid To the flask containing crude 4-[2-[(2S)-1-(tert-butoxycarbonyl)-2-pyrrolidinyl]-6-(2,4-difluorobenzyl)-3-(ethoxycarbonyl)-5-nitro-4-pyridinyl]benzoic acid (D, 22.2 g, 36.3 mmol), 200 ml premixed trifloroacetic acid and dichloromethane (10 ml/4.2 ml ratio) was added. The resulting mixture was stirred at room temperature for 20 minutes. The solvents were removed in vacuo. The resulting residue was dissolved in 150 ml mixture of triethyl amine and dichloromethane (10 ml/20 ml) and was stirred at room temperature for 2 hours.

The reaction mixture was diluted with ethyl acetate and washed with water, brine subsequently. After removing the solvent, 9.0 g foamy solid was obtained. ESI-MS m/z 466 (M+H)$^+$, 464 (M–H)$^-$.

F. 4-[(9aS)-3-amino-2-(2,4-difluorobenzyl)-5-oxo-7,8,9,9a-tetrahydro-5H-pyrido[2,3-α]pyrrolizin-4-yl] benzoic acid To the methanol solution of the crude nitro compound (E, 4-[(9aS)-2-2,4-difluorobenzyl)-3-nitro-5-oxo-7,8,9,9a-tetrahydro-5H-pyrido[2,3-a]pyrrolizin-4-yl]benzoic acid), (9.0 g) was added catalytic amount of 10% Pd/C. After degassing under nitrogen, the mixture was stirred overnight under 1 atm hydrogen gas. Filtered through celite. Removing the solvent from filtrate afforded 8.1 g brown foam. ESI-MS m/z 436 (M+H)$^+$.

G. 4-{(9aS)-2-(2,4-difluorobenzyl)-5-oxo-3-[(trifluoroacetyl)amino]-7,8,9,9a-tetrahydro-5H-pyrido[2,3-a]pyrrolizin-4-yl}benzoic acid To the 100 ml of dichloromethane solution of the aniline (F, 4-[(9aS)-3-amino-2-(2,4-difluorobenzyl)-5-oxo-7,8,9,9a-tetrahydro-5H-pyrido[2,3-a]pyrrolizin-4-yl]benzoic acid, 8 g, 18.4 mmol), 4.8 ml diisopropylethylamine (27.6 mmol) and 3.4 ml trifluoroacetic acid (24.0 mmol) were added. The resulting mixture was stirred for 3 hours. Diluted with dichloromethane. Washed with potassium hydrogenphthalate and brine. Removing the solvent afforded 7.9 g foamy solid. The crude product was carried to the next step without further purification. ESI-MS m/z 532 (M+H)$^+$, 530 (M–H)$^-$.

H. To the 2.0 ml dichloromethane solution containing the acid (G, 4-{(9aS)-2-(2,4-difluorobenzyl)-5-oxo-3-[(trifluoroacetyl)amino]-7,8,9,9a-tetrahydro-5H-pyrido[2,3-a]pyrrolizin-4-yl}benzoic acid, 956 mg, 1.8 mmol), 1-(3-Dimethylaminopropyl)-3-ethylcarbodiimide hydrochloride (691 mg, 3.6 mmol) and 1-hydroxybenzotriazole hydrate, 480 mg (R)-(–)-1-aminoindan (3.6 mmol) was added. The resulting mixture was stirred at room temperature for 3 hours. Diluted with dichloromethane. Washed with water and brine subsequently. Dried with sodium sulfate. Upon the removal of the solvent, the residue was purified with flash chromatography. 320 mg of the title compound as a light yellowish solid was obtained. NMR (400 MHz, CDCl$_3$) δ 7.95 (m, 2H), 7.32 (m, 5H), 6.95 (m, 4 m), 5.62 (m, 1H), 4.59 (m, 1H), 4.15 (m, 1H), 3.55 (s, 2H), 3.15 (m, 1H), 3.06 (m, 1H), 2.90 (m, 1H), 2.58 (m, 1H), 2.32 (m, 2H), 2.02 (m, 1H), 1.25 (m, 1H) ppm. ESI-MS m/z 647 (M+H)$^+$, 645 (M−H)$^−$.

EXAMPLE 24

4-((9aS)-3-[(Cyclopentylcarbonyl)amino]-5-oxo-2-{2-[4-(trifluoromethyl)phenyl]ethyl}-7,8,9,9a-tetrahydro-5H-pyrido[2,3-a]pyrrolizin-4-yl)-N-(2-furylmethyl)benzamide

A. 1-Nitro-4-[4-(trifluoromethyl)phenyl]-2-butanone

To a solution of 3-[4-(trifluoromethyl)phenyl]propanoic acid (4.36 g, 20.0 mmol) in THF (100 ml) was added carbonyldiimidazole (3.89 g, 24.0 mmol) and the mixture was refluxed for 1 h. Into a separate flask was placed nitromethane (4.5 ml, 80.0 mmol), THF (40 ml) and sodium hydride (0.96 g, 24.0 mmol) and the mixture was stirred for 10 min. To this was added slowly the imidazolide from the first reaction and the mixture was refluxed for 16 h. To the reaction mixture was added water (100 ml) and the pH was adjusted to 3 with HCl. The THF was removed by rotary evaporation. The product was extracted with ethyl acetate. The product was purified by silica gel column chromatography (silica gel/30% ethyl acetate in petroleum ether) giving A as an oil (3.70 g, 71%). $^1$H NMR (300 MHz, CDCl$_3$) δ 7.53 (dd, 2H), 7.28 (dd, 2H), 5.20 (s, 2H), 3.03 (m, 2H), 2.87 (m, 2H).

B. (1Z)-1-Nitro-4-[4-(trifluoromethyl)phenyl]-1-buten-2-amine

To a solution of A (3.74 g, 14.33 mmol) in benzene was added ammonium acetate (5.5 g) and the mixture was refluxed under a Dean-Stark trap for 90 min. The benzene was removed by rotary evaporation and the residue was dissolved in diethylether and washed with water and brine. The organic solution was dried (Na$_2$SO$_4$) and concentrated to give an B as an oil (3.34 g, 12.85 mmol, 90%). $^1$H NMR (300 MHz, CDCl$_3$) δ 7.51 (dd, 2H), 7.24 (dd, 2H), 6.45 (s, 1H), 2.91 (t, 2H), 2.47 (t, 2H).

C. 4-[(1Z)-3-[(2S)-1-(tert-Butoxycarbonyl)pyrrolidinyl]-2-(ethoxycarbonyl)-3-oxo-1-propenyl]benzoic acid To a solution of tert-butyl (2S)-2-(3-ethoxy-3-oxopropanoyl)-1-pyrrolidinecarboxylate (5.0 g, 17.5 mmol) in benzene (50 ml) and piperidine (0.3 ml, 3 mmol) was added 4-carboxybenzaldehyde (2.63 g, 17.5 mmol), and the mixture was refluxed for 3 h. The cooled solution was washed with 0.1 N HCl twice. The aqueous layer was extracted three times with ether. The combined organic phases were dried (Na$_2$SO$_4$) and concentrated to give C as a tan solid (5.54 g, 76% yield). LCMS m/z 416 (M−H), 833 (2M−H).

D. 4-(2-[1-(tert-Butoxycarbonyl)-2-pyrrolidinyl]-3-(ethoxycarbonyl)-5-nitro-6-{2-[4-(trifluoromethyl)phenyl]ethyl}-4-pyridinyl)benzoic acid Knoevenagel adduct C (2.96 g, 7.10 mmol) and B (1.85 g, 7.10 mmol) were added to a flask and placed neat in an oven at 120° C. for 1.25 h. The reaction mixture was allowed to cool and then was dissolved in acetonitrile (40 ml) and water (2 ml). To this solution was added cerium ammonium nitrate (7.7 g, 14.2 mmol) and the mixture was stirred at RT for 1 h. To this was added water (50 ml) and the product was extracted with ethyl acetate. The organic layer was washed with brine. The solution was dried and concentrated. The product was purified by silica gel column chromatography (silica gel/40% ethyl acetate and 1% acetic acid in petroleum ether) giving D as white solid (1.60 g, 2.44 mmol, 34%). LCMS m/z 656 (M−H), 680 (M+Na)$^+$.

E. 4-((9aS)-3-Nitro-5-oxo-2-{2-[4-(trifluoromethyl)phenyl]ethyl}-7,8,9,9a-tetrahydro-5H-pyrido[2,3-a]pyrrolizin-4-yl)benzoic acid To D (1.60 g, 2.44 mmol) was added a 40 ml solution of 70% trifluoroacetic acid in dichloromethane (DCM). The mixture was stirred for 45 min and then the solvents were removed by rotary evaporation. The residue was dissolved in DCM (30 ml) and triethylamine (15 ml) was added. The solution was stirred at RT overnight. The solvents were removed by rotary evaporation. The residue was partitioned between water and ethyl acetate. The organic layer was washed 3× with buffer (pH=5) and the aqueous washes were back extracted with ethyl acetate 2×. The organic layer was dried over Na2So4 and concentrated by rotary evaporation to yield E as a colorless foam with 85% purity (1.30 g). LCMS m/z 512 (MH+), 510 (M−H). $^1$H NMR (300 MHz, CDCl$_3$) 8.08 (dd, 2H), 7.49 (dd, 2H), 7.40 (dd, 2H), 7.28 (dd, 2H), 4.71 (m, 1H), 3.71 (m, 1H), 3.37 (m, 1H), 3.14 (m, 3H), 2.42 (m 1H), 2.36 (m, 2H), 1.38 (m, 1H) ppm.

F. 4-((9aS)-3-Amino-5-oxo-2-{2-[4-(trifluoromethyl)phenyl]ethyl}-7,8,9,9a-tetrahydro-5H-pyrido[2,3-α]pyrrolizin-4-yl)benzoic acid To a solution of E (0.38 g) in methanol (7 ml) was added 10% palladium on carbon dust (0.1 g) and the mixture was subjected to stirring under 1 atm of hydrogen. After the reaction was complete as evidenced by HPLC, the hydrogen was pumped away and the solids were removed by filtration. The clear solution was evaporated to dryness leaving F as a white solid (0.345 g, 97%). LCMS m/z 482 (MH+).

G. 4-((9aS)-3-amino-5-oxo-2-{2-[4-(trifluoromethyl)phenyl]ethyl}-7,8,9,9a-tetrahydro-5H-pyrido[2,3-α]pyrrolizin-4-yl)-N-(2-furylmethyl)benzamide To a solution of F (0.345 g, 0.72 mmol) in DCM (10 ml) was added furfurylamine (0.14 g, 1.44 mmol), hydroxybenzotriazole (0.194 g, 1.44 mmol), and EDC (0.276 g, 1.44 mmol), and the mixture was stirred at RT overnight. The solution was washed with ammonium acetate buffer (pH=4) and the organic layer was dried and concentrated. The product was purified by silica gel column chromatography (silica gel/100% ethyl acetate) giving G as tan solid (0.153 g, 38%). LCMS m/z 562 (MH)$^+$. $^1$H NMR (300 MHz, CDCl$_3$) δ 7.80 (dd, 2H), 7.47 (dd, 2H), 7.30 (m, 5H), 6.56 (m, 1H), 6.23 (d, 2H), 4.57 (m, 2H), 3.571 (m, 2H), 3.26–3.13 (m, 4H), 2.21 (m, 2H), 2.00 (m 1H), 1.20 (m, 1H) ppm. Calcd for C$_{31}$H$_{28}$N$_4$O$_3$F$_3$ X 1.0 H$_2$O: C, 64.35; H, 5.05; N, 9.68. Found: C, 64.67; H, 5.04; N, 9.51.

H. To a solution of G (25 mg, 0.045 mmol) in DCM (0.9 ml) was added cyclopentylcarbonyl chloride (13 mg, 2.2 eq), Hunig's base (13 mg, 2.2 eq) and DMAP (2 mg). The mixture was stirred at RT for one hour and then washed with ammonium acetate buffer (pH=4). The organic layer was dried and concentrated to yield the title compound as a foam (18 mg, 62%). LCMS m/z 657 (MH+), 655 (M−H).

EXAMPLE 25

4-((9aS)-3-[(Ethylcarbonyl)amino]-5-oxo-2-{2-[4-(trifluoromethyl)phenyl]ethyl}-7,8,9,9a-tetrahydro-5H-pyrido[2,3-α]pyrrolizin-4-yl)-N-(2-furylmethyl)benzamide Using the procedure for the previous example, Example 24, and the appropriate acid chloride, the title compound was isolated as a yellow foam (22 mg, 73%). LCMS showed good purity m/z 615 (M–H).

EXAMPLE 26

4-((9aS)-3-[(Cyclopropylcarbonyl)amino]-5-oxo-2-{2-[4-(trifluoromethyl)phenyl]ethyl}-7,8,9,9a-tetrahydro-5H-pyrido[2,3-α]pyrrolizin-4-yl)-N-(2-furylmethyl)benzamide Using the procedure for Example 24 and the appropriate acid chloride, the title compound was isolated as a colorless foam (34 mg, 79%). LCMS showed good purity m/z 629 (MH+).

EXAMPLE 27

4-((9aS)-3-[(Trifluoromethylcarbonyl)amino]-5-oxo-2-{2-[4-(trifluoromethyl)phenyl]ethyl}-7,8,9,9a-tetrahydro-5H-pyrido[2,3-α]pyrrolizin-4-yl)-N-(2-furylmethyl)benzamide Starting with trifluoroacetic anhydride and intermediate Example 24, G, and following the procedure previously described the title compound was isolated as a colorless foam (32 mg, 94%). LCMS showed good purity m/z 655 (M–H).

EXAMPLE 28

4-((9aS)-3-Cyano-5-oxo-2-{2-[4-(trifluoromethyl)phenyl]ethyl}-7,8,9,9a-tetrahydro-5H-pyrido[2,3-α]pyrrolizin-4-yl)-N-(2-furylmethyl)benzamide A. 3-oxo-5-[4-(Trifluoromethyl)phenyl]pentanenitrile To a suspension of sodium hydride (40 mmol) in THF (50 ml) was added acetonitrile (5.2 ml, 100 mmol) dropwise. The the resulting anion was added a solution of ethyl 3-[4-(trifluoromethyl)phenyl]propanoate (34.4 mmol) in THF (10 ml). The reaction mixture was refluxed for 3 h and then allowed to cool. To the resulting slurry was added water (50 ml) and the solution was acidified to pH 2 with 6 N HCl. The aqueous solution was extracted three times with diethyl ether. The organic layer was dried ($Na_2SO_4$) and concentrated. The product was purified by silica gel column chromatography (silica gel/25% ethyl acetate in petroleum ether) giving A as an oil (4.36 g, 53% yield). $^1$H NMR (300 MHz, $CDCl_3$) δ 7.47 (m, 2H), 7.31 (m, 2H), 3.44 (s, 2H), 2.99 (s, 4H).

B. (2Z)-3-Amino-5-[4-(trifluoromethyl)phenyl]-2-pentenenitrile

To a solution of A (4.36 g, 18.1 mmol) in benzene (125 ml) was added ammonium acetate (7.0 g, 90 mmol) and the mixture was refluxed for 4 h and then allowed to cool. The solvent was removed by rotary evaporation leaving B as a yellow solid (3.63 g, 84% yield). $^1$H NMR (300 MHz, $CDCl_3$) δ 7.50 (m, 2H), 7.21 (m, 2H), 7.31 (m, 2H), 4.56 (br s, 2H), 3.76 (s, 1H), 2.84 (t, 2H), 2.39 (t, 2H).

C. Enamine B (0.24 g, 1 mmol) and Knoevenagel adduct 24 C (0.42 g, 1 mmol) were combined neat in a flask and heated to 120° C. for 30 min. The reaction mixture was allowed to cool and the resulting glass was taken up in acetonitrile (6 ml) and water (0.3 ml). To this solution was added cerium ammonium nitrate (1.1 g, 2 mmol). The solution was stirred at RT for 1 h. Water (15 ml) was added and the suspension was extracted 3 times with ethyl acetate. The organic layer was washed with brine, dried and concentrated. To the resulting oil was added 70% TFA in DCM (20 ml) and the mixture was stirred at RT for 1 h. The solvents were removed by rotary evaporation. To the resulting gum was added DCM (20 ml) and triethylamine (10 ml) and the reaction was stirred overnight at RT. The solvents were removed by rotary evaporation. The residue was partitioned between ethyl acetate and phosphate buffer (pH=4). The organic layer was dried and concentrated. The resulting solid was dissolved in DCM (10 ml) and methanol (2 ml). To this solution was added. EDC (276 mg) and hydroxybenzotriazole (194 mg) and furfurylamine (0.14 g). The reaction mixture was stirred at RT 4 h. The reaction mixture was transferred to a separatory funnel with DCM and then washed with ammonium acetate buffer (pH=5) and brine. The organic layer was dried and concentrated. The product was purified by silica gel column chromatography (silica gel/40% ethyl acetate in petroleum ether) giving the title compound as an off-white solid (0.15 g, 26% yield). LCMS m/z 569 (M–H), 571(MH)$^+$, 593 (M+Na)$^+$, 1141 (2MH)$^+$. $^1$H NMR (300 MHz, $CDCl_3$) δ 7.89 (d, 2H, J=8.3 Hz), 7.54 (m, 4H), 7.36 (m, 3H), 6.45 (m, 1H), 6.33 (dd, 2H), 4.73 (m, 1H), 4.64 (m, 2H), 3.69 (m, 1H), 3.48 (m, 2H), 3.38 (m, 1H), 3.23 (m, 2H), 2.48 (m, 1H), 2.36 (m, 2H), 1.62 (m, 2H) ppm. HRMS Calcd for $C_{32}H_{25}N_4O_3F_3$: MH$^+$=571.1957. Found: MH$^+$=571.1951.

EXAMPLES 29 AND 30

4-{(9aS)-3-acetyl-2-[2-(4-fluorophenyl)ethyl]-5-oxo-7,8,9,9a-tetrahydro-5H-pyrido[2,3-α]pyrrolizin-4-yl}-N-(2-furylmethyl)benzamide and 4-{(9aS)-3-[3-(4-fluorophenyl)propanoyl]-2-methyl-5-oxo-7,8,9,9a-tetrahydro-5H-pyrido[2,3-α]pyrrolizin-4-yl}-N-(2-furylmethyl)benzamide A. 1-[3-(4-Fluorophenyl)propanoyl]-1H-imidazole To a 200 ml THF solution of 4-fluorophenyl propionic acid (33.6 g, 0.2 mol) was added 1,1-carbonyldiimidazole (32.4 g, 0.2 mol) and the mixture was warmed to reflux 1 h. The reaction mixture was partially concentrated, diluted with ethyl acetate, extracted with brine three times, dried ($Na_2SO_4$), filtered and concentrated to afford compound 1 as a white solid (41.3 g, 0.19 mol, 95%). $^1$H NMR (300 MHz, $CDCl_3$) δ 8.17 (d, 1H), 7.48 (d, 1H), 7.23 (m, 2H), 7.11 (s, 1H), 7.02 (m, 1H), 3.16 (m, 4H) ppm.

B and B'. 4-{3-acetyl-6-[(2S)-1-(tert-Butoxycarbonyl)pyrrolidinyl]-5-(ethoxycarbonyl)-2-[2-(4-fluorophenyl)ethyl]pyridinyl}benzoic acid B and 4-{2-[(2S)-1-(tert-butoxycarbonyl)pyrrolidinyl]-3-(ethoxycarbonyl)-5-[3-(4-fluorophenyl)propanoyl]-6-methyl-4-pyridinyl}benzoic acid B'

To a stirring mixture of 95% sodium hydride (2.4 g, 0.10 mol) and A (10.9 g, 0.05 mol) in 250 ml THF at –10° C. under nitrogen was added 2-butanone (7.2 g, 0.10 mol). The mixture was stirred overnight at RT, warmed to reflux 4 h and after 24 h diluted with ethyl ether and aqueous ammonium chloride solution, extracted once with 1N HCl and three times with water, dried (Na$_2$SO$_4$), filtered and concentrated to a yellow oil. Ammonium acetate (15 g, 0.19 mol) was added and the reaction was warmed 10 minutes to 100° C., diluted with ethyl acetate, filtered, then concentrated to a colorless oil (6.7 g). A portion of this material (2.0 g, 9 mmol) was mixed with 4-[(1Z)-3-[1-(tert-butoxycarbonyl)-2-pyrrolidinyl]-2-(ethoxy-carbonyl)-3-oxo-1-propenyl]benzoic acid (3.14 g, 9 mmol) and heated to 120° C. with mixing for 90 minutes, mixed for 30 minutes at RT as a 25 ml solution in dimethylacetamide with cerric ammonium nitrate (5.0 g, 0.09 mol). The reaction was diluted with ethyl acetate/water, extracted three times with brine, dried (Na$_2$SO$_4$), filtered and concentrated to give a mixture of B and B' as a golden brown viscous oil (21 g, 87%). LCMS m/z 619 (MH+).

C and C'. 4-{(9aS)-3-acetyl-2-[2-(4-fluorophenyl) ethyl]-5-oxo-7,8,9,9a-tetrahydro-5H-pyrido[2,3-α] pyrrolizin-4-yl}benzoic acid C and 4-{(9aS)-3-[3-(4-fluorophenyl)propanoyl]-2-methyl-5-oxo-7,8,9,9a-tetrahydro-5H-pyrido[2,3-α]pyrrolizin-4-yl}benzoic acid C'

A 100 ml solution of B and B' in 70% TFA/DCM was left at RT for ten minutes, concentrated, dissolved in 30% triethylamine/DCM (300 ml), left at RT overnight, then concentrated to give a mixture of C and C' as an amber oil (13 g, 80%): LCMS m/z 473 (MH+).

D and D'. To a mixture of C and C' (4.0 g, 7 mmol) was added DMF (25 ml), 1-(3-(dimethylamino)propyl)-3-ethylcarbodiimide hydrochloride (3.82 g 20 mmol), hydroxybenzotriazole (2.7 g, 19 mmol) and furfurylamine (2.0 g, 19 mmol). After 24 h the reaction was diluted with ethyl acetate, extracted with water (2×), 1N NaOH (1×), dried (Na$_2$SO$_4$), filtered, concentrated and chromatographed (silica gel/ethyl acetate) on silica gel column to give compound 29 as a reddish-brown gum (0.11 g, 2%). LCMS m/z 550 (M–H); $^1$H NMR (300 MHz, DMSO-d6) δ 9.10 (m, 1H), 7.91 (m, 3H), 7.58 (d, 2H), 7.37 (m, 3H), 7.21 (d, 2H), 7.09 (dd, 2H), 6.60 (d, 1H), 6.40 (m, 1H), 4.76 (m, 1H); 4.49 (m, 4H), 4.02 (m, 1H), 2.98 (m, 2H), 2.30 (m, 1H), 2.25 (m, 2H), 1.33 (m, 1H), 0.65 (t, 3H) ppm.

Also isolated by column chromatography was the isomer 30 as a tan powder (3.12 g, 5%). LCMS m/z 550 (M–H). $^1$H NMR (300 MHz, DMSO-d6) δ 9.11 (m, 1H), 7.90 (m, 3H), 7.58 (d, 2H), 7.37 (m, 4H), 6.92 (d, 2H), 6.41 (m, 1H), 6.31 (d, 1H), 4.75 (m, 1H) 4.52 (m, 1H), 4.02 (m, 1H); 3.50 (m, 1H) 3.32 (m, 4H), 3.25 (m, 1H) 2.62 (m, 1H), 2.24 (m, 2H), 1.99 (m, 1H), 1.21 (m, 2H), 1.17 (m, 1H) ppm.

EXAMPLE 31

4-[(9aS)-2-[2-(4-fluorophenyl)ethyl]-3-(2-furoyl)-5-oxo-7,8,9,9a-tetrahydro-5H-pyrido[2,3-α]pyrrolizin-4-yl]-N-(2-furylmethyl)benzamide The title compound was prepared from 4-[2-[2-(4-Fluorophenyl)ethyl]-3-(2-furoyl)-5-oxo-7,8,9,9a-tetrahydro-5H-pyrido[2,3-α]pyrrolizin-4-yl]benzoic acid according to the method previously described for 4-{(9aS)-3-acetyl-2-[2-(4-fluorophenyl)ethyl]-5-oxo-7,8,9,9a-tetrahydro-5H-pyrido [2,3-α]pyrrolizin-4-yl}-N-(2-furylmethyl)benzamide (Example 29). After chromatography (silica gel/ethyl acetate) the title compound was obtained as a light brown powder (0.175 g, 1%). LCMS m/z 590 (MH+) $^1$H NMR (300 MHz, DMSO-d6) δ 8.96 (dd, 1H), 7.95 (m, 1H), 7.87 (dd, 1H), 7.74 (m, 2H), 7.56 (dd, 1H), 7.27 (m, 2H), 7.09 (m, 2H), 7.05 (m, 2H), 6.52 (dd, 1H); 6.38 (dd, 1H) 6.27 (dd, 1H), 4.82 (m, 1H), 4.44 (t, 2H) 3.53 (m, 1H), 3.30 (m, 2H), 3.00 (m, 1H), 2.95 (m, 2H), 2.37 (m, 2H), 2.30 (m, 2H) ppm.

EXAMPLE 32

4-[(3aS)-6-(4-Fluorophenyl)-8,10-dioxo-2,3,3a,5,6, 7,8,10-octahydro-1H-pyrrolizino[1,2-b]quinolin-9-yl]-N-[(1R)-2,3-dihydro-1H-inden-1-yl]benzamide Using the synthetic method described earlier in the synthesis of 4-{(9aS)-3-acetyl-2-[2-(4-fluorophenyl)ethyl]-5-oxo-7,8,9,9a-tetrahydro-5H-pyrido[2,3-α]pyrrolizin-4-yl}-N-(2-furylmethyl)benzamide (Example 29), the title compound was prepared from 4-[(3aS)-6-(4-fluorophenyl)-8,10-dioxo-2,3,3a,5,6,7,8,10-octahydro-1H-pyrrolizino[1,2-b]quinolin-9-yl]benzoic acid (prepared using the enamine of 5-(4-fluorophenyl)-1,3-cyclohexanedione and Knoevenagel product 4-[(1Z)-3-[1-(tert-butoxycarbonyl)-2-pyrrolidinyl]-2-(ethoxy-carbonyl)-3-oxo-1-propenyl]benzoic acid). A portion of the crude material (100 mg) was chromatographed (silica gel/ethyl acetate) to give the title compound as a tan powder (52 mg, 52%). LCMS m/z 572 (MH+) $^1$H NMR (300 MHz, DMSO-d6) δ 7.90 (d, 2H), 7.40 (m, 2H), 7.10–7.35 (m, 6H), 7.10 (dd, 2H), 6.40 (d, 1H), 5.75 (m, 2H), 4.75 (d, 1H), 3.30–3.75 (m, 2H), 2.80–3.10 (m, 2H), 2.70 (m, 1H), 2.55 (m, 1H), 2.35 (m, 1H), 1.95 (m, 1H), 1.75 (m, 4H), 1.50 (m, 2H) ppm.

EXAMPLE 33

Ethyl (9aS)-4-(4-{[(2-furylmethyl)amino] carbonyl}phenyl)-5-oxo-2-[2-(3-pyridinyl)ethyl]-7, 8,9,9a-tetrahydro-5H-pyrido[2,3-α]pyrrolizine-3-carboxylate A. Ethyl 3-oxo-5-(3-pyridinyl)pentanoate To a mixture of 3-(3-pyridyl)propionic acid (13.6 g, 0.09 mol), Meldrum's acid (13.0 g, 0.09 mol) and dimethylaminopyridine (11 g, 0.09 mol) was added 1,3-dicyclohexylcarbodiimide (18.54 g, 0.09 mol) and DCM (140 ml). The reaction was stirred for 4 h, filtered, concentrated, diluted with 200 ml ethanol and 25 ml 4M HCl/dioxane. The mixture was warmed to reflux 2 h, concentrated, combined with excess sodium carbonate, followed by 50% sodium hydroxide, then triturated with ethyl acetate, filtered, dried (Na$_2$SO$_4$), filtered, then concentrated to give A as an amber oil (19.8 g, 100%). LCMS m/z 222 (MH+)

B. Ethyl (2Z)-3-amino-5-(3-pyridinyl)-2-pentenoate

To a 200 ml benzene solution of A (19.8 g) was added ammonium acetate (50 g) and acetic acid (1 ml). The mixture was refluxed using a Dean Stark trap for 6 h. Potassium carbonate (100 g.) was added, the mixture was concentrated, triturated with ethyl acetate, filtered and concentrated to give B as a viscous amber oil (19.8 g, 90%). LCMS m/z 221 (MH+)

C. 4-{2-[(2S)-1-(tert-butoxycarbonyl)-2-pyrrolidinyl]-3,5-bis(ethoxycarbonyl)-6-[2-(3-pyridinyl)ethyl]-4-pyridinyl)benzoic acid A mixture of B (2.2 g, 0.01 mol) and 4-[(1Z)-3-ethoxy-3-oxo-2-(2-pyrrolidinylcarbonyl)-1-propenyl]benzoic acid (3.47 g, 0.01 mol) was heated to 120° C. for 90 minutes. The reaction was dissolved with dimethylacetamide (20 ml) and agitated with cerric ammonium nitrate (5.5 g) for 30 minutes, diluted with ethyl acetate, extracted with brine three times, dried ($Na_2SO_4$), filtered and concentrated to give C as an amber gum (6.0 g, 97%). LCMS m/z 618 (MH+).

D. 4-{(9aS)-3-(ethoxycarbonyl)-5-oxo-2-[2-(3-pyridinyl)ethyl]-7,8,9,9a-tetrahydro-5H-pyrido[2,3-α]pyrrolizin-4-yl}benzoic acid To C (6.0 g) was added 100 ml 70% TFA/DCM and after ten minutes the reaction was concentrated, dissolved into triethylamine/DCM (200 ml, 30%). The solution was left standing at RT overnight, then concentrated to give D as a viscous amber oil (4.5 g, 95%). LCMS m/z 472 (MH+).

E. To D (1.1 g) was added 20 ml DMF, 1-[3-dimethylamino)propyl]-3-ethylcarbodiimide hydrochloride (1.0 g, 5 mmol), hydroxybenzotriazole (0.70 g, 5 mmol) and furfurylamine (0.48 g, 5 mmol). The reaction was agitated overnight, diluted with ethyl acetate, extracted with water three times, dried ($Na_2SO_4$), filtered and concentrated to 1.50 g. Submitted (100 mg) for chromatographic separation (acetonitrile:water/3:7) to give the title as a yellow viscous oil (8.6 mg, 9%). LCMS m/z 527 (MH+).

EXAMPLE 34

Ethyl (9aR)-4-(4-{[(2-furylmethyl)amino]carbonyl}phenyl)-5-oxo-2-{2-[4-(trifluoromethyl)phenyl]ethyl}-9,9a-dihydro-5H-[1,3]thiazolo[3',4':1,2]pyrrolo[3,4-b]pyridine-3-carboxylate A. tert-Butyl (4R)-4-[(2,2-dimethyl-4,6-dioxo-1,3-dioxan-5-yl)carbonyl]-1,3-thiazolidine-3-carboxylate A was prepared from (4R)-3-(tert-butoxycarbonyl)-1,3-thiazolidine-4-carboxylic acid (5.30 g, 22.7 mmol) and Meldrum's acid according to the previously described procedure used for Example 1C, giving the title compound as yellow solid (7.31 g, 89%). LCMS m/z 358 (M−H). $^1$H NMR (300 MHz, CDCl$_3$, mixture of rotamers) δ 5.88 (m, 1H), 4.80–4.51 (m, 3H), 369 (m, 1H), 3.05 (m, 1H), 2.0–1.8 (m, 3H), 1.8–1.7 (m, 6H), 1.44 (s, 5H), 1.38 (s, 4H) ppm.

B. ArgoGel-OH (1.0 g, 0.44 mmol), A, 4-formyl benzoic acid, and ethyl (2Z)-3-amino-5-[4-(trifluoromethyl)phenyl]-2-pentenoate were combined according to the previously described procedure for Example 1, giving the title compound as a white solid (32 mg, 0.050 mmol, 11%). LCMS m/z 634 (M−H). $^1$H NMR (400 MHz, CDCl$_3$) δ 7.82 (d, J=8.2 Hz, 2H), 7.55 (d, J=8.2 Hz, 2H), 7.40–7.32 (m, 4H), 6.36 (m, 1H), 6.33 (d, J=8.3 Hz, 2H), 5.05 (t, 1H), 4.94 (d, J=8.1 Hz, 1H), 4.65 (d, J=6.2 Hz, 1H), 4.34 (d, J=8.3, 1H), 4.02 (q, 2H), 3.44 (m, 1H), 3.20 (m, 4H), 2.68 (t, 1H), 0.94 (t, 3H) ppm. Calcd for $C_{33}H_{28}N_3O_5S_1F_3 \times 1.0\ H_2O$: C, 60.64; H, 4.63; N, 6.43. Found: C, 60.62; H, 4.59; N, 6.48.

EXAMPLE 35

Ethyl (9aR)-4-(4-{[(2-furylmethyl)amino]carbonyl}phenyl)-5-oxo-2-{2-[4-(trifluoromethyl)phenyl]ethyl}-9,9a-dihydro-5H-[1,3]thiazolo[3',4':1,2]pyrrolo[3,4-b]pyridine-3-carboxylate 8,8-dioxide A. To a solution of Example 34 (16 mg, 0.025 mmol) in THF (1 ml) and t-butanol (0.25 ml) was added N-methylmorpholine N-oxide (9 mg) and 2.5% osmium tetroxide in t-butanol (1 drop). The reaction mixture was stirred overnight and the product was purified on a silica gel column eluting the product with 60% ethyl acetate/petroleum ether giving the product as a white solid (10 mg, 0.015 mmol, 60%). LCMS m/z 666 (M−H). $^1$H NMR (300 MHz, CDCl$_3$) δ 7.88 (d, J=8.2 Hz, 2H), 7.55 (d, J=8.2 Hz, 2H), 7.46–7.32 (m, 5H), 6.48 (m, 1H), 6.33 (d, J=8.4 Hz, 2H), 5.24 (t, 1H), 5.15 (d, J=8.4 Hz, 1H), 4.66 (d, J=6.2 Hz, 2H), 4.24 (d, J=8.4, 1H), 4.02 (q, 2H), 3.85 (dd, 1H), 3.24 (m, 4H), 3.03 (dd, 1H), 0.98 (t, 3H) ppm.

EXAMPLE 36

Ethyl (9αS)-4-{4-[(benzylamino)carbonyl]phenyl}-5-oxo-2-{2-[4-(trifluoro-methyl)phenyl]ethyl}-9,9a-dihydro-5H-[1,3]oxazolo[3',4':1,2]pyrrolo[3,4-b]pyridine-3-carboxylate A. 4-[(1Z)-3-[(4S)-3-(tert-butoxycarbonyl)-1,3-oxazolidin-4-yl]-2-(ethoxycarbonyl)-3-oxo-1-propenyl]benzoic acid To (4S)-3-(tert-butoxycarbonyl)-1,3-oxazolidine-4-carboxylic acid (11.15 g, 0.051 mol), Meldrum's acid (7.33 g, 0.051 mol), dimethylaminopyridine (12.44 g, 0.102 mol) and DCM (200 ml) was added 1,3-dicyclohexylcarbodiimide (10.52 g, 0.051 mol). After 24 h the reaction was filtered, extracted twice with 1N HCl (200 ml) once with water, dried ($Na_2SO_4$), filtered, concentrated, then warmed to reflux in 100% ethanol for 2 h. The reaction was concentrated to a pale yellow oil (14.3 g). A portion of this material (5.88 g, 0.02 mol) was refluxed 2 h using Dean Stark trap with 4-carboxybenzaldehyde (3.0 g, 0.02 mol), piperidine (110 mg, 0.0012 mol) and toluene (100 ml). The reaction was filtered, concentrated to give A as a yellow gum (7.1 g, 85%). LCMS m/z 420 (MH+).

B. To A (8.2 g, 0.02 mol), in dimethylacetamide (20 ml) was added ethyl (2Z)-3-amino-5-[4-(trifluoromethyl)phenyl]-2-pentenoate (5.7 g, 0.02 mol). The reaction was warmed to 120° C. for 2 h, shaken at RT 20 minutes with cerric ammonium nitrate (11 g, 0.02 mol), diluted with ethyl acetate, extracted three times with water, dried ($Na_2SO_4$), filtered, concentrated, dissolved in TFA/DCM (100 ml, 70%). The reaction was concentrated, diluted with triethylamine/DCM (200 ml, 30%) and after 24 h at RT, concentrated and dissolved as a DMF (0.05M) solution of 4-(3-(ethoxycarbonyl)-5-oxo-2-{2-[4-(trifluoromethyl)phenyl]ethyl}-9,9a-dihydro-5H-[1,3]oxazolo[3',4':1,2]pyrrolo[3,4-b]pyridin-4-yl)benzoic acid. Added as an amber DMF solution (20 ml, 2 mmol) to 1-(3-(dimethylamino)propyl)-3-ethylcarbodiimide hydrochloride (0.77 g, 4 mmol), hydroxybenzotriazole (0.54 g, 4 mmol) and benzylamine (0.43 g, 4 mmol). After mixing overnight at RT the reaction was diluted with ethyl acetate, extracted three times with water, dried ($Na_2SO_4$), filtered, and concentrated to a reddish brown gum. Chromatographed (C18/acetonitrile:water/

3:7) 100 mg of this gum to give the title compound as a golden gum (11.1 mg, 11%). LCMS m/z 631(M–H).

EXAMPLE 37

Ethyl (9aS)-4-(4-{2-[(2-furylmethyl)amino]-2-oxoethyl}phenyl)-5-oxo-2-{2-[4-(trifluoromethyl)phenyl]ethyl}-7,8,9,9a-tetrahydro-5H-pyrido[2,3-α]pyrrolizine-3-carboxylate A. {4-[(1Z)-3-[(2S)-1-(tert-Butoxycarbonyl)pyrrolidinyl]-2-(ethoxycarbonyl)-3-oxo-1-propenyl]phenyl}acetic acid To a solution of 4-formylphenylacetic acid (4.31 g, 26.3 mmol) in benzene (75 ml) and piperidine (0.95 ml, 9.5 mmol) was added tert-butyl (2S)-2-(3-ethoxy-3-oxopropanoyl)-1-pyrrolidinecarboxylate (8.1 g, 28.4 mmol). The solution was refluxed under a Dean-Stark trap for 8 h. The solvent was removed by rotary evaporation. The product was purified by silica gel column chromatography (silica gel/75% ethyl acetate in petroleum ether) giving A as an off-white solid (3.81 g, 34% yield). LCMS m/z 432 (MH)+.

B. [4-(2-[(2S)-1-(tert-Butoxycarbonyl)pyrrolidinyl]-3,5-bis(ethoxycarbonyl)-6-{2-[4-(trifluoromethyl)phenyl]ethyl}-4-pyridinyl)phenyl]acetic acid Ethyl (2Z)-3-amino-5-[4-(trifluoromethyl)phenyl]-2-pentenoate (0.57 g, 2.0 mmol) and A (0.86 g, 2.0 mmol) were combined and heated to 120° C. for 30 min and then allowed to cool to an amber glass. The glass was dissolved in acetonitrile (12 ml) and water (0.6 ml). To this solution was added cerium ammonium nitrate (2.2 g, 4.0 mmol) and the solution was stirred at RT for 1 h. Water (15 ml) was added and the suspension was extracted 3 times with ethyl acetate. The organic layer was washed with brine, dried and concentrated. The product was purified by silica gel column chromatography (silica gel/40% ethyl acetate in petroleum ether) giving B as an tan solid (0.40 g, 29% yield). LCMS m/z 699 (MH)+.

C. [4-((9aS)-3-(Ethoxycarbonyl)-5-oxo-2-{2-[4-(trifluoromethyl)phenyl]ethyl}-7,8,9,9a-tetrahydro-5H-pyrido[2,3-α]pyrrolizin-4-yl)phenyl]acetic acid A solution of B (0.40 g, 0.57 mmol) in 70% TFA/DCM (10 ml) was stirred for 40 min at RT. The solvents were removed and the residue was taken up in DCM (10 ml) and TEA (5 ml). The reaction mixture was stirred overnight at RT. The solvents were removed by rotary evaporation and the residue was partitioned between ethyl acetate and phosphate buffer (pH=4). The organic layer was washed twice with buffer and the aqueous layers were back extracted with ethyl acetate. The product was purified by silica gel column chromatography (silica gel/40% ethyl acetate, 1% acetic acid in petroleum ether) giving C as an off-white solid (0.14 g, 44% yield). LCMS m/z 553 (MH)+ and 575 (M+Na+).

D. To a solution of C (0.070 g, 0.127 mmol) in DCM (2 ml) was added furfurylamine (0.025 g, 0.25 mmol), hydroxy benzotriazole (34 mg, 0.25 mmol) and EDC (49 mg, 0.25 mmol). The solution was stirred overnight at RT. The reaction mixture was transferred to a separatory funnel with DCM, and the organic layer was washed twice with phosphate buffer (pH=4). The organic layer was dried ($Na_2SO_4$) and concentrated giving the title compound as a colorless foam (80 mg, 99% yield). LCMS m/z 632 (MH+). $^1$H NMR (300 MHz, $CDCl_3$) δ 7.46 (d, 2H, J=8.0 Hz), 7.27 (m, 7H), 6.25 (m, 1H), 6.10 (d, 2H), 4.64 (m, 1H), 4.33 (m, 2H), 3.93 (q, 2H), 3.64 (m, 1H), 3.54 (s, 2H), 3.30 (m, 1H), 3.10 (m, 4H), 2.40–2.25 (2H), 1.26 (m, 1H), 0.78 (t, 3H) ppm. HRMS Calcd for $C_{35}H_{32}N_3O_5F_3$: $MH^+$=632.2372. Found: $MH^+$=632.2401.

EXAMPLE 38

Ethyl (9aS)-4-(4-{[(2-furylmethyl)amino]carbonyl}phenyl)-5-oxo-2-{2-[4-(trifluoromethyl)phenyl]ethyl}-7,8,9,9a-tetrahydro-5H-pyrido[2,3-α]pyrrolizine-3-carboxylate-N-oxide A. 4-((9aS)-3-(ethoxycarbonyl)-5-oxo-2-{2-[4-(trifluoromethyl)phenyl]ethyl}-7,8,9,9a-tetrahydro-5H-pyrido[2,3-α]pyrrolizin-4-yl)benzoic acid-N-oxide To a solution of 4-((9aS)-3-(ethoxycarbonyl)-5-oxo-2-{2-[4-(trifluoromethyl)phenyl]ethyl}-7,8,9,9a-tetrahydro-5H-pyrido[2,3-α]pyrrolizin-4-yl)benzoic acid Example 4C (50 mg, 0.1 mmol) in DCM (3 ml) was added m-chloroperbenzoic acid (65 mg, 0.3 mmol). The reaction mixture was stirred at RT for 72 h. The reaction mixture was loaded onto a silica gel column and the product was eluted with 75% ethyl acetate 1% acetic acid in petroleum ether giving A as a white solid (27.3 mg, 50% yield). LCMS m/z 555 (MH+).

To a solution of A (0.070 g, 0.127 mmol) in DCM (2 ml) was added furfurylamine (0.025 g, 0.25 mmol), hydroxy benzotriazole (34 mg, 0.25 mmol) and EDC (49 mg, 0.25 mmol). The solution was stirred overnight at RT. The reaction mixture was transferred to a separatory funnel with DCM, and the organic layer was washed twice with phosphate buffer (pH=4). The organic layer was dried ($Na_2SO4$) and concentrated giving the title compound as a colorless foam (80 mg, 99% yield).
LCMS m/z 632 (MH+). $^1$H NMR (300 MHz, $CDCl_3$) δ 7.46 (d, 2H, J=8.0 Hz), 7.27 (m, 7H), 6.25 (m, 1H), 6.10 (d, 2H), 4.64 (m, 1H), 4.33 (m, 2H), 3.93 (q, 2H), 3.64 (m, 1H), 3.54 (s, 2H), 3.30 (m, 1H), 3.10 (m, 4H), 2.40–2.25 (2H), 1.26 (m, 1H), 0.78 (t, 3H) ppm. HRMS Calcd for $C_{35}H_{32}N_3O_5F_3$: $MH^+$=632.2372. Found: $MH^+$=632.2401.

EXAMPLE 39

Ethyl 2-(4-fluorobenzyl)-4-(6-{[(2-furylmethyl)amino]carbonyl}-3-pyridazinyl)-5-oxo-7,8,9,9a-tetrahydro-5H-pyrido[2,3-α]pyrrolizine-3-carboxylate A. 6-(ethoxycarbonyl)-3-pyridazinecarboxylic acid To the diethyl 3,6-pyridazinedicarboxylate (5.0 g, 22.3 mmol) in 150 ml ethyl alcohol, 24.5 ml 1N NaOH was added. The mixture was stirred for 2 hours. The resulting salt was collected by filtration then was dissolved in minimum amount of water. The aqueous solution obtained was then acidified with 2N HCl in ether until the PH=2 and extracted with ethyl acetate. The combined extracts were washed with brine and dried over sodium sulfate. Removal of the solvent afforded 4.1 g of light yellowish oil. $^1$HNMR (400 MHz, $CD_3OD$) δ 8.42 (s, 2H), 4.52 (q, 2H), 1.42 (t, 3H) ppm.

B. Ethyl 6-(hydroxymethyl)-3-pyridazinecarboxylate

The acid (A, 4.1 g, 20.9 mmol) was dissolved in 100 ml DME and cooled to 0° C. Four (4) ml of N-methyl morpholine was added followed by isobutyl chloroformate (5.0 ml, 38 mmol). After stirring at this temperature for 2 hours, 25 ml aqueous solution of sodium borohydride (2.67 g, 70 mmol) was added and the stirring continued for 20 minutes. The reaction mixture was extracted with ethyl acetate and the combined organic layers were washed with brine and dried. The residue after the removal of the solvent was purified with flash chromatography. 1.95 g alcohol was obtained in the form of yellow solid. $^1$H NMR (400 MHz, CD$_3$OD) δ 8.19 (d, 1H), 7.65 (d, 1H), 4.50 (q, 2H), 1.42 (t, 3H) ppm.

C. Ethyl 6-formyl-3-pyridazinecarboxylate

To the flask containing the alcohol (B, ethyl 6-(hydroxymethyl)-3-pyridazinecarboxylate 2.15 g, 11.7 mmol), triethyl amine (1.9 g, 14.0 mmol) in 24 ml DMSO and 48 ml chloroform at 0° C., sulfur trioxide pyridine complex (2.23 g, 14.0 mmol) was added and then stirred for 2 hours. Diluted with dichlomethane and washed with water. After removal of the solvent in vacuo, flash chromatography of the residue afforded 2.1 g aldehyde in white solid. $^1$H NMR (400 MHz, CDCl$_3$) δ 10.42 (s, 1H), 8.28 (d, 1H), 8.18 (d, 1H), 4.57 (q, 2H), 1.43 (t, 3H) ppm.

D. Diethyl 2-[(2S)-1-(tert-butoxycarbonyl)pyrrolidinyl]-4-[6-(ethoxycarbonyl)-3-pyridazinyl]-6-(4-fluorobenzyl)-1,4-dihydro-3,5-pyridinedicarboxylate The mixture of pyridazine aldehyde (C, ethyl 6-formyl-3-pyridazinecarboxylate, 145 mg, 0.81 mmol), enamine (ethyl-3-amino-4-(4-fluorophenyl)-2-butenoate, 180 mg, 0.81 mmol), β-ketoester (tert-butyl (2S)-2-(3-ethoxy-3-oxopropanoyl)-1-pyrrolidinecarboxylate, 231 mg, 0.81 mmol), piperidine (13.8 mg, 0.162 mmol) and acetic acid (9.6 mg, 0.16 mmol) in 4 ml toluene was heated to 100° C. for 2 hours. Removed the solvent and the residue was partitioned between ethyl acetate and water. 265 g crude product was collected from organic solvent upon drying and removal of the solvent and carried to the next step without further purification. ESI-MS m/z 653 (M+H)$^+$.

E. Diethyl 2-[(2S)-1-(tert-butoxycarbonyl)pyrrolidinyl]-4-[6-(ethoxycarbonyl)-3-pyridazinyl]-6-(4-fluorobenzyl)-3,5-pyridinedicarboxylate To the dihydropyridine (D, diethyl 2-[(2S)-1-(tert-butoxycarbonyl)pyrrolidinyl]-4-[6-(ethoxycarbonyl)-3-pyridazinyl]-6-(4-fluorobenzyl)-1,4-dihydro-3,5-pyridinedicarboxylate, 265 mg, 0.41 mmol} in 9 ml acetonitrile, ammonium cerium nitrate (445 mg, 0.82 mmol) in 1.8 ml water was added. The reaction mixture was stirred for 5 minutes. Ten (10) ml water was added and then extracted with ethyl acetate. The combined organic layers were washed with brine and dried over sodium sulfate. Removal of the solvent provided 260 mg orange foam which was carried to the next step without further purification. ESI-MS m/z 651 (M+H)$^+$.

F. Ethyl 4-[6-(ethoxycarbonyl)-3-pyridazinyl]-2-(4-fluorobenzyl)-5-oxo-7,8,9,9a-tetrahydro-5H-pyrido[2,3-α]pyrrolizine-3-carboxylate Diethyl 2-[(2S)-1-(tert-butoxycarbonyl)pyrrolidinyl]-4-[6-(ethoxycarbonyl)-3-pyridazinyl]-6-(4-fluorobenzyl)-3,5-pyridinedicarboxylate (E, 260 mg crude) was first dissolved in 15 ml mixture of trifluoroacetic acid and dichloromethane (2 to 1 ratio) and stirred for 1 hour followed by the removal of the solvent. To this residue, 15 ml of mixture of triethylamine and dichloromethane (1 to 2 ratio) was added and the mixture was stirred for 2 hours. Upon removal of the solvent, the residue was purified by flash chromatography. 145 mg solid was obtained. $^1$H NMR (400 MHz, CDCl$_3$) δ 8.21 (d, 1H), 8.03 (d, 1H), 7.18 (t, 2H), 6.90 (t, 2H), 4.75 (m, 1H), 4.54 (q, 2H), 4.42 (m, 2H), 3.96 (q, 2H), 3.65 (m, 1H), 3.38 (m, 1H), 2.45 (m, 1H), 2.32 (m, 2H), 1.45 (t, 3H), 1.40 (m, 1H), 0.92 (t, 3H) ppm. ESI-MS m/z 505 (M+H)$^+$.

G. 6-[3-(ethoxycarbonyl)-2-(4-fluorobenzyl)-5oxo-7,8,9,9a-tetrahydro-5H-pyrido[2,3-α]pyrrolizin-4-yl]-3-pyridazinecarboxylic acid To the ethyl 4-[6-(ethoxycarbonyl)-3-pyridazinyl]-2-(4-fluorobenzyl)-5-oxo-7,8,9,9a-tetrahydro-5H-pyrido[2,3-a]pyrrolizine-3-carboxylate (F, 145 mg, 0.29 mmol) in 2.5 ml dioxane, 1.2 ml 1N NaOH was added and the resulting mixture was stirred overnight. Acidified with 2N HCl and extracted with ethyl acetate. The combined organic layers were washed with brine and dried over sodium sulfate. Removal of the solvent and purification of the resulting residue with flash chromatography afforded 125 mg off-white solid. $^1$H NMR (400 MHz, CDCl$_3$) δ 8.38 (d, 1H), 8.17 (d, 1H), 7.20 (t, 2H), 6.95 (t, 2H), 4.79 (m, 1H), 4.42 (m, 2H), 3.98 (q, 2H), 3.62 (m, 1H), 3.39 (m, 1H), 2.45 (m, 1H), 2.32 (m, 2H), 1.41 (m, 1H), 0.92 (t, 3H) ppm. ESI-MS m/z 475 (M−H)$^-$.

H. The mixture of 6-[3-(ethoxycarbonyl)-2-(4-fluorobenzyl)-5-oxo-7,8,9,9a-tetrahydro-5H-pyrido[2,3-α]pyrrolizin-4-yl]-3-pyridazinecarboxylic acid (G, 33 mg, 0.07 mmol), furfurylamine (19.3 mmol, 0.14 mmol), 1-(3-Dimethylaminopropyl)-3-ethylcarbodiimide hydrochloride (26.7 mg, 0.14 mmol) and 1-hydroxybenzotriazole hydrate (18.8 mg, 0.14 mmol) in 2 ml dichloromethane was stirred for 2 hours. The mixture was then partitioned between water and ethyl acetate. The organic was washed with brine and dried over sodium sulfate. The residue upon the removal of the solvent was purified with flash chromatography. Twelve (12) mg white solid was obtained. NMR (400 MHz, CDCl$_3$) δ 8.38 (d, 1H), 8.08 (d, 1H), 7.20 (t, 2H), 6.92 (t, 2H), 4.78 (m, 1H), 4.67 (d, 2H), 4.40 (dd, 2H), 3.90 (q, 2H), 3.64 (m, 1H), 3.39 (m, 1H), 2.48 (m, 1H), 2.35 (m, 2H), 1.40 (m, 1H), 0.90 (t, 3H) ppm. ESI-MS m/z 556 (M+H)$^+$.

EXAMPLE 40

Ethyl (9aS)-2-[2-(4-fluorophenyl)ethyl]-4-(4-methylphenyl)-5-oxo-7,8,9,9a-tetrahydro-5H-pyrido[2,3-α]pyrrolizine-3-carboxylate A. Diethyl 2-[(2S)-1-(tert-butoxycarbonyl)pyrrolidinyl]-6-[2-(4-fluorophenyl)ethyl]-4-(4-methylphenyl)-1,4-dihydro-3,5-pyridinedicarboxylate To the toluene solution of 4-methylbenzaldehyde (120 mg, 1.0 mmol), β-ketoester (tert-butyl (2S)-2-(3-ethoxy-3-oxopropanoyl)-1-pyrrolidinecarboxylate, 285 mg, 1.0 mmol) and enamine (ethyl-3-amino-5-(4-fluorophenyl)-2-pentenoate 237 mg, 1.0 mmol), were added piperidine (17 mg, 0.2 mmol) and acetic acid (12 mg, 0.2 mmol). The resulting mixture was heated to reflux for 3 hours. Diluted with ethyl acetate and washed with water and brine subsequently. Removed the solvent and the light brownish solid was carried to the next step without further purification. ESI-MS m/z 607 (M+H)$^+$, 605 (M−H)$^-$.

B. Diethyl 2-[(2S)-1-(tert-butoxycarbonyl)pyrrolidinyl]-6-[2-(4-fluorophenyl)ethyl]-4-(4-methylphenyl)-1,4-dihydro-3,5-pyridinedicarboxylate To the 6 ml acetonitrile solution of the dihydropyridine (A, crude product, about 1 mmol) diethyl 2-[(2S)-1-(tert-butoxycarbonyl)pyrrolidinyl]-6-[2-(4-fluorophenyl)ethyl]-4-(4-methylphenyl)-1,4-dihydro-3,5-pyridinedicarboxylate crude product, 1 mmol)), was added dropwise of aqueous solution of ammonium cerium nitrate 1.1 g, 2 mmol in 3 ml water and 3 ml of acetonitrile). Stirred for 5 minutes. Diluted with ethyl acetate and washed with water, brine subsequently. Upon drying, the solvent was removed. The resulting foamy solid was carried to the next step without further purification. ESI-MS m/z 605 (M+H)$^+$.

C. Ethyl (9aS)-2[2-(4-fluorophenyl)ethyl]-4-(4-methylphenyl)-5-oxo-7,8,9,9a-tetrahydro-5H-pyrido[2,3-a]pyrrolizine-3-carboxylate To the flask containing crude diethyl 2-[(2S)-1-(tert-butoxycarbonyl)pyrrolidinyl]-6-[2-(4-fluorophenyl)ethyl]-4-(4-methylphenyl)-1,4-dihydro-3,5-pyridinedicarboxylate (B, 1.0 mmol), 14.2 ml premixed trifluoroacetic acid and dichloromethane (10 ml/4.2 ml) were added. The resulting mixture was stirred at room temperature for 20 minutes. The solvents were removed in vacuo. The resulting residue was dissolved in a 30 ml mixture of triethylamine and dichloromethane (10 ml/20 ml) and was stirred at room temperature for 2 hours. The reaction mixture was diluted with ethyl acetate and washed with water, brine subsequently. After removing the solvent, the residue was purified with flash chromatography. 125 mg of solid was obtained. $^1$H NMR (400 MHz, CDCl$_3$) δ 7.22 (m, 4H), 7.18 (t, 2H), 6.95 (t, 2m), 4.64 (m, 1H), 4.02 (q, 2H), 3.70 (m, 1H) 3.35 (m, 1H), 3.15 (m, 2H), 3.05 (m, 2H), 2.42 (m, 1H), 2.35 (s, 3H), 2.30 (m, 2H), 1.38 (m, 1H) ppm. ESI-MS m/z 459 (M+H)$^+$, 917 (2M+1)$^+$.

EXAMPLE 41

Ethyl (9aS)-4-[4-({[3-(1H-imidazol-1-yl)propyl]amino}carbonyl)phenyl]-5-oxo-2-{2-[4-(trifluoromethyl)phenyl]ethyl}-7,8,9,9a-tetrahydro-5H-pyrido[2,3-α]pyrrolizine-3-carboxylate A. To a stirred solution of 4-((9aS)-3-(ethoxycarbonyl)-5-oxo-2-{2-[4 (trifluoromethyl)phenyl]ethyl}-7,8,9,9a-tetrahydro-5H-pyrido[2,3-α]pyrrolizin-4-yl)benzoic acid) Example 4C (0.050 g, 0.102 mmol) in 1 mL of dichloromethane, EDCI (0.023 g, 0.123 mmol) and 1-(3-aminopropyl)imidazole (0.026, 0.205 mmol) were added. The reaction mixture was allowed to stir for ~3 h. The reaction mixture was concentrated and redissolved in 10 mL ethyl acetate. The organics were then washed with saturated aqueous NaHCO$_3$ (2×) and brine. Filtration and concentration provided a brown oil which was purified by radial chromatography (dichloromethane/methanol (10:1)) to yield 0.013 g (20%) of the desired product as a tan solid: $^1$H NMR (CDCl$_3$, 400 MHz) δ 7.89 (s, 2H), 7.52–7.50 (d, 2H, J=8.1), 7.39–7.37 (d, 2H, J=7.9), 7.32–7.29 (d, 2H, J=8.1), 7.89–6.89 (m, 2H), 4.73–4.70 (dd, 1H, J=6.4, J=10.3), 4.25 (bs, 2H), 4.04–3.92 (m, 2H), 3.72–3.60 (m, 1H), 3.52 (bs, 2H), 3.40–3.31 (m, 2H), 3.27–3.18(m, 4H), 2.51–2.41(m, 1H), 2.40–2.28 (m, 2H), 2.25–2.11 (m, 2H), 1.43–1.29 (m, 1H), 1.22 (s, 1H), 0.889–0.853 (t, 2H, J=7.2); low resolution MS (ES$^+$) m/e 646 (MH$^+$); TLC (CH$_2$Cl$_2$/MeOH (9:1)): R$_f$=0.24; RP-HPLC (BDS Hypersil C-18 25 cm×4.6 mm; 10–100% CH$_3$CN in H$_2$O with 0.1% TFA buffer; 30 minutes; 1 mL/min) t$_r$=8.12 min, 96.6% purity.

EXAMPLE 42

Ethyl (9aS)-4-[4-({[2-(1H-imidazol-5-yl)ethyl]amino}carbonyl)phenyl]-5-oxo-2-{2-[4-(trifluoromethyl)phenyl]ethyl}-7,8,9,9a-tetrahydro-5H-pyrido[2,3-α]pyrrolizine-3-carboxylate A. To a stirred solution of 4-((9aS)-3-(ethoxycarbonyl)-5-oxo-2-{2-[4-(trifluoromethyl)phenyl]ethyl}-7,8,9,9a-tetrahydro-5H-pyrido[2,3-α]pyrrolizin-4-yl)benzoic acid Example 4C (0.050 g, 0.102 mmol) in 1 mL of dichloromethane, PyBoP (0.059 g, 0.113 mmol), diisopropyl ethyl amine (0.040 g, 0.102 mmol) and 1-(3-aminoethyl)imidazole (0.012 g, 0.113 mmol) were added. The reaction mixture was allowed to stir for ~3 h. The reaction mixture was concentrated and redissolved in 1 mL of ethyl acetate. The organics were then washed 1 M HCl solution, saturated NaHCO$_3$ and brine. Filtration and concentration provided a brown oil which was purified by radial chromatography (dichloromethane/methanol (10:1)) to yield 0.033 g (51%) of the desired product as a tan solid: $^1$H NMR (CDCl$_3$, 400 MHz) δ 8.04 (s, 1H), 7.89–7.87 (d, 2H, J=8.1), 7.70 (s, 1H), 7.51–7.49 (d, 2H, J=8.1), 7.37–7.35 (d, 2H, J=8.1), 7.30–7.28 (d, 2H, J=8.1), 4.71 (dd, 1H, J=10.4, J=6.2), 4.05–3.87 (m, 2H), 3.72–3.55 (m, 3H), 3.45–3.25 (m, 1H), 3.24–3.05 (m, 3H), 2.91 (bs, 1H), 2.50–2.38 (m, 1H), 2.38–2.22 (m, 2H), 1.54–1.47 (t, 1H, J=7.4), 1.47–1.41 (d, 2H, J=6.7), 0.92–0.76 (t, 3H, J=7.3);TLC (EtOAc/hexanes (1:1)): R$_f$=0.25; RP-HPLC (BDS Hypersil C-18 25 cm×4.6 mm; 10–100% CH$_3$CN in H$_2$O with 0.1% TFA buffer; 30 minutes; 1 mL/min) t$_r$=7.49 min, 98.5% purity.

EXAMPLE 43

Ethyl (9aS)-4-(4-{[(1R)-2,3-dihydro-1H-inden-1-ylamino]carbonyl}phenyl)-2-(4-methylpentyl)-5-oxo-7,8,9,9a-tetrahydro-5H-pyrido[2,3-α]pyrrolizine-3-carboxylate A. Ethyl 7-methyl-3-oxooctanoate To a stirred solution of Meldrum's Acid (2.0 g, 13.9 mmol) in 100 mL of CH$_2$Cl$_2$, hexanoic acid (1.61 g, 13.9 mmol) was added followed by DMAP (3.39 g, 27.8 mmol) and finally DCC (2.86 g, 13.9 mmol). The reaction stirred overnight at room temperature. The mixture was then filtered and the filtrate washed with 1M HCl, H$_2$O and Brine. The organics were then dried over sodium sulfate, filtered and concentrated to a yellow oil. The material was then dissolved in 100 mL of EtOH and refluxed overnight. The reaction mixture was concentrated to yield 2.58 g (99%) of a clear oil. No purification performed: $^1$H NMR (CDCl$_3$, 400 MHz) δ 4.22–4.12 (q, 2H, J=7.07), 3.40 (s, 2H), 2.56–2.44 (t, 2H, J=7.42), 1.69–1.43 (m, 3H), 1.30–1.21 (t, 3H, J=7.07), 1.19–1.09 (m, 2H), 0.89–0.81 (d, 6H, J=6.55).

B. Ethyl (2Z)-3-amino-7-methyl-2-octenoate

To a mixture of β-ketoester (ethyl 7-methyl-3-oxooctanoate) in 100 mL of toluene ammonium acetate (5.34 g, 69.3 mmol) was added. The mixture was allowed to stir overnight at reflux. The reaction mixture was dissolved in ethyl acetate and the organics washed with H$_2$O (3×) and brine. The organics were then dried over sodium sulfate, filtered and concentrated to yield a yellow oil: TLC (EtOAc/hexanes (1:4)): R$_f$=0.39

C. 4-[2-[(2S)-1-(tert-butoxycarbonyl)pyrrolidinyl]-3,5-bis(ethoxycarbonyl)-6-(4-methylpentyl)-1,4-dihydro-4-pyridinyl]benzoic acid To a stirred solution of tert-Butyl (2S)-2-(3-ethoxy-3-oxopropanoyl)-1-pyrrolidinecarboxylate (1.43 g, 5.02 mmol) in 30 mL of toluene, ethyl (2Z)-3-amino-7-methyl-2-octenoate (1.0 g, 5.02 mmol) was added followed by 4-formylbenzoic acid (0.904 g, 6.01 mmol) and piperidine (0.214 g, 2.51 mmol). The reaction was allowed to reflux for 3 h. The crude mixture was concentrated and carried on without purification.

D. 4-[2-[(2S)-1-(tert-butoxycarbonyl)pyrrolidinyl]-3,5-bis(ethoxycarbonyl)-6-(4-methylpentyl)-4-pyridinyl]benzoic acid 4-[2-[(2S)-1-(tert-butoxycarbonyl)pyrrolidinyl]-3,5-bis(ethoxycarbonyl)-6-(4-methylpentyl)-1,4-dihydro-4-pyridinyl]benzoic acid was dissolved in a 50:50 mixture of acetonitrile:$H_2O$. To the mixture cerium ammonium nitrate was added (6.65 g, 10.3 mmol) and allowed to stir for 45 minutes. The reaction mixture was dissolved in 100 mL of ethyl acetate and washed with $H_2O$ (2×50 mL) and brine. The organics were then dried over sodium sulfate, filtered and concentrated to yield a orange/red oil which was purified by column chromatography (ethyl acetate/hexanes (4:1)) to give 2.0 g of a solid.

E. 4-[(9aS)-3-9ethoxycarbonyl)-2-(4-methylpentyl)-5-oxo-7,8,9,9a-tetrahydro-5H-pyrido-[2,3-a]pyrrolizin-4-yl]benzoic acid To a stirred solution of 4-[2-[(2S)-1-(tert-butoxycarbonyl)pyrrolidinyl]-3,5-bis(ethoxycarbonyl)-6-(4-methylpentyl)-4-pyridinyl]benzoic acid (D) (2.0 g, 3.52 mmol) dissolved in 30 mL of dichloromethane TFA (6 mL) was added. The reaction stirred for 1 h. and was then concentrated to yield a reddish brown oil. The crude mixture was dissolved in 35 mL of dichloromethane and triethylamine (9 mL) was added slowly. The reaction was allowed to stir overnight. The mixture was then concentrated and redissolved in 50 mL of ethyl acetate. The organics were washed with 0.1 M HCl, $H_2O$ and Brine. The organics were then dried over sodium sulfate, filtered and concentrated. The concentrated material was purified via radial chromatography (dichloromethane/MeOH (20:1)) to yield 0.548 g (37%) of the desired product as a tan solid.

F. To a stirred solution of 4-[(9aS)-3-(ethoxycarbonyl)-2-(4-methylpentyl)-5-oxo-7,8,9,9a-tetrahydro-5H-pyrido[2,3-α]pyrrolizin-4-yl]benzoic acid (0.100 g, 0.222 mmol) in 1 mL of dichloromethane, EDCI (0.051 g, 0.266 mmol), HOBT (0.036 g, 0.266 mmol) and (R)-(−)-1-aminoindane (0.065 g, 0.444 mmol) were added. The reaction mixture was allowed to stir for ~3 h. The reaction mixture was concentrated and redissolved in 1 mL of ethyl acetate. The organics were then washed with saturated aqueous $NaHCO_3$ and brine. Filtration and concentration provided a brown oil which was purified by radial chromatography chromatography (ethyl acetate/hexanes (4:1)) to yield 0.013 g (20%) of the desired product as a tan solid: $^1H$ NMR (CDCl$_3$, 400 MHz) δ 7.83–7.76 (d, 2H, J=7.9), 7.44–7.38 (d, 2H, J=7.93), 7.35–7.29 (d, 1H, J=7.76), 7.27–7.17 (m, 3H), 6.52–6.44 (m, 1H), 5.71–5.63 (q, 1H, J=7.41), 4.70–4.63 (dd, 1H, J=10.3, J=6.38), 4.09–3.94 (m, 2H), 3.68–3.56 (m, 1H), 3.35–3.24 (m, 1H), 3.07–2.95 (m, 1H), 2.95–2.76 (m, 3H), 2.74–2.58 (m, 1H), 2.51–2.40 (m, 1H), 2.35–2.19(m, 2H), 1.97–1.84 (m, 1H), 1.83–1.64 (m, 2H), 1.61–1.48 (m, 1H), 1.43–1.31 (m, 1H), 1.30–1.20 (m, 2H), 1.01–0.93 (t, 3H, J=7.09), 0.89–0.81 (d, 6H, J=6.55); low resolution MS (ES$^+$) m/e 566 (MH); RP-HPLC (BDS Hypersil C-18 25 cm×4.6 mm; 10–100% $CH_3CN$ in $H_2O$ with 0.1% TFA buffer; 30 minutes; 1 mL/min) $t_r$=23.8 min, 99.9% purity.

EXAMPLE 44

Ethyl (9aS)-4-(4-{[(1R)-2,3-dihydro-1H-inden-1-ylamino]carbonyl}phenyl)-5-oxo-2-(3,3,3-trifluoropropyl)-7,8,9,9a-tetrahydro-5H-pyrido[2,3-α]pyrrolizine-3-carboxylate

A. Ethyl 6,6,6-trifluoro-3-oxohexanoate

To a stirred solution of Meldrum's Acid (3.0 g, 20.8 mmol) in 100 mL of $CH_2Cl_2$, 4-trifluoromethyl butyric acid (2.96 g, 20.8 mmol) was added followed by DMAP (5.08 g, 41.6 mmol) and finally DCC (4.30 g, 20.8 mmol). The reaction stirred overnight at room temperature. The mixture was then filtered and the filtrate washed with 1M HCl, $H_2O$ and Brine. The organics were then dried over sodium sulfate, filtered and concentrated to a yellow oil. The material was then dissolved in 100 mL of EtOH and refluxed overnight. The reaction mixture was concentrated and purified by column chromatography (ethyl acetate/hexanes (1:4)) to yield 1.88 g (43%) of a clear oil.: $^1H$ NMR (CDCl$_3$, 400 MHz) δ 4.24–4.10 (q, 2H, J=7.14), 3.45 (s, 2H), 2.93–2.73 (t, 2H, J=7.88), 2.52–2.28 (m, 2H), 1.31–1.20 (t, 3H, J=7.14)

B. Ethyl (2Z)-3-amino-6,6,6-trifluoro-2-hexenoate

To a mixture of β-ketoester (ethyl 6,6,6-trifluoro-3-oxohexanoate) in 100 mL of toluene ammonium acetate (3.41 g, 44.3 mmol) was added. The mixture was stirred overnight at reflux. The reaction mixture was dissolved in 40 mL of ethyl acetate and the organics washed with $H_2O$ (3×) and brine. The organics were then dried over sodium sulfate, filtered and concentrated to yield a yellow oil. Material used without further purification: $^1H$ NMR (CDCl$_3$, 400 MHz) δ 4.27–4.00 (m, 2H), 3.02–2.72 (m, 1H), 2.53–2.21 (m, 4H), 1.33–1.10 (t, 3H, J=7.07)

C. 4-[2-[(2S)-1-(tert-butoxycarbonyl)pyrrolidinyl]-3,5-bis(ethoxycarbonyl)-6-(3,3,3-trifluoropropyl)-1,4-dihydro-4-pyridinyl]benzoic acid To a stirred solution of tert-Butyl (2S)-2-(3-ethoxy-3-oxopropanoyl)-1-pyrrolidinecarboxylate (1.35 g, 4.74 mmol) in 30 mL of toluene, ethyl (2Z)-3-amino-6,6,6-trifluoro-2-hexenoate (1.0 g, 4.74 mmol) was added followed by 4-formylbenzoic acid (0.711 g, 4.74 mmol) and piperidine (0.202 g, 2.37 mmol). The reaction was allowed to reflux for 3 h. The crude mixture was concentrated and carried on without purification.

D. 4-[2-[(2S)-1-(tert-butoxycarbonyl)-2-pyrrolidinyl]-3,5-bis(ethoxycarbonyl)-6(3,3,3-trifluoropropyl)-4-pyridinyl]benzoic acid 4-[2-[(2S)-1-(tert-butoxycarbonyl)pyrrolidinyl]-3,5-bis(ethoxycarbonyl)-6-(3,3,3-trifluoropropyl)-1,4-dihydro-4-pyridinyl]benzoic acid (3.21 g, 6.91 mmol) was dissolved in a 50:50 mixture of acetonitrile:$H_2O$. To the mixture cerium ammonium nitrate was added (8.96 g, 13.8 mmol) and stirred for 45 minutes. The reaction mixture was dissolved in 100 mL of ethyl acetate and washed with H$_2$O (2×50 mL) and brine. The organics were then dried over sodium sulfate, filtered and concentrated to yield a orange/red oil that was purified by column chromatography (ethyl acetate/hexanes (4:1)). Mixture carried on without purification.

E. 4-[(9aS)-3-(ethoxycarbonyl)-5-oxo-2-(3,3,3-trifluoropropyl)-7,8,9,9a-tetrahydro-5H-pyrido[2,3-α]pyrrolizin-4-yl]benzoic acid To a stirred solution of 4-[2-[(2S)-1-(tert-butoxycarbonyl)-2-pyrrolidinyl]-3,5-bis(ethoxycarbonyl)-6-(3,3,3-trifluoropropyl)-4-pyridinyl]benzoic acid (3.0 g, 4.93 mmol) dissolved in 30 mL of dichloromethane TFA (7 mL) was added. The reaction stirred for 1.5 h. and was then concentrated to yield a reddish brown oil. The crude mixture was dissolved in 35 mL of dichloromethane and triethylamine (10 mL) was added slowly. The reaction was allowed to stir overnight. The mixture was then concentrated and redissolved in 50 mL of ethyl acetate. The organics were washed with 1 M HCl, H$_2$O and Brine. The organics were then dried over sodium sulfate, filtered and concentrated. The concentrated material was purified by column chromatography (dichloromethane/MeOH (20:1)) to yield 0.928 g (41%) of the desired product as an off white solid.

F. To a stirred solution of 4-[(9aS)-3-(ethoxycarbonyl)-5-oxo-2-(3,3,3-trifluoropropyl)-7,8,9,9a-tetrahydro-5H-pyrido[2,3-α]pyrrolizin-4-yl]benzoic acid (0.075 g, 0.162 mmol) in 1 mL of dichloromethane, EDCI (0.037 g, 0.194 mmol), HOBT (0.026 g, 0.194 mmol) and (R)-(–)-1-aminoindane (0.051 g, 0.324 mmol) were added. The reaction mixture was allowed to stir for ~3 h. The mixture was then concentrated and redissolved in 1 mL of ethyl acetate. The organics were then washed with saturated aqueous NaHCO$_3$ and brine. Filtration followed by concentration provided a brown oil which was purified by radial chromatography (ethyl acetate/hexanes (4:1)) to yield 0.046 g (49%) of the desired product as a white solid: $^1$H NMR (CDCl$_3$, 400 MHz) δ 7.86–7.77 (d, 2H, J=8.27), 7.45–7.37 (d, 2H, J=8.28), 7.36–7.29 (d, 1H, J=6.38), 7.28–7.16 (m, 3H), 6.48–6.37 (m, 1H), 5.72–5.64 (q, 1H, J=7.59), 4.71–4.63 (dd, 1H, J=10.34, J=6.21), 4.13–3.96 (m, 2H), 3.72–3.58 (m, 1H), 3.38–3.26 (m, 1H), 3.22–3.08 (m, 2H), 3.07–2.96 (m, 1H), 2.96–2.83 (m, 1H), 2.79–2.56 (m, 3H), 2.55–2.38 (m, 1H), 2.38–2.22 (m, 2H), 1.98–1.84 (m, 1H), 1.45–1.27 (m, 1H), 1.04–0.95 (t, 3H, J=7.07); TLC (EtOAc/Hex(4:1)): R$_f$=0.3; RP-HPLC (BDS Hypersil C-18 25 cm×4.6 mm; 10–100% CH$_3$CN in H$_2$O with 0.1% TFA buffer, 30 minutes; 1 mL/min) t$_r$=11.8 min, 94.1% purity.

EXAMPLE 45

Ethyl (9aS)-2-(2,4-difluorobenzyl)-4-{4-[(2,3-dihydro-1H-indol-1-ylamino)carbonyl]phenyl}-5-oxo-7,8,9,9a-tetrahydro-5H-pyrido[2,3-α]pyrrolizine-3-carboxylate A. To a stirred solution of 4-[(9aS)-2-(2,4-difluorobenzyl)-3-(ethoxycarbonyl)-5-oxo-7,8,9,9a-tetrahydro-5H-pyrido[2,3-α]pyrrolizin-4-yl]benzoic acid (0.150 g, 0.305 mmol) in 2 mL of dichloromethane, EDCI (0.070 g, 0.365 mmol), HOBT (0.049 g, 0.365 mmol) and 1-indolinamine (ref. Wijngaarden, I. et. al., *J Med Chem*, 1993, 36, 3693–99) (0.082 g, 0.609 mmol) were added. The reaction mixture was allowed to stir for ~3 h. The reaction mixture was concentrated and redissolved in 1 mL of ethyl acetate. The organics were then washed with saturated aqueous NaHCO$_3$ and brine. Filtration and concentration provided a brown oil which was purified by radial chromatography (dichloromethane/methanol (10:1)) to yield 0.071 g (38%) of the desired product as a tan solid: $^1$H NMR (CDCl$_3$, 400 MHz) δ 7.90–7.85 (d, 2H, J=8.27), 7.53–7.45 (m, 2H), 7.23–7.11 (m, 3H), 6.83–6.73 (m, 2H), 4.74–4.67 (dd, 1H, J=10.5, J=6.38), 4.42–4.23 (q, 2H, J=15.34), 3.99–3.90 (m, 2H), 3.74–3.65 (m, 3H), 3.40–3.32 (m, 1H), 3.14–3.06 (m, 2H), 2.50–2.42 (m, 1H ), 2.37–2.26 (m, 2H), 1.70–1.50 (m, 3H), 1.46–1.31 (m, 1H), 0.95–0.84 (t, 3H, J=7.24); low resolution MS (ES$^+$) m/e 609 (MH$^+$); RP-HPLC (BDS Hypersil C-18 25 cm×4.6 mm; 10–100% CH$_3$CN in H$_2$O with 0.1% TFA buffer; 30 minutes; 1 mL/min) t$_r$=8.12 min, 93.3% purity.

EXAMPLE 46

Ethyl (9aS)-4-{5-[(benzoylamino)methyl]-2-thienyl}-2-(4-fluorobenzyl)-5-oxo-7,8,9,9a-tetrahydro-5H-pyrido[2,3-α]pyrrolizine-3-carboxylate A benzene (5 mL) solution of 272 mg (1 mmol) 5-[(1,3-dioxo-1,3-dihydro-2H-isoindol-2-yl)methyl]-2-thiophenecarbaldehyde (Shearer, B. G. et. al, WO 95/00505) and 285 mg (1 mmol) of tert-Butyl (2S)-2-(3-ethoxy-3-oxopropanoyl)-1-pyrrolidinecarboxylate was refluxed for 1 hr in the presence of 50 µL (0.5 mmol) of piperidine. The reaction flask was fitted with a Dean-Stark trap, 224 mg (1 mmol) of ethyl (2Z)-3-amino-4-(4-fluorophenyl)-2-butenoate was added, and the solution was refluxed for 10 hr. The solution was cooled, concentrated, and the crude product was purified by silica gel chromatography (elution with 10% to 50% EtOAc in hexanes) to give 450 mg of the dihydropyridine intermediate as an off-white solid (foam) after drying under vacuum for several hrs. To a solution of 430 mg (0.58 mmol) of the above intermediate in 3 mL of CH$_3$CN and 3 mL of water was added 636 mg of CAN. After stirring at 22° C. for 2 hr, the mixture was diluted with Et$_2$O (30 mL) and washed with water (10 mL) and brine (10 mL). The organics were dried over MgSO$_4$, filtered, and concentrated. The crude product was taken into CH$_2$Cl$_2$ (5 mL), 3 mL of TFA was added, and the solution stirred for 2 hr at 22° C. The reaction was concentreated to dryness several times from CH$_2$Cl$_2$ and the crude product was taken into 3 mL of CH$_2$Cl$_2$ and 2 mL of Et$_3$N and stirred overnight. The reaction solution was diluted with 20 mL CH$_2$Cl$_2$ and washed with 0.1 N aqueous HCL solution (10 mL). The crude product was purified by silica gel chromatography (elution with 20% EtOAc/hexanes to 100% EtOAc) to give 245 mg (71% yield) of the pyrido-pyrollizine intermediate. A suspension of the above intermediate (230 mg, 0.38 mmol) in EtOH (5 mL) and hydrazine (1 mL) was warmed to effect dissolution and stirred for 14 hr at 22° C. The mixture was partially concentrated and filtered to remove the white solids. The filtrate was concentrated to yield 180 mg of intermediate amine as an oil (crude yield~100%). To a THF (2 mL) solution of 60 mg (0.13 mmol) of the above crude amine intermediate was added 45 µL of DIEA followed by 23 µL of benzoyl chloride and the resulting solution was stirred for 5 hr at 22° C. The reaction contents were poured into 10 mL of EtOAc and washed with 5 mL of 0.1 N HCl and 5 mL of brine before drying over Na$_2$SO$_4$. The filtered solution was concentrated and the crude product purified by silica gel chromatography (75% to 100% EtOAc in hexanes). The concentrated product fractions gave an oil that was taken into several drops of CH$_2$Cl$_2$ and stirred rapidly while adding several drops of Et$_2$O, then 2 mL of 50/50 EtOAc/hexanes. The resulting solids were isolated via filtration and dried under vacuum for 14 hr to provide 51 mg (70% yield for the acylation step) of pale yellow solid: $^1$H NMR (400 MHz, CDCl$_3$) δ 7.75 (d, 2H, J=7.2), 7.48 (t, 1H, J=18), 7.40 (t, 2H, J=19), 7.20 (dd, 2H, J=21, 14), 7.10 (d, 1H, J=9), 7.01 (d, 1H, J=9), 6.92 (t, 2H, J=21), 6.6 (m, 1H), 4.8 (d, 2H, J=14), 4.7 (dd, 1H, J=25, 15), 4.25 (dd, 2H, J=49, 36), 3.98 (m, 2H), 3.68 (m, 1H), 3.36 (m, 1H), 2.48 (m, 1H), 2.31 (m, 2H), 1.37 (t, 3H, J=18) ppm; ESI-MS (m/z) 570.5 (M+H)$^+$; Single peak by HPLC (Supelcosil ABZ+Plus 15 cm×4.6 mm, 5 micron reverse phase column, 50% to 100% CH$_3$CN/H$_2$O gradient (0.1% formic acid) over 20 min, 1 mL/min, RT=7.04 min).

EXAMPLE 47

Ethyl (9aS)-5-oxo-4-(5-{[(3-pyridinylcarbonyl)amino]methyl}-2-thienyl)-2-{2-[4- (trifluoromethyl)phenyl]ethyl}-7,8,9,9a-tetrahydro-5H-pyrido[2,3-α]pyrrolizine-3-carboxylate A benzene (20 mL) solution of 950 mg (3.5 mmol) of 5-[(1,3-dioxo-1,3-dihydro-2H-isoindol-2-yl)methyl]-2-thiophenecarbaldehyde and 1 g (3.5 mmol) of tert-Butyl (2S)-2-(3-ethoxy-3-oxopropanoyl)-1-pyrrolidinecarboxylate was refluxed for 2 hr in the presence of 180 µL (0.5 mmol) of piperidine. The reaction flask was fitted with a Dean-Stark trap, 1.05 g (3.5 mmol) of Ethyl (2Z)-3-amino-5-[4-(trifluoromethyl)phenyl]-2-pentenoate was added and the solution was refluxed for 10 hr. The solution was cooled, concentrated, and the crude product was diluted into EtOAc (100 mL), washed with 30 mL 0.5 N HCl and 30 mL brine, and dried over Na$_2$SO$_4$. The isolated crude product was purified by silica gel chromatography (elution with 10% to 50% EtOAc in hexanes) to give 1.75 g of the dihydropyridine intermediate as a yellow-colored solid (foam, 62% yield) after drying under vacuum for several hrs. To a solution of 1.65 g (2.04 mmol) of the above intermediate in 20 mL of CH$_3$CN and 20 mL of water was added 2.24 g (4.08 mmol) of CAN. After stirring at 22° C. for 3 hr, the mixture was diluted with Et$_2$O (100 mL) and washed with water (30 mL) and brine (30 mL). The organics were dried over MgSO$_4$, filtered, and concentrated. The crude product was taken into CH$_2$Cl$_2$ (25 mL), 10 mL of TFA was added, and the solution stirred for 1 hr at 22° C. The reaction was concentrated to dryness several times from CH$_2$Cl$_2$ and the crude product was taken into 15 mL of CH$_2$Cl$_2$ and 10 mL of Et$_3$N. The solution was stirred overnight. The solution was concentrated, then diluted into 75 mL EtOAc and washed with water and brine. The organics were dried over MgSO$_4$, filtered, and concentrated. The crude solid product was triturated with EtOAc (10 mL), filtered, and dried under reduced pressure to give 560 mg of pyrido-pyrrolizine intermediate. The concentrated filtrate was purified by silica gel chromatography (gradient elution with 50% EtOAc/hexanes to 100% EtOAc) to give an additional 530 mg (total yield of 1.09 g, 81%). A suspension of the above intermediate (1.06 g, 1.61 mmol) in EtOH (20 mL) and hydrazine (5 mL) was warmed to effect dissolution and stirred for 14 hr at 22° C. The mixture was partially concentrated and filtered to remove the white solids. The filtrate was concentrated and purified by silica gel chromatography (elution with CH$_2$Cl$_2$, then 1%–20% MeOH in CH$_2$Cl$_2$ to yield 280 mg of intermediate amine as a white solid (foam, 33% yield). To a THF (2 mL) solution of 80 mg (0.15 mmol) of the above amine intermediate was added 78 µL of DIEA followed by 41 mg of nicotinoyl chloride hydrochloride and the resulting solution was stirred for 6 hr at 22° C. The reaction contents were poured into 30 mL of EtOAc and 10 mL of water. The organics were dried over Na$_2$SO$_4$, filtered, and concentrated. The crude product was suspended into ~1 mL of MeOH and ~5 mL of Et$_2$O was added to the rapidly stirred mixture. After stirring for 10 min, the resulting solids were isolated via filtration and dried under vacuum at 60° C. for 14 hr to provide 61 mg (64% yield for the acylation step) of white solid Ethyl (9aS)-5-oxo-4-(5-{[(3-pyridinylcarbonyl)amino]methyl}-2-thienyl)-2-{2-[4-(trifluoromethyl)phenyl]ethyl}-7,8,9,9a-tetrahydro-5H-pyrido[2,3-α]pyrrolizine-3-carboxylate: $^1$H NMR (300 MHz, DMSO) δ 9.45 (t, 1H, J=5.8), 9.03 (s, 1H), 8.72 (d, 1H, J=3.4), 8.21 (d, 1H, J=7.9), 7.62 (d, 2H, J=8.2), 7.52 (dd, 1H, J=7.8, 4.9), 7.41 (d, 2H, J=7.8), 7.10 (d, 1H, J=3.6), 7.06 (d, 1H, J=3.4), 4.74 (m, 1H), 4.68 (d, 2H, J=5.9), 4.06 (t, 2H, J=7.1), 3.55 (m, 1H), 3.3 (m, 1H), 3.1 (m, 4H), 2.6 (m, 3H), 1.31 (m, 1H), 0.94 (t, 3H, J=7.0) ppm, ESI-MS (m/z) 634 (M+H)$^+$; Single peak by HPLC (Supelcosil ABZ+Plus 15 cm×4.6 mm, 5 micron reverse phase column, 50% to 100% CH$_3$CN/H$_2$O gradient (0.1% formic acid) over 20 min, flow 1 mL/min, RT=6.35 min); Anal. calc'd for C$_{33}$H$_{29}$N$_4$O$_4$S$_1$F$_3$: C, 62.45; H, 4.61; N, 8.83; S, 5.05. Found C, 62.33; H, 4.61; N, 8.85; S, 5.06.

EXAMPLE 48

Ethyl (9bS)-6-{4-[(benzyloxy)carbonyl]phenyl}-8-[2-(4-fluorophenyl)ethyl]-5-oxo-2,3,5,9b-tetrahydro-1H-pyrrolo[2.1-a]isoindole-7-carboxylate A. 5-[3-(4-Fluorophenyl)propanoyl]-2,2-dimethyl-1,3-dioxane-4,6-dione To CH$_2$Cl$_2$ (anhydrous, 100 mL) was added DCC (6.71 g, 32.5 mmol) in portions to a stirred solution of 3-(4-fluorophenyl)propionic acid (5.46 g, 32.5 mmol), Meldrum's acid (4.69 g, 32.5 mmol) and DMAP (7.95 g, 65 mmol). After stirring at ambient temperature for 12 h, the reaction mixture was filtered, the filtrate was washed with 1N HCl (50 mL), water (50 mL) and brine (100 mL) and dried over Na$_2$SO$_4$. Filtration and concentration provided the acyl Meldrum's acid derivative as a yellow solid (9.39 g, 31.8 mmol): $^1$H NMR (400 MHz, CDCl$_3$) δ 7.12–7.08 (m, 2H), 6.94–6.89 (m, 2H), 3.41 (t, 2H), 3.05 (t 2H), 1.73 (s, 6H) ppm.

B. tert-Butyl 3-oxo-5-(4-fluorophenyl)pentanoate

The acyl Meldrum's acid (70 g, 0.237 mol) was refluxed in t-Butylalcohol (21.1 g, 0.285 mol) for 6 h. Concentration provided the β-keto ester as a colorless oil (63 g, 0.237 mol, 100%). $^1$H NMR (400 MHz, CDCl$_3$) δ 7.61–7.53 (m, 2H), 7.41–7.34 (m, 2H), 5.44 (s, 1H), 3.57–3.42 (m, 2H), 2.89 (t, 1H), 2.68 (t, 1H), 2.65 (t, 1H), 2.3 (t, 1H), 1.45 (s, 9H). ESI-MS m/z 267 (M+H)$^+$ C. Benzyl (2S)-2-[2-(tert-butoxycarbonyl)-5-(4-fluorophenyl)-3-oxopentanoyl]-1-pyrrolidinecarboxylate To a CH$_2$Cl$_2$ (anhydrous, 25 mL) of N-Carbobenzyloxyl-L-proline (2.4 g, 9.63 mmol) at 0° C. was added thionyl chloride (1.38 g, 11.5 mmol) dropwise and the mixture stirred for 1 hr at ambient temperature. Concentrated and the acid chloride used immediately in two portions. To a THF (anhydrous 25 mL) solution of tert-Butyl 3-oxo-5-(4-fluorophenyl)pentanoate (2.5 g, 9.39 mmol) at −20° C. was added sodium hydride (22.5 mg, 9.39 mmol) and the acid chloride (1.24 g, 4.65 mmol) and the mixture warmed to r.t. for 15 minutes. Then cooled down to −20° C. and sodium hydride (22.5 mg, 9.39 mmol) and the acid chloride (1.24 g, 4.65 mmol) added. The mixture was warmed to r.t. for 0.5 hr and quenched with $H_2O$ (10 mL). The THF removed and the residue dissolved in ethyl acetate (100 ml) and washed with $H_2O$ (25 ml) and dried ($MgSO_4$, 2 g) to provide the desired target material as a solid (3.21 g, 6.45 mmol). $^1$H NMR (400 MHz, $CDCl_3$) δ 7.38–7.21 (m, 2H), 7.20–7.17 (m, 2H), 7.15–7.08 (m, 2H), 6.98–6.91 (m, 3H), 5.44 (s, 1H), 5.16–5.06 (m, 2H), 4.57–4.48 (m, 1H), 3.67–3.63 (m, 1H), 3.57–3.48 (m, 1H), 2.81 (t, 1H), 2.59 (t, 1H), 2.53–2.41 (m, 2H), 2.28 (t, 1H), 2.12–2.06 (m, 2H), 1.99–1.85 (m, 1H), 1.42 (s, 9H). ESI-MS m/z 498 (M+H)$^+$.

D. Benzyl (2S)-2-[2-(tert-butoxycarbonyl)-5-(4-fluorophenyl)-3-oxopentanoyl]-1-pyrrolidinecarboxylate To a $CHCl_3$ (10 ml) of C (5.0 g, 10 mmol) was added TFA (11.4 g, 100 mmol) at r.t. and the mixture stirred for 5 hr. The mixture was then concentrated and purified on $SiO_2$ (3:7 ethyl acetate/hexanes) to provide the target as a pink solid (3.73 g, 9.4 mmol). $^1$H NMR (400 MHz, $CDCl_3$) δ 7.39–7.32 (m, 2H), 7.29–7.22 (m, 3H), 7.16–7.08 (m, 2H), 6.99–6.91 (m, 2H), 5.41 (d, 1H), 5.18–5.08 (m, 2H), 5.04–4.98 (m, 1H), 4.33 (m, 1H), 3.58–3.41 (m, 2H), 2.89 (t, 1H), 2.82 (t, 1H), 2.57 (t, 1H) 2.49 (t, 1H), 2.21–2.05 (m, 1H), 1.96–1.85 (m, 3H) ppm. ESI-MS m/z 398 (M+H)$^+$. HPLC (93%)

Anal. calc'd. for $C_{23}H_{24}NO_4F$: C, 69.49; H, 6.09; N, 3.53. Found: C, 69.32; H, 6.02; N, 3.52.

E. Diethyl 4-{(2S)-1-[(benzyloxy)carbonyl]-2-pyrrolidinyl)-}6[2-(4-fluorophenyl)ethyl]-2-hydroxy-isophthalate To an ethanol (2 ml) solution of D (1.0 g, 2.5 mmol) was added sodium ethoxide (0.17 g, 2.5 mmol) and diethyl 3-oxoglutarate (0.51 g, 2.5 mmol) and the mixture heated at reflux for 3 days. After concentrating the mixture it was purified on $SiO_2$ (3:7 ethyl acetate/hexanes) to provide the target material as a white solid (0.35 g, 0.63mmol). $^1$H NMR (400 MHz, $d_6$-DMSO) δ 10.52 (s, 1H), 7.33–7.28 (m, 2H), 7.27–7.17 (m, 2H), 7.15–7.01 (m, 4H), 6.99–6.85 (m, 1H), 6.40 (s, 1H), 5.03–4.83 (m, 2H), 4.28 (q, 2H), 4.23 (q, 2H), 3.48–3.36 (m, 2H), 2.88–2.65 (m, 4H), 2.22–2.13 (m, 1H), 1.73–1.61 (m, 4H), 1.25 (t, 3H), 1.23 (t, 3H).

F. Ethyl (9bS)-8-[2-(4-fluorophenyl)ethyl]-6-hydroxy-5-oxo-2,3,5,9b-tetrahydro-1H-pyrrolo[2,1-α]isoindole-7-carboxylate To an ethanol (5 mL) solution of E (150 mg, 0.266 mmol) was added 10% Pd/C (10% w/w, 15 mg) and stirred overnight under a ballon of $H_2$. The rxn mixture was filtered through celite (1 g) to provide the desired cyclized adduct (97 mg, 0.252 mmol) as a white solid. $^1$H NMR (400 MHz, $CDCl_3$) δ 9.61 (s, 1H), 7.05–7.02 (m, 2H), 6.93–6.88 (m, 2H), 6.58 (s, 1H), 4.57–4.53 (m, 1H), 4.43–4.38 (q, 2H), 3.65–3.58 (m, 1H), 3.34–3.28 (m, 1H), 3.02–2.98 (m, 2H), 2.86–2.81 (m, 2H), 2.32–2.15 (m, 3H), 1.36 (t, 3H), 1.19–1.13 (m, 1H). ESI-MS m/z 384 (M+H)$^+$. HPLC (96%).

G. Ethyl(9bS)-8-[2-(4-fluorophenyl)ethyl]-5-oxo-6-{[(trifluoromethyl)sulfonyl]oxy}-2,3,5,9b-tetrahydro-1H-pyrrolo[2,1-α]isoindole-7-carboxylate To a solution of F (100 mg, 0.26 mmol) in $CH_2Cl_2$ (anhydrous, 25 mL) at 0° C. was added triethylamine (34 mg, 0.312 mmol) and trifluoromethanesulfonic anhydride (110 mg, 0.392 mmol). The mixture was warmed to r.t. and stirred for an additional 3 hrs. It was then washed with $H_2O$ (20 ml), dried ($MgSO_4$, 2 g) and concentrated to provide a red oil (102 mg, 198 mmol) as the triflate. $^1$H NMR (400 MHz, $CDCl_3$) δ 7.09 (s, 1H), 7.08–7.01 (m, 2H), 6.99–6.91 (m, 2H), 4.65–4.58 (m, 1H), 4.38 (q, 2H), 3.79–3.71 (m, 1H), 3.42–3.38 (m, 1H), 3.04–2.94 (m, 1H), 2.91–2.85 (m, 1H), 2.39–2.24 (m, 2H), 1.64 (brm, 1H), 1.29 (t, 3H), 1.25–1.06 (m. 3H) ppm.

H. To a solution of triflate (100 mg, 194 mmol) in dioxane (anhydrous, 25 ml) was added potassium phosphate (81 mg, 0.38 mmol), potassium bromide (2.3 mg, 0.019 mmol), tetrakis(triphenylphosphine)palladium (11 mg, 0.009 mmol) and Benzyloxycarbonate-4-phenyl boronic acid (prepared from the benzylation of 4-carboxyboronic acid) (73 mg, 0.29 mmol) and $H_2O$ (5 drops). The mixture was heated at 60° C. for 4 hrs and then 100° C. for 5 hrs. Afterwards, the mixture was concentrated and diluted with $CH_2Cl_2$ (500 ml) and washed with sat. $NaHCO_3$ (200 ml) and brine (100 ml) and dried ($MgSO_4$, 2 g) and concentrated to provide an oil that was purified on $SiO_2$ (ethyl acetate/hexane 2:8) to provide the desired biphenyl adduct as a colorless oil (78 mg, 136 mmol). $^1$H NMR (400 MHz, $CDCl_3$) δ 8.10–8.07 (m, 2H), 7.44–7.39 (m, 5H), 7.37–7.32 (m, 2H), 7.12 (s, 1H), 7.09–7.06 (m, 2H), 6.96–6.92 (m, 2H), 5.36 (s, 2H), 4.60–4.56 (m, 1H), 3.97–3.91 (m, 2H), 3.62–3.59 (m, 1H), 3.31–3.26 (m, 1H), 3.01–2.90 (m, 4H), 2.30–2.23 (m, 2H), 1.25–1.20 (m, 2H), 0.87 (t, 3H) ppm. ESI-MS m/z 578 (M+H)$^+$. HPLC (99%) Anal. calcd. for $C_{36}H_{32}NO_5F$ ¾$H_2O$: C, 73.14; H, 5.71; N, 2.37. Found: C, 73.22; H, 5.56; N, 2.27.

EXAMPLE 49

4-{(9bS)-7-(ethoxycarbonyl)-8-[2-(4-fluorophenyl)ethyl]-5-oxo-2,3,5,9b-tetrahydro-1H-pyrrolo[2,1-α]isoindol-6-yl}benzoic acid To a solution of Example 48 (300 mg, 0.51 mmol) in ethyl acetate (25 ml) was added 10% Pd/C (10% w/w, 30 mg) and was stirred under $H_2$ (1 atms.) for 18 hr. The Pd/C filtered through celite (1 g) and the filtrate concentrated to provide title compound as a white solid (243 mg, 0.50 mmol). $^1$H NMR (400 MHz, $CDCl_3$) δ 8.07 (d, J=8.4 Hz, 2H), 7.49–7.42 (m, 2H), 7.13 (s, 1H), 7.09–7.06 (m, 2H), 6.96–6.92 (m, 2H), 4.62–4.58 (m, 1H), 3.94 (q, 2H), 3.68–3.61 (m, 1H), 3.33–3.29 (m, 1H), 3.02–2.87 (m, 4H), 2.32–2.03 (m, 3H), 1.24–1.19 (m, 1H), 0.86 (t, 3H) ppm. ESI-MS m/z 488 (M+H)$^+$. HPLC (93%).

EXAMPLE 50

Ethyl (9bS)-8-[2-(4-flurophenyl)ethyl]-6-(4-{[(2-furylmethyl)amino]carbonyl}phenyl)-5oxo-2,3,5,9b-tetrahydro-1H-pyrrolo[2,1-α]isoindole-7-carboxylate A solution of Example 49 (241 mg, 0.49 mmol) and carbonyldimidazole (0.54 mmol, 88.2 mg) in THF (anhydrous, 15 ml) was stirred for 1 hr at r.t. Then was added dropwise a solution of furfurylamine (96.1 mg, 0.99 mmol)

in THF (2 ml) and the mixture stirred at r.t. for 12 hr. Then the reaction mixture concentrated and the yellow oil purified on $SiO_2$ (ethyl acetate:hexanes 1:5) to afford the title compound as a white solid (194 mg, 343 mmol): $^1$H NMR (400 MHz, $d_6$-DMSO) δ 9.03 (t, 1H), 7.82 (d, J=8.6 Hz, 2H), 7.53 (d, J=8.2 Hz, 2H), 7.26 (d, J=8.2 Hz, 2H), 7.20–7.17 (m, 2H), 7.09–7.04 (m, 2H), 6.36 (d, J=4.0 Hz, 1H), 6.25 (d, J=4.0 Hz, 1H), 4.69–4.65 (m, 1H), 4.46–4.44 (m, 2H), 3.91 (q, 2H), 3.39–3.36 (m, 1H), 3.19–3.13 (m, 1H), 2.90–2.79 (m, 4H), 2.28–2.18 (m, 3H), 1.13–1.08 (m, 1H), 1.08 (t, 3H) ppm. ESI-MS m/z 567 (M+H)$^+$. HPLC (99%). Anal. calcd. for $C_{34}H_{31}N_2O_5F$ 0.41$H_2O$: C, 71.14; H, 5.59; N, 4.88. Found: C, 71.14; H, 5.66; N, 4.84.

EXAMPLE 51

Ethyl (9aS)-4-(4-{[(2-furylmethyl)amino]carbonyl}phenyl)-5-oxo-2-(3-thienylmethyl)-7,8,9,9a-tetrahydro-5H-pyrido[2,3-α]pyrrolizine-3-carboxylate A. Ethyl 3-oxo-4-(3-thienyl)butanoate A stirred solution of 711 mg (5.0 mmol) of 3-thienylacetic acid, 720 mg (5.0 mmol) of Meldrum's acid, and 610 mg (5.0 mmol) of 4-dimethylaminopyridine in 10 mL of DCM was treated with a solution of 1.03 g (5.0 mmol) of DCC in 10 mL of DCM. The resulting solution was stirred at room temperature for 16 h, during which time a white precipitate appeared in the reaction mixture. The reaction mixture was filtered through a pad of Celite to remove the precipitated dicyclohexylurea and the filtrate was washed successively with 1 N HCl (1×15 mL), $H_2O$ (1×15 mL), brine (1×15 mL). The filtrate was dried (MgSO$_4$) and solvents were removed in vacuo. The resulting crude oil was dissolved in 8 mL of absolute ethanol and heated to 80° C. for 4 h. The reaction mixture was cooled to room temperature and ethanol was removed in vacuo. Purification of the resulting oil by silica gel flash column chromatography eluting with hexanes/EtOAc 2:1 afforded 1.02 g (97%) of the title compound as a yellow oil: $^1$H NMR (CDCl$_3$, 400 MHz) δ 7.27 (m, 1H), 7.06 (s, 1H), 6.92 (m, 1H), 4.09 (q, 2H, J=6.8), 3.83 (s, 2H), 3.41 (s, 2H), 1.22 (t, 3H, J=6.8).

B. 4-[(9aS)-3-(ethoxycarbonyl)-5-oxo-2-(3-thienylmethyl)-7,8,9,9a-tetrahydro-5H-pyrido[2,3-α]pyrrolizin-4-yl]benzoic acid A stirred solution of 530 mg (2.5 mmol) of ethyl 3-oxo-4-(3-thienyl)butanoate, 375 mg (2.5 mmol) of 4-fornylbenzoic acid, and 106 mg (1.25 mmol) of piperidine in 5 mL of DMF was treated with 0.5 mL (1.2 eq, 3.0 mmol) of triethylorthoformate. The resulting solution was stirred 10 minutes at room temperature then heated to 80° C. for 45 minutes, until the starting β-ketoester was consumed as judged by TLC. The reaction mixture was cooled to room temperature, diluted with 20 mL Et$_2$O, and extracted with 1 N HCl (1×15 mL and H$_2$O (2×15 mL). The organic layer was separated, dried (MgSO$_4$), and the solvents were removed in vacuo to afford 4-[(1E)-2-(ethoxycarbonyl)-3-oxo-4-(3-thienyl)-1-butenyl]benzoic acid as a light yellow oil which was used directly without further purification. The material was dissolved in 0.5 mL triethylorthoformate and then 640 mg (2.25 mmol) of tert-butyl (2R)-2-[(1Z)-1-amino-3-ethoxy-3-oxo-1-propenyl]-1-pyrrolidinecarboxylate was added. The resulting mixture was heated to 110° C. for 18 h and then cooled to room temperature. The crude dihydropyridine adduct was isolated by silica gel flash column chromatography using a gradient solvent elution of hexanes/EtOAc 3:1 to 1:1 to 1:3 to afford 237 mg of a clear yellow oil which contained impurities by TLC; MS m/e=610. This material was also used directly in the next reaction sequence without further purification. The material was dissolved in 2 mL of CH$_3$CN and then 2 mL of H$_2$O was added, followed by 426 mg (0.77 mmol) of ceric ammonium nitrate. The resulting reaction mixture was stirred rapidly at room temperature for 1 h until comsuption of starting material as judged by TLC. (CHCl$_3$/MeOH 20:1). The reaction mixture was then diluted with 10 mL Et$_2$O and extracted with H$_2$O (1×10 mL). The organic layer was separated, dried (MgSO$_4$), and solvents removed in vacuo. The residue was dissolved in 2 mL DCM and 2 mL of trifluoroacetic acid was added. The resulting reaction mixture was stirred 4 h at room temperature, and then solvent and excess trifluoroacetic acid were removed in vacuo. The residue was redissolved in 2 mL DCM and 2 mL of Et$_3$N was added. The resulting reaction mixture was stirred at room temperature for 24 h. The reaction was then concentrated in vacuo and the residue was diluted with 15 mL CHCl$_3$ and extracted with pH 4.0 aqueous buffer (1×10 mL), H$_2$O (1×10 mL) and brine (1×10 mL). The organic layer was separated, dried (MgSO$_4$), and solvents were removed in vacuo. Purification of the residue by silica gel flash column chromatography using a gradient elution of hexanes/EtOAc 1:2 to hexanes/EtOAc 1:2+1% AcOH to hexanes/EtOAc 1:4+1% AcOH afforded 30 mgs of the title compound as a light orange oil: $^1$H NMR (CDCl$_3$, 400 MHz) δ 8.07 (d, 2H, J=7.9), 7.42 (d, 2H, J=7.9), 7.19 (m, 1H), 7.02 (s, 1H), 6.97 (d, 1H, J=5.0), 4.72 (dd, 1H, J=6.2, 10.1), 4.33 (AB quartet, 2H, J=16.5, 44.1), 3.86 (q, 2H, J=7.1), 3.68 (m, 1H), 3.09 (dd, 1H, J=7.4, 13.2), 2.47 (m, 1H), 2.32 (m, 2H), 1.42–1.14 (m, 4H), 10.76 (t, 3H, J=7.1); low resolution MS (ES$^+$) m/e 463 (MH$^+$); TLC (hexanes/EtOAc (1:2)+1% AcOH): R$_f$=0.20.

C. A stirred solution of 28 mg (0.060 mmol) of 4-[(9aS)-3-(ethoxycarbonyl)-5-oxo-2-(3-thienylmethyl)-7,8,9,9a-tetrahydro-5H-pyrido[2,3-α]pyrrolizin-4-yl]benzoic acid, 14 mg (1.2 equiv, 0.072 mmol) of EDCI and 10 mg (1.2 equiv., 0.072 mmol) of HOBT in 1 mL of DCM was treated with 13 mg (2.2 equiv., 0.133 mmol) of 2-furfurylamine. The resulting solution was stirred at room temperature for 3 h. The reaction mixture was then poured into Et$_2$O (10 mL) and extracted with H$_2$O (1×10 mL) and NaHCO$_3$ (1×10 mL). The organic layer was separated, dried (MgSO$_4$), filtered to remove solids, and concentrated in vacuo. The resulting crude material was purified by silica gel chromatography on an Elution Solutions medium pressure chromatography system using a gradient elution of hexanes/EtOAc 1:1 to 1:4 to afford a clear golden oil. The oil was then triturated with Et$_2$O to afford 22 mg (68%) the title compound as a light yellow solid: $^1$H NMR (CDCl$_3$, 400 MHz) δ 7.78 (d, 2H, J=7.9), 7.40 (d, 2H, J=7.9), 7.35 (s, 1H), 7.19 (m, 1H), 7.02 (s, 1H), 6.97 (d, 1H, J=4.8), 6.47 (m, 1H), 6.29 (d, 2H, J=15.4), 4.70 (dd, 1H, J=6.3, 10.2), 4.61 (d, 2H, J=5.4), 4.33 (AB quartet, 2H, J=14.5, 41.7), 3.86 (q, 2H, J=6.9), 3.65 (m, 1H), 2.47 (m, 1H), 2.30 (m, 2H), 1.41 (m, 1H), 1.22 (m, 2H), 1.18 (t, 3H, J=6.9); low resolution MS (ES$^+$) m/e 543, (MH+1), 542 (MH$^+$); TLC (hexanes/EtOAc (1:5)): R$_f$=0.25; HPLC (Dynamax RP-18, 4.6 mm×25 cm; 50–100% CH$_3$CN/H$_2$O with 0.1% TFA; 25 minutes; 1 mL/min): t$_R$=7.73 min, 97% purity; Anal. (C$_{30}$H$_{27}$N$_3$O$_5$S) Calc. C, 66.53; H, 5.02; N, 7.76. Found C, 66.26; H, 4.87; N, 7.96.

EXAMPLE 52

Ethyl (9aS)-2-[2-(4-fluorophenyl)ethyl]-4-[3-fluoro-4-({[(1S)-1-(4-pyridinyl)ethyl]amino}carbonyl)phenyl]-5-oxo-7,8,9,9a-tetrahydro-5H-pyrido[2,3-α]pyrrolizine-3-carboxylate tert-Butyl (2S)-2-(3-ethoxy-3-oxopropanoyl)-1-pyrrolidinecarboxylate (0.096 g, 0.22 mmol, 1 equiv), ethyl (2Z)-3-amino-5-(4-fluorophenyl)-2-pentenoate (0.052 g, 0.22 mmol, 1 equiv), 4-carboxy-3-fluorobenzaldehyde (0.037 g, 0.22 mmol, 1 equiv), and piperidine (0.011 mL, 0.11 mmol, 0.5 equiv) were combined in toluene (0.5 mL). After 2 h at 90° C., the reaction was cooled to ambient temp. CAN (0.24 g, 0.44 mmol, 2 equiv) and H$_2$O (0.5 mL) were added. After 0.5 h the layers were separated. The aqueous portion was extracted with EtOAc (2×1 mL) and the combined organic portions were concentrated to a brown oil. The crude oil was then treated with 4 N HCl in dioxane (1.0 mL). After 1 h, the mixture was concentrated to a brown oil. A CH$_2$Cl$_2$ solution (1.0 mL) of this crude oil was treated with Et$_3$N (0.15 mL, 1.10 mmol, 5 equiv). After 8 h, the mixture was concentrated to a brown foam. A solution of the crude foam (0.028 g, 0.06 mmol, 1 equiv) in CH$_2$Cl$_2$ (0.5 mL) was treated with (−)-α-4-(pyridyl)ethylamine (0.015 g, 0.12 mmol, 2 equiv), EDCI (0.013 g, 0.07 mmol, 1.2 equiv), and HOBt (0.009 g, 0.07 mmol, 1.2 equiv). After 12 h at ambient temperature, the reaction was diluted with CH$_2$Cl$_2$ (1.0 mL) and treated with saturated aqueous NaHCO$_3$ (1 mL). The organic portion was the washed with 1N HCl (1 mL) followed by brine (1 mL). Concentration gave a brown oil that was chromatographed radially (SiO$_2$, 1 mm plate, EtOAc) to provide the title compound as a pale yellow foam (0.020 g, 59%): $^1$H NMR (CDCl$_3$, 400 MHz) δ 8.60 (d, J=5.1 Hz, 2H), 8.08 (t, J=8.2 Hz, 1H), 7.40 (d, J=5.2 Hz, 2H), 7.25–7.21 (m, 2H), 7.17–7.13 (m, 2H), 7.06–7.03 (m, 1H), 6.95 (t, J=8.6 Hz, 2H), 5.33–5.30 (m, 1H), 4.72 (dd, J=10.3, 6.3 Hz, 1H), 4.10–4.02 (m, 2H), 3.74–3.67 (m, 1H), 3.41–3.35 (m, 1H), 3.20–3.02 (m, 4H), 2.50.2.45 (m, 1H), 2.37–2.29 (m, 2H), 1.60 (d, J=7.2 Hz, 3H), 1.43–1.33 (m, 1H), 1.00 (t, J=7.1 Hz, 3H); low resolution MS (ES$^+$) m/e 611 (MH$^+$); RP-HPLC (Dynamax C-18 25 cm×4.1 mm; 50–100% CH$_3$CN in H$_2$O with 0.1% TFA buffer; 30 minutes; 1 mL/min) t$_r$=6.37 min, 95% purity.

EXAMPLE 53

Ethyl (9aS)-4-(4-{[(1R)-2,3-dihydro-1H-inden-1-ylamino]carbonyl}-2-nitrophenyl)-2-[2-(4-fluorophenyl)ethyl]-5-oxo-7,8,9,9a-tetrahydro-5H-pyrido[2,3-α]pyrrolizine-3-carboxylate A. tert-Butyl (2S)-2-(3-ethoxy-3-oxopropanoyl)-1-pyrrolidinecarboxylate (1.40 g, 3.14 mmol, 1 equiv), ethyl (2Z)-3-amino-5-(4-fluorophenyl)-2-pentenoate (0.744 g, 3.14 mmol, 1 equiv), 4-carboxy-2-nitrobenzaldehyde (0.613 g, 3.14 mmol, 1 equiv), and piperidine (0.155 mL, 1.57 mmol, 0.5 equiv) were combined in toluene (8.0 mL). After 2 h at 90° C., the reaction was cooled to ambient temp. CAN (3.44 g, 6.28 mmol, 2 equiv) and H$_2$O (8.0 mL) were added. After 0.5 h the layers were separated. The aqueous portion was extracted with EtOAc (2×8 mL) and the combined organic portions were concentrated to a brown oil. The crude oil was then treated with 4 N HCl in dioxane (10.0 mL). After 1 h, the mixture was concentrated to a brown oil. A CH$_2$Cl$_2$ solution (8.0 mL) of this crude oil was treated with Et$_3$N (2.18 mL, 15.7 mmol, 5 equiv). After 8 h, the mixture was concentrated to a brown foam. A solution of the crude foam (0.070 g, 0.13 mmol, 1 equiv) in CH$_2$Cl$_2$ (1.0 mL) was treated with (R)-(−)-1-aminoindane (0.035 g, 0.26 mmol, 2 equiv), EDCI (0.038 g, 0.20 mmol, 1.5 equiv), and HOBt (0.027 g, 0.20 mmol, 1.5 equiv). After 12 h at ambient temperature, the reaction was diluted with CH$_2$Cl$_2$ (1.0 mL) and treated with saturated aqueous NaHCO$_3$ (2 mL). The organic portion was the washed with 1N HCl (2 mL) followed by brine (2 mL). Concentration gave a brown oil that was chromatographed radially (SiO$_2$, 1 mm plate, 50% hexanes-EtOAc) to the title compound as a pale yellow foam (0.049 g, 58%): low resolution MS (ES$^+$) m/e 649 (H$^+$); RP-HPLC (Dynamax C-18 25 cm×4.1 mm; 50–100% CH$_3$CN in H$_2$O with 0.1% TFA buffer; 30 minutes; 1 mL/min) t$_r$=13.78 min, 97% purity.

EXAMPLE 54

Ethyl (9aS)-2-(4-fluorobenzyl)-5-oxo-4-[3-({[2-(2-thienyl)ethyl]amino}carbonyl)-5-(trifluoromethyl)phenyl]-7,8,9,9a-tetrahydro-5H-pyrido[2,3-α]pyrrolizine-3-carboxylate A. tert-Butyl (2S)-2-(3-ethoxy-3-oxopropanoyl)-1-pyrrolidinecarboxylate (0.409 g, 0.92 mmol, 1 equiv), ethyl (2Z)-3-amino-4-(4-fluorophenyl)-2-butenoate (0.204 g, 0.92 mmol, 1 equiv), 3-carboxy-5-trifluoromethylbenzaldehyde (0.201 g, 0.92 mmol, 1 equiv), and piperidine (0.045 mL, 0.46 mmol, 0.5 equiv) were combined in toluene (4.0 mL). After 2 h at 90° C., the reaction was cooled to ambient temp. CAN (1.01 g, 1.84 mmol, 2 equiv) and H$_2$O (4.0 mL) were added. After 0.5 h the layers were separated. The aqueous portion was extracted with EtOAc (2×4 mL) and the combined organic portions were concentrated to a brown oil. The crude oil was then treated with 4 N HCl in dioxane (5.0 mL). After 1 h, the mixture was concentrated to a brown oil. A CH$_2$Cl$_2$ solution (4.0 mL) of this crude oil was treated with Et$_3$N (0.64 mL, 4.6 mmol, 5 equiv). After 8 h, the mixture was concentrated to a brown foam. A solution of the crude foam (0.105 g, 0.19 mmol, 1 equiv) in CH$_2$Cl$_2$ (1.0 mL) was treated with 2-(2-thienyl)ethylamine (0.043 g, 0.39 mmol, 2 equiv), EDCI (0.056 g, 0.29 mmol, 1.5 equiv), and HOBt (0.039 g, 0.29 mmol, 1.5 equiv). After 12 h at ambient temperature, the reaction was diluted with CH$_2$Cl$_2$ (1.0 mL) and treated with saturated aqueous NaHCO$_3$ (2 mL). The organic portion was the washed with 1N HCl (2 mL) followed by brine (2 mL). Concentration gave a brown oil that was chromatographed radially (SiO$_2$, 1 mm plate, 50% hexanes-EtOAc) to X as a pale yellow foam (0.039 g, 31%): low resolution MS (ES$^+$) m/e 652 (MH$^+$); RP-HPLC (Dynamax C-18 25 cm×4.1 mm; 50–100% CH$_3$CN in H$_2$O with 0.1% TFA buffer; 30 minutes; 1 mL/min) t$_r$=14.37 min, 98% purity.

EXAMPLE 55

Ethyl (9aS)-4-{4-[(2,3-dihydro-1H-indol-1-ylamino)carbonyl]phenyl}-2-(4-fluorobenzyl)-5-oxo-7,8,9,9a-tetrahydro-5H-pyrido[2,3-α]pyrrolizine-3-carboxylate A. 4-[(9aS)-3-(ethoxycarbonyl)-2-(4-fluorobenzyl)-5-oxo-7,8,9,9a-tetrahydro-5H-pyrido[2,3-α]pyrrolizin-4yl]benzoic acid tert-Butyl (2S)-2-(3-ethoxy-3-oxopropanoyl)-1-pyrrolidinecarboxylate (14.0 g, 49.1 mmol, 1 equiv), ethyl (2Z)-3- amino-4-(4-fluorophenyl)-2-butenoate (11.0 g, 49.1 mmol, 1 equiv), 4-carboxybenzaldehyde (7.37 g, 49.1 mmol, 1 equiv), and piperidine (2.43 mL, 24.5 mmol, 0.5 equiv) were combined in toluene (50 mL). After 2 h at 90° C., the reaction was cooled to ambient tempand concentrated. The residue was redissolved in 70 mL of $CH_3CN$ and 70 mL of $H_2O$ and then CAN (63.8 g, 98.3 mmol, 2 equiv) was added. After 0.5 h the reaction mixture was extracted with EtOAc (2×100 mL) and the combined organic portions were concentrated to a brown oil. The crude oil was then treated with TFA (50 mL). After 1 h, the mixture was concentrated to a brown oil. A $CH_2Cl_2$ solution (100 mL) of this crude oil was treated with $Et_3N$ (10 mL). After 8 h, the mixture was concentrated to a brown foam. The residue was redissolved in EtOAc and washed 1× NaHCO3, 1× H2O. The organics were then dried (Na2SO4), filtered and concentrated. Chromatography on silica gel using 90% EtOAc/ 10% MeOH eluted the product. Upon concentration the material was isolated as a white solid: $^1H$ NMR (CDCl$_3$, 400 MHz) δ 8.07 (d, J=8.3 Hz, 2H), 7.43 (d, J=8.0 Hz, 2H), 7.24 (dd, J=8.4, 2.9 Hz, 2H), 6.94 (t, J=8.6 Hz, 2H), 4.75 (dd, J=10.5, 6.5 Hz, 1H), 4.31 (dd, J=28.7, 14.4 Hz, 2H), 3.84 (dd, J=14.3, 7.2 Hz, 2H), 3.76–3.69 (m, 1H), 3.40–3.35 (m, 1H), 2.53–2.48 (m, 1H), 2.34–2.26 (m, 2H), 1.44–1.39 (m, 1H), 0.74 (t, J=7.2 Hz, 3H).

B. A solution of 4-[(9aS)-3-(ethoxycarbonyl)-2-(4-fluorobenzyl)-5-oxo-7,8,9,9a-tetrahydro-5H-pyrido[2,3-α]pyrrolizin-4yl]benzoic acid (0.200 g, 0.42 mmol, 1 equiv) in $CH_2Cl_2$ (1.0 mL) was treated with the 1-indolinamine (ref. Wijngaarden, I. et al., *J Med Chem*, 1993, 36, 3693–99) (0.113 g, 0.84 mmol, 2 equiv), EDCI (0.113 g, 0.59 mmol, 1.4 equiv), and HOBt (0.080 g, 0.59 mmol, 1.4 equiv). After 12 h at ambient temperature, the diluted with $CH_2Cl_2$ (1.0 mL) and treated with saturated aqueous NaHCO3. The organic potion was the washed with 1N HCl (1 mL) followed by brine (1 mL). Concentration gave a brown oil the was chromatographed radially (SiO$_2$, 2 mm plate, 50% hexanes-EtOAc) to provide the title compound as a white solid (0.206 g, 83%): $^1H$ NMR (CDCl$_3$, 400 MHz) δ 7.86 (d, J=8.2 Hz, 2H), 7.68 (s, 1H), 7.45 (d, J=8.0 Hz, 2H ), 7.25–7.21 (m, 2H), 7.15–7.10 (m, 2H), 6.94 (t, J=8.6 Hz, 2H), 6.86 (t, J=7.4 Hz, 1H), 6.71 (d, J=7.7 Hz, 1H), 4.74 (dd, J=10.4, 6.2 Hz, 1H), 4.35 (d, J=14.3 Hz, 1H), 4.29 (d, J=14.3 Hz, 1H), 3.90 (q, J=6.8 Hz, 2H), 3.69–3.61 (m, 3H), 3.36–3.31 (m, 1H), 3.09–3.05 (m, 2H), 2.53–2.47 (m, 1H), 2.35–2.27 (m, 2H), 1.45–1.34 (m, 1H), 0.84 (t, J=7.1 Hz, 3H).

EXAMPLE 56

Ethyl (9aS)-4-(4-bromo-2-thienyl)-2-[2-(4-fluorophenyl)ethyl]-5-oxo-7,8,9,9a-tetrahydro-5H-pyrido[2,3-α]pyrrolizine-3-carboxylate tert-Butyl (2S)-2-(3-ethoxy-3-oxopropanoyl)-1-pyrrolidinecarboxylate (0.445 g, 1.00 mmol, 1 equiv), ethyl (2Z)-3-amino-5-(4-fluorophenyl)-2-pentenoate (0.237 g, 1.00 mmol, 1 equiv), 4-bromo-2-thiophenecarboxaldehyde (0.191 g, 1.00 mmol, 1 equiv), and piperidine (0.05 mL, 0.5 mmol, 0.5 equiv) were combined in toluene (2.0 mL). After 2 h at 90° C., the reaction was cooled to ambient temp. CAN (1.64 g, 3.00 mmol, 3 equiv) and $H_2O$ (2.0 mL) were added. After 0.5 h the layers were separated. The aqueous portion was extracted with EtOAc (2×4 mL) and the combined organic portions were concentrated to a brown oil. The crude oil was then treated with 4 N HCl in dioxane (2.0 mL). After 1 h, the mixture was concentrated to a brown oil. A $CH_2Cl_2$ solution (2.0 mL) of this crude oil was treated with $Et_3N$ (0.70 mL, 5.0 mmol, 5 equiv). After 8 h, the mixture was concentrated to a brown oil and radially chromatographed (SiO$_2$, 2 mm plate, 50% hexanes-EtOAc) to provide the title compound as a pale yellow foam (0.088 g, 17%): $^1H$ NMR (CDCl$_3$, 400 MHz) δ 7.40 (d, J=1.5 Hz, 1H), 7.17–7.13 (m, 3H), 6.98–6.93 (m, 2H), 4.69 (dd, J=10.4, 6.2 Hz, 1H), 4.22–4.14 (m, 2H), 3.78–3.71 (m, 1H), 3.43–3.37 (m, 1H), 3.17–3.02 (m, 4H), 2.51–2.44 (m, 1H), 2.37–2.29 (m, 2H), 1.39–1.34 (m, 1H), 1.11 (t, J=7.1 Hz, 3H).

EXAMPLE 57—FORMULA (II)

Ethyl (9aS)-2-[2-(4-methoxyphenyl)ethyl]-5-oxo-4-(4-{[(2-pyridinylmethyl)amino]carbonyl}phenyl)-5,7,8,9,9a,10-hexahydropyrrolo[1,2-g][1,6]naphthyridine-3-carboxylate A. tert-Butyl (2S)-2-(diazoacetyl)-1-pyrrolidinecarboxylate Boc L-Proline (11 g, 50. mmol) was dissolved in 100 mL anhydrous ether and TEA (5.0 g, 50 mmol, 7.0 mL) and cooled to −14° C. Ethyl chloroformate (5.4 g, 50 mmol, 4.8 mL) was added dropwise via syringe. After 30 min the reaction mixture was filtered to remove TEA hydrochloride and the filtrate was cooled to 5° C. Diazomethane (generated from 25 g Diazald; 117 mmol theor.) was added. The reaction mixture was stirred overnight at 5° C. The reaction mixture was concentrated in vacuo, taken up in fresh ether and washed with NaHCO$_3$ (3×) and brine and dried over MgSO$_4$. Norit was added and the solution was filtered through Celite and concentrated to provide the diazoketone as a yellow oil (17.3 g): $^1H$ NMR (400 MHz, CDCl$_3$, mixture of rotamers) δ 5.55 (bs, 0.5H), 5.41 (bs, 0.5H), 4.4–4.2 (m, 1H), 3.6–3.3 (m, 2H), 2.3–1.8 (m, 4H), 1.49 (s, 4.5H), 1.43 (s, 4.5H) ppm. ES-MS m/z 240 (MH)$^+$.

B. tert-Butyl (2S)-2-(2-methoxy-2-oxoethyl)-1-pyrrolidinecarboxylate tert-Butyl (2S)-2-(diazoacetyl)-1-pyrrolidinecarboxylate (16 g, 46 mmol) was dissolved in 50 mL anhydrous methanol. Silver benzoate (0.1 mL of a 1 g solution in 12 mL TEA) was added. After 14 at room temperature, Norit was added and the mixture was concentrated in vacuo. Purifcation on SiO$_2$ (hexanes:EtOAc 6:1 then 4:1) provided the methyl ester as a clear oil (8.35 g, 34.3 mmol, 69% from Boc-proline): $^1H$ NMR (400 MHz, CDCl$_3$) δ 4.12 (bs, 1H), 3.65 (s, 3H), 3.34 (m, 2H), 2.85 (m, 1H), 2.29 (dd, J=9.6, 15.2 Hz, 1H), 2.1 (m, 1H), 1.8–1.6 (m, 3H), 1.44 (s, 9H) ppm. ESMS m/z 244 (MH)$^+$, 144 (MH−$C_5H_8O_2$)$^+$.

C. [(2S)-1-(tert-Butoxycarbonyl)pyrrolidinyl]acetic acid tert-Butyl (2S)-2-(2-methoxy-2-oxoethyl)-1-pyrrolidinecarboxylate (8.35 g, 34.3 mmol) was dissolved in 150 mL MeOH. Aqueous NaOH (50 mL, 1 M) was added and the reaction mixture was allowed to stand overnight. After concentration in vacuo to ca. 100 mL, the solution was added to 300 mL water and extracted with ether (2×). The carboxylate solution was acidified to pH 2 with 12 N HCl and extracted with ether (2×). The aqueous layer was saturated with salt and extracted a third time with ether. The combined organic layers were washed with water, brine and dried over MgSO$_4$. Filtration and concentration provided the title acid as a white solid (7.28 g, 31.7 mmol, 92.6%): $^1$H NMR (300 MHz, CDCl$_3$, mixture of rotamers) δ 4.16 (bs, 1H), 3.37 (bs, 2H), 3.0–2.8 (bs, 1H), 2.36 (dd, J=9.3, 15.3 Hz, 1H), 2.2–2.0 (m, 1H), 1.9–1.7 (m, 4H), 1.48 (s, 9H) ppm.

D. tert-Butyl (2S)-2-[2-(2,2-dimethyl-4,6-dioxo-1,3-dioxan-5-yl)-2-oxoethyl]-1-pyrrolidinecarboxylate DCC (2.7 g, 13 mmol) was added in portions to a stirred solution of [(2S)-1-(tert-butoxycarbonyl)pyrrolidinyl]acetic acid (3.0 g, 13 mmol), Meldrum's acid (1.9 g, 13 mmol) and DMAP (3.2 g, 26 mmol) in 40 mL DCM. After stirring at ambient temperature for 18 h, the reaction mixture was filtered through Celite, the filtrate was washed with 1N HCl (2×), water and brine and dried over Na$_2$SO$_4$. Filtration and concentration provided the acyl Meldrum's acid derivative as a yellow solid (4.8, 13 mmol, 100%): $^1$H NMR (300 MHz, CDCl$_3$) δ 4.4 (m, 1H), 3.5–3.2 (m, 4H), 2.2–1.8 (m, 3H), 1.8–1.7 (m, 2H), 1.78 (s, 3H), 1.76 (s, 3H), 1.45 (s, 9H) ppm. ESMS m/z pos. ion: 356 (MH)$^+$, neg. ion: 354 (M–H)$^+$.

E. Polymer-bound tert-butyl (3-oxopropanoyl)-1-pyrrolidinecarboxylate (1.0 g, 0.44 meq/g, 0.44 mmol) was suspended in 10 mL anhydrous DMF and 4-formylbenzoic acid (1.5 g, 9.8 mmol) was added followed by piperidine (0.1 mL), and trimethyl orthoformate (0.32 mL). After 5 h at 65° C., the resin was filtered and washed as above and resuspended in 6 mL fresh DMF. Ethyl (2Z)-3-amino-5-(4-methoxyphenyl)-2-pentenoate (1.2 g, 4.9 mmol) was added followed by trimethyl orthoformate (0.32 mL) and the sealed reaction mixture was heated at 80° C. for 16 h. The resin was filtered and washed as before. The resin was suspended in DCM (10 mL) and DDQ (0.2 g, 0.98 mmol) was added. The brown suspension was shaken at room temperature for 10 min then filtered and washed as before. The resin was dried overnight at 30° C. under high vacuum. The resin was suspended in 5 mL DMF and 2 mL pyridine. Pentafluorophenyl trifluoracetate (1.4 g, 4.8 mmol, 0.84 mL) was added and the sealed reaction tube was shaken at room temperature for 45 min, filtered and washed as above and dried under high vacuum overnight. To 40 mg of (0.014 mmol, 0.35 meq/g) suspended in DCM (1 mL) was added DMAP (10 mg) and 2-aminomethylpyridine (0.015 mg, 0.14 mmol, 0.014 mL) and the reaction mixture was shaken at room temperature for 4 h. The resin was filtered and washed as before. The resin was suspended in 1 mL TFA:DCM:phenol:thioanisole (70:20:5:5) and shaken for 3 h, filtered and washed. The resin was shaken in 2 mL 5% TEA in DCM for 36 h. The resin was filtered into a collection flask and rinsed with additional DCM (3×). The filtrate was concentrated and the product was purified by preparative thin-layer chromatography (SiO$_2$, 10% MeOH in EtOAc) to give the title compound as white solid (6.3 mg, 0.010 mmol, 74%): mp=>200° C. $^1$H NMR (300 MHz, CDCl$_3$) δ 8.58 (d, J=4.5 Hz, 1H), 7.88 (m, 2H), 7.70 (m, 1H), 7.60 (m, 1H), 7.42 (d, J=7.4 Hz, 1H), 7.35 (d, J=8.1 Hz, 1H), 7.2 (m, 1H), 7.15 (d, J=8.4 Hz, 2H), 6.83 (d, J=8.4 Hz, 2H), 4.77 (d, J=4.7 Hz, 2H), 4.0–3.8 (m, 1H), 3.92 (q, J=7.4 Hz, 2H), 3.79 (s, 3H), 3.7–3.4 (m, 1H), 3.55 (dd, J=7.0, 24 Hz, 1H), 3.1–2.9 (m, 4H), 2.38 (m, 1H), 2.05 (m, 1H), 1.9–1.0 (m, 5H), 0.91 (t, J=7.1 Hz, 3H) ppm. ESMS m/z 605 (MH)$^+$.

EXAMPLE 58—FORMULA (III)

(8bS)-N-[(1R)-2,3-dihydro-1H-inden-1-yl]-7-(4-fluorobenzyl)-6,13-dioxo-5,8b,9,10,11,13-hexahydro-6H-benzo[c]pyrroizino[2,1-f][2,7]naphthyridine-3-carboxamide A. Ethyl (9aS)-4-(4-{[(1R)-2,3-dihydro-1H-inden-1-ylamino]carbonyl}-2-nitrophenyl)-2-[2-(4-fluorophenyl)ethyl]-5-oxo-7,8,9,9a-tetrahydro-5H-pyrido[2,3-a]pyrrolizine-3-carboxylate tert-Butyl (2S)-2-(3-ethoxy-3-oxopropanoyl)-1-pyrrolidinecarboxylate (1.95 g, 4.39 mmol, 1 equiv), ethyl (2Z)-3-amino-4-(4-fluorophenyl)-2-butenoate (1.04 g, 4.39 mmol, 1 equiv), 4-carboxy-2-nitrobenzaldehyde (0.856 g, 1.00 mmol, 1 equiv), and piperidine (0.218 mL, 2.20 mmol, 0.5 equiv) were combined in toluene (10.0 mL).

After 2 h at 90° C., the reaction was cooled to ambient temp. CAN (4.81 g, 8.78 mmol, 2 equiv) and H$_2$O (10.0 mL) were added. After 0.5 h the layers were separated. The aqueous portion was extracted with EtOAc (2×8 mL) and the combined organic portions were concentrated to a brown oil. The crude oil was then treated with 4 N HCl in dioxane (10.0 mL). After 1 h, the mixture was concentrated to a brown oil. A CH$_2$Cl$_2$ solution (10.0 mL) of this crude oil was treated with Et$_3$N (3.06 mL, 21.95 mmol, 5 equiv). After 8 h, the mixture was concentrated to a brown foam. A solution of the crude foam (0.533 g, 1.03 mmol, 1 equiv) in CH$_2$Cl$_2$ (2.0 mL) was treated with (R)-(–)-1-aminoindane (0.74 g, 2.06 mmol, 2 equiv), EDCI (0.297 g, 1.55 mmol, 1.5 equiv), and HOBt (0.210 g, 1.55 mmol, 1.5 equiv). After 12 h at ambient temperature, the reaction was diluted with CH$_2$Cl$_2$ (1.0 mL) and treated with saturated aqueous NaHCO$_3$ (4 mL). The organic portion was the washed with 1N HCl (4 mL) followed by brine (4 mL). Concentration gave a brown oil that was chromatographed radially (SiO$_2$, 2 mm plate, 50% hexanes-EtOAc) to ethyl (9aS)-4-(4-{[(1S)-2,3-dihydro-1H-inden-1-ylamino]carbonyl}-2-nitrophenyl)-2-[2-(4-fluorophenyl)ethyl]-oxo-7,8,9,9a-tetrahydro-5H-pyrido[2,3-a]pyrrolizine-3-carboxylate as a pale yellow foam (0.196 g, 30%): low resolution MS (ES$^+$) m/e 635 (MH$^+$); RP-HPLC (Dynamax C-18 25 cm×4.1 mm; 50–100% CH$_3$CN in H$_2$O with 0.1% TFA buffer; 25 minutes; 1 mL/min) t$_r$=12.87 min, 98% purity.

B. A solution of ethyl (9aS)-4-(4-{[(1R)-2,3-dihydro-1H-inden-1-ylamino]carbonyl}-2-nitrophenyl)-2-[2-(4-fluorophenyl)ethyl]-5-oxo-7,8,9,9a-tetrahydro-5H-pyrido[2,3-a]pyrrolizine-3-carboxylate (0.170 g, 0.27 mmol, 1 equiv) in a 1:1 mixture of ethanol and H$_2$O (10.0 mL) was treated with sodium dithionite (0.139 g, 0.80 mmol, 3 equiv). After 12 h, the reaction was acidified with 1 N HCl to ca. pH 5. Extraction with EtOAc (3×5 mL) was followed by drying (Na$_2$SO$_4$), and concentration. Trituration with acetone gave 0.133 g (88%) of analytically pure title compound as a light brown solid: $^1$H NMR (DMSO-d$_6$, 400 MHz) δ 11.96 (s, 1H), 9.70–9.67 (m, 1H), 8.97 (d, J=8.3 Hz, 1H), 7.82 (s, 1H), 7.66 (d, J=8.4 Hz, 1H), 7.25–7.15 (m, 5H), 7.00 (t, J=8.8 Hz, 2H), 5.57–5.51 (m, 1H), 5.00 (d, J=13.3 Hz, 1H), 4.88–4.84

(m, 2H), 3.64–3.59 (m, 1H), 3.36–3.24 (m, 2H), 3.00–2.94 (m, 1H), 2.86–2.78 (m, 1H), 2.46–2.23 (m, 4H), 2.00–1.94 (m, 1H), 1.40–1.35 (m, 1H).

EXAMPLE 59

(8bS)-N-[(1R)-2,3-dihydro-1H-inden-1-yl]-7-[2-(4-fluorophenyl)ethyl]-6,13-dioxo-5,8b,9,10,11,13-hexahydro-6H-benzo[c]pyrrolizino[2,1-f][2,7]naphthyridine-3-carboxamide A. A solution of ethyl (9aS)-4-(4-{[(1R)-2,3-dihydro-1H-inden-1-ylamino]carbonyl}-2-nitrophenyl)-2-[2-(4-fluorophenyl)ethyl]-5-oxo-7,8,9,9a-tetrahydro-5H-pyrido[2,3-a]pyrrolizine-3-carboxylate Example 53 (0.068 g, 0.11 mmol, 1 equiv) in a 1:1 mixture of ethanol and $H_2O$ (4.0 mL) was treated with sodium dithionite (0.057 g, 0.33 mmol, 3 equiv). After 12 h, the reaction was acidified with 1 N HCl to ca. pH 5. Extraction with EtOAc (3×3 mL) was followed by drying ($Na_2SO_4$), and concentration. Trituration with acetone gave 0.048 g (80%) of analytically pure title compound as a light brown solid: $^1$H NMR (DMSO-$d_6$, 400 MHz) δ 10.80 (s, 1H); low resolution MS ($ES^+$) m/e 573 ($MH^+$); RP-HPLC (Dynamax C-18 25 cm×4.1 mm; 50–100% $CH_3CN$ in $H_2O$ with 0.1% TFA buffer; 30 minutes; 1 mL/min) $t_r$=11.39 min, 97% purity.

EXAMPLE 60—FORMULA (IV)

Ethyl 4-(4-{[(1R)-2,3-dihydro-1H-inden-1-ylamino]carbonyl}phenyl)-2-(4-fluorobenzyl)-5-oxo-1,5,8,9-tetrahydro-4H,7H-pyrazolo[1',2':1,2]pyrazolo[3,4-b]pyridine-3-carboxylate A. Ethyl 4-(4fluorophenyl)-3-oxobutanoate DCC (9.2 g, 45 mmol) was added in portions to a stirred solution of 3-(4-fluorophenyl)acetic acid (6.9 g, 45 mmol), Meldrum's acid (6.5 g, 45 mmol) and DMAP (11 g, 90. mmol) in 90 mL DCM. After stirring at ambient temperature for 6 h, the reaction mixture was filtered through Celite, the filtrate was washed with 1N HCl (2×), water and brine and dried over $Na_2SO_4$. Filtration and concentration provided the acyl Meldrum's acid derivative as a yellow solid which was dissolved in 80 mL absolute EtOH and refluxed for 6 h. Concentration provided the β-ketoester as a yellow oil: $^1$H NMR (400 MHz, $CDCl_3$) 7.16 (dd, J=8.4, 6.0 Hz, 2H), 7.02 (t, J=8.6 Hz, 2H), 4.17 (dd, J=14.3, 7.1 Hz, 2H), 3.80 (s, 2H), 3.44 (s, 2H), 1.26 (t, J=7.1 Hz, 3H).

B. The title compound was prepared from ethyl 4-(4-fluorophenyl)-3-oxobutanoate as described in Steps C–D of Example 8 followed by coupling to (1R)-2,3-dihydro-1H-indene-1-amine as described in Step F of Example 8 and was obtained as an off-white solid: $^1$H NMR (400 MHz, DMSO-$d_6$) δ 9.87 (s, 1H), 8.59 (d, 1H, J=8), 7.71 (d, 2H, J=8), 7.30–7.10 (m, 10H), 5.49 (q, 1H, J=8), 4.79 (s, 1H), 4.20–3.70 (m, 4H), 3.40–2.20 (m, 9H), 1.94 (m, 1H), 0.94 (t, 3H, J=7) ppm; ESI-MS m/z 593 $(M+H)^+$.

EXAMPLE 61

Ethyl 4-(4-{[(1R)-2,3-dihydro-1H-inden-1-ylamino]carbonyl}phenyl)-5-oxo-2-{2-[4-(trifluoromethyl)phenyl]ethyl}-1,5,8,9-tetrahydro-4H,7H-pyrazolo[1',2':1,2]pyrazolo[3,4-b]pyridine-3-carboxylate The title compound was prepared from ethyl 3-oxo-5-[4-(trifluoromethyl)phenyl]pentanoate (Example 2B) as described in Steps C–D of Example 8 followed by coupling to (1R)-2,3-dihydro-1H-indene-1-amine as described in Step F of Example 8 and was obtained as an off-white solid: $^1$H NMR (400 MHz, DMSO-$d_6$) δ 9.74 (s, 1H), 8.59 (d, 1H, J=8), 7.71 (d, 2H, J=8), 7.64 (d, 2H, J=8), 7.45 (d, 2H, J=8), 7.15 (m, 6H), 5.49 (q, 1H, J=8), 4.73 (s, 1H), 3.86 (m, 2H), 3.39 (m, 2H), 3.25 (m, 2H), 2.94 (m, 4H), 2.80 (m, 2H), 2.41 (m, 1H), 2.23 (m, 2H), 1.91 (m, 1H), 0.98 (t, 3H, J=7) ppm; ESI-MS m/z 657 $(M+H)^+$.

Biological Data

The compounds of the present invention elicit important and measurable pharmacological responses. As is to be expected, the efficacy of any compound will vary depending upon the particular assay and the particular compound tested. Each of the compounds exemplified in the Examples section activate with high potency ($EC_{50}$<10 μM) the human calcitonin-2 receptor (hCT2R) as described by the calcitonin receptor reporter assays recited below.

All recombinant cell line human calcitonin receptor assays were carried out with the human receptor corresponding to GeneBank Accession Number X69920, [See: Molecular Pharmacology 46 (2):246–255, 1994, Cloning and characterization of an abundant subtype of the human calcitonin receptor] cloned from the MCF7 cell line (American Type Tissue Collection, Manassas, Va., USA, Catalog # HTB-22). Human calcitonin receptor (hCT2R) was cloned as a HindIII fragment into plasmid BS SKII. Chinese hamster ovary cells were co-transfected with a 6CRE-luciferase reporter system and hCTR2. HEK cells were transfected with hCTR2.

CRE-luciferase Reporter Assays:

Suspension Assay (High Throughput Screening)

CHO-6CRE-luciferase cells with or without co-expressed hCTR2 were grown in suspension in commercially available cell culture medium supplemented with 2 mM L-glutamine and 5% fetal bovine serum (FBS). Sixteen hours before each assay, cells were collected and resuspended at 1,000,000 cells/ml in media without FBS. Cells were cultured in spinner flasks at 37° C. in an atmosphere of 5% $CO_2$. At the time of the assay, cells were pelleted by centrifugation and resuspended in media without FBS at a concentration of 250,000 cells/ml. The cell suspension was pipetted into black 96-well microtiter plates (25,000 cells/well) containing test compounds. After a four-hour incubation at 37° C., media was aspirated, followed by addition of 50 microliters of LucLite and PBS (1:1) containing 1 mM $CaCl_2$ and 1 mM $MgCl_2$. The plates were sealed and incubated for 20 minutes in the dark. Luminescent responses were measured using a Packard TopCount.

Adherent Assay (Structure-activity Studies)

Structure activity studies were performed on CHO-6CRE-luciferase cells with or without co-transfected hCT2R. Forty-eight hours before each assay, cells were removed with trypsin and plated in 96-well microtiter plates at a concentration of 25–100,000 cells/well. Sixteen hours before each assay, FBS-containing media was removed and replaced with media without FBS. Compounds were added and incubated for four hours at 37° C. After incubation, media was aspirated and 50 microliters of LucLite in PBS (1:1) containing 1 mM $CaCl_2$ and 1 mM $MgCl_2$ were added to each well. Plates were sealed and incubated for 20 minutes in the dark before quantification of luminescence on a Packard TopCount.

Concentration-response curves were calculated and potencies were reported as the concentration of compounds producing half-maximal responses (EC50) or the negative log of the concentration of compounds producing half-maximal responses (pEC50).

TABLE 1

Agonist Activities

| Example | HCT2R CRE-luc reporter assay $EC_{50}$ nM |
|---|---|
| 1 | +++ |
| 2 | ++ |
| 3 | ++ |
| 4 | +++ |
| 5 | ++ |
| 6 | +++ |
| 7 | ++ |
| 8 | ++++ |
| 9 | ++++ |
| 10 | + |
| 11 | ++++ |
| 12 | +++ |
| 13 | + |
| 14 | ++ |
| 15 | ++++ |
| 16 | ++++ |
| 17 | ++++ |
| 18 | ++++ |
| 19 | ++++ |
| 20 | +++ |
| 21 | +++ |
| 22 | +++ |
| 23 | +++ |
| 24 | ++ |
| 25 | ++ |
| 26 | ++ |
| 27 | ++ |
| 28 | ++ |
| 29 | +++ |
| 30 | ++ |
| 31 | ++++ |
| 32 | + |
| 33 | +++ |
| 34 | ++++ |
| 35 | +++ |
| 36 | +++ |
| 37 | ++ |
| 38 | ++ |
| 39 | +++ |
| 40 | ++ |
| 41 | ++ |
| 42 | ++ |
| 43 | ++++ |
| 44 | +++ |
| 45 | +++ |
| 46 | ++ |
| 47 | +++ |
| 48 | + |
| 49 | + |
| 50 | + |
| 51 | ++ |
| 52 | +++ |
| 53 | +++ |
| 54 | + |
| 55 | +++ |
| 56 | ++ |
| 57 | + |
| 58 | ++ |
| 59 | ++++ |
| 60 | ++ |
| 61 | +++ |

Activity in human Reporter assay
++++ EC50 10 nM or less
+++ EC50 about 10 to 100 nM
++ EC50 about 100 to 1000 nM
+ EC50 about 1000 to 10000 nM or greater Human Osteoclast Assay—In Vitro Human osteoclasts were differentiated from peripheral blood cells using methods adapted from published protocols [Journal of Experimental Medicine 188(5):997–1001, 1998. TRANCE is necessary and sufficient for osteoblast-mediated activation of bone resorption in osteoclasts. K Fuller, B Wong, S Fox, Y Choi, and T J Chambers]. Human mononuclear cells were incubated on bone slices in M_CSF (30 ng/ml) and RANKL (TRANCE, 30 ng/ml) for 10 days. Differentiated osteoclasts were identified using an osteoclast-specific monoclonal antibody. Osteoclasts with test compounds or vehicle were incubated on cortical bone slices for an additional 3 to 7 days to measure bone resorption. In addition to bone resorption, toxicity and osteoclastogenesis were observed after compound treatments. A positive response was defined as significant inhibition of bone resorption without toxicity.

Rat Calvaria Assay—In Vitro

Bone resorption of neonatal rat cavarial chips was measured using methods adapted from published protocols [Ulf H, Lerner Modifications of the Mouse Calvarial Technique Improve the Responsiveness to Stimulators of Bone Resorption. Journal of Bone and Mineral Research Vol 2, No. 5, 1987]. Resorption was measured by quantification of calcium in the supernatant by a calorimetric assay and of deoxypyridinoline in the supernatant by ELISA. Deoxypyridinoline is released as a by product of collagen degradation by the osteoclast Calvaria were surgically removed from 2–3 day old Wistar rats and placed in a sterile tube containing BGJb media (Fitton-Jackson Modification)—GIBCO BRL with penicillin (10 U/ml)/streptomycin (10 µg/ml). Calvaria were washed twice with fresh media, trimmed of excess tissue, and placed in fresh media. Calvaria were uniformly sectioned and placed in the wells of a tissue culture plate in 1 ml of BGJb/P/S with 1 mg/ml BSA. Calvaria were incubated for 24 hours at 37° C., 5% $CO_2$ before treatments. Media was aspirated and replaced with 1 ml of fresh media containing PTH 10 ng/ml. Unstimulated wells contained media alone. Test compounds or calcitonin (1 ng/ml) were added. Compounds or calcitonin were added again on days 2 and 3, with no medium or PTH additions. Upon completion of the assay, the media was collected and stored at −20° C. until analysis was performed. Calvaria were air-dried for several days, and dry weight was quantified.

Deoxypyridinoline ELISA: Supernatants were evaluated for deoxypyridinoline crosslinks according to kit manufacturer instructions. SoftMax software was used to evaluate ELISA data from a 96-well format to generate a standard curve. Sample values were extrapolated from this standard curve. Extrapolated sample values were imported into a Microsoft Excel to normalize sample values to dried calvarial weight. Data was expressed as nanomolar DPD/mg calvaria.

Calcium analysis: Calcium determinations were made using Arsenazo III reagent from Sigma Diagnostics No. 588. Procedure followed as described by manufacturer in kit instructions. Data was imported from plate reader into Microsoft® Excel® and calcium concentrations were calculated as follows:

$$[A_{sample}/A_{standard}] \times \text{Concentration of standard} = \text{mg/dL Calcium}$$

Sample values were normalized to dried calvarial weight and expressed as mg/dL calcium per mg calvaria.

Rat TPTX Assay—In Vivo

Thyroid-parathyroidectomized (TPTX) rats were used to determine the effects of compounds on PTH-induced elevation of serum calcium in vivo. The thyroid and parathyroid glands of male CD rats were removed under anesthesia and subcutaneous pumps containing human parathyroid hormone (hPTH 1–34) were implanted two to five days after TPTX. Rats were grouped (n=4/group) so that mean serum calcium did not significantly differ among control and treatment groups. PTH was delivered at a rate of 30 micrograms/kg/hour. PTH causes significant elevations of serum calcium in TPTX rats given no other treatments. Rats were treated with vehicle, test compounds at various doses or calcitonin 16 units/kg SC. This dose of calcitonin causes maximal suppression of PTH-induced hypercalcemia in TPTX rats. Serum calcium was measured at baseline and every two hours up to six hours. Averaged group responses at each time point were compared using Analysis of Variance (ANOVA).

TABLE 2

Activity of selected compounds in secondary assays of bone resorption

| Compound | Human osteoclast in vitro | Rat calvaria in vitro | TPTX rat in vivo |
| --- | --- | --- | --- |
| Example 4  | NT     | Active | Active |
| Example 11 | Active | Active | NT     |
| Example 5  | NT     | Active | Active |
| Example 16 | NT     | Active | Active |
| Example 12 | Active | Active | Active |

Definitions of Active:
Human osteoclast: Significant inhibition of bone resorption in the absence of toxicity, relative to vehicle-treated controls.
Rat calvaria: Concentration-dependent inhibition of bone resorption with efficacy equivalent to calcitonin 1 ng/ml.
TPTX (Thyroid- parathyroidectomized) rat: Significant inhibition of bone resorption reflected in serum calcium levels relative to PTH + Vehicle controls.
NT: not tested.

What is claimed is:

1. A compound selected from the group consisting of:
Ethyl 2-[2-(4-fluorophenyl)ethyl]-4-(4-{[(2-furylmethyl)amino]carbonyl}phenyl)-5-oxo-8,9-dihydro-5H,7H-pyrazolo[1',2':1,2]pyrazolo[3,4-b]pyridine-3-carboxylate;
Ethyl 2-[2-(4-fluorophenyl)ethyl]-4-(5-{[(2-furylmethyl)amino]carbonyl}-2-thienyl) -5-oxo-8,9-dihydro-5H,7H-pyrazolo[1',2':1,2]pyrazolo[3,4-b]pyridine-3-carboxylate;
Ethyl (9aS)-5-oxo-4-[4-({[(1R)-1-(4-pyridinyl)ethyl]amino}carbonyl)phenyl]-2-{2-[4-(trifluoromethyl)phenyl]ethyl}-7,8,9,9a-tetrahydro-5H-pyrido[2,3-a]pyrrolizine-3-carboxylate;
Ethyl (9aS)-4-(4-{[(2-furylmethyl)amino]carbonyl}phenyl)-5-oxo-2-{2-[4-(trifluoromethyl)phenyl]ethyl}-7,8,9,9a-tetrahydro-5H-pyrido[2,3-a]pyrrolizine-3-carboxylate;
Ethyl (9aS)-4-{4-[(2,3-dihydro-1H-inden-1-ylamino)carbonyl]-2-thienyl}-2-[2-(4-fluorophenyl)ethyl]-5-oxo-7,8,9,9a-tetrahydro-5H-pyrido[2,3-a]pyrrolizine-3-carboxylate;
Ethyl (9aS)-4-(4-{[(3,4-difluorobenzyl)amino]carbonyl}-2-thienyl)-2-[2-(4-fluorophenyl)ethyl]-5-oxo-7,8,9,9a-tetrahydro-5H-pyrido[2,3-a]pyrrolizine-3-carboxylate;
Ethyl (9aS)-4-{4-[(2,3-dihydro-1H-inden-1-ylamino)carbonyl]-2-furyl}-2-[2-(4-fluorophenyl)ethyl]-5-oxo-7,8,9,9a-tetrahydro-5H-pyrido[2,3-a]pyrrolizine-3-carboxylate;
Ethyl (9aS)-4-(5-{[(1R)-2,3-dihydro-1H-inden-1-ylamino]carbonyl}-2-thienyl)-2-[2-(4-fluorophenyl)ethyl]-5-oxo-7,8,9,9a-tetrahydro-5H-pyrido[2,3-a]pyrrolizine-3-carboxylate;
Ethyl (9aS)-4-(5-{[(1R)-2,3-dihydro-1H-inden-1-ylamino]carbonyl}-1,3-thiazol-2-yl)-2-(4-fluorobenzyl)-5-oxo-7,8,9,9a-tetrahydro-5H-pyrido[2,3-a]pyrrolizine-3-carboxylate;
4-{(9aS)-2-(2,4-difluorobenzyl)-5-oxo-3-[(trifluoroacetyl)amino]-7,8,9,9a-tetrahydro-5H-pyrido[2,3-a]pyrrolizin-4-yl}-N-[(1R)-2,3-dihydro-1H-inden-1-yl]benzamide;
Ethyl (9aS)-4-[4-({[2-(1H-imidazol-5-yl)ethyl]amino}carbonyl)phenyl]-5-oxo-2-{2-[4-(trifluoromethyl)phenyl]ethyl}-7,8,9,9a-tetrahydro-5H-pyrido[2,3-a]pyrrolizine-3-carboxylate;
and
Ethyl (9aS)-4-(4-{[1R)-2,3-dihydro-1H-inden-1-ylamino]carbonyl}phenyl)-2-(4-methylpentyl)-5-oxo-7,8,9,9a-tetrahydro-5H-pyrido[2,3-a]pyrrolizine-3-carboxylate.

* * * * *